United States Patent
Wang et al.

(10) Patent No.: US 10,696,713 B2
(45) Date of Patent: *Jun. 30, 2020

(54) BILE ACID DERIVATIVES AS FXR/TGR5 AGONISTS AND METHODS OF USE THEREOF

(71) Applicant: Enanta Pharmaceuticals, Inc., Watertown, MA (US)

(72) Inventors: Guoqiang Wang, Belmont, MA (US); Yat Sun Or, Waltham, MA (US); Ruichao Shen, Belmont, MA (US); Jiang Long, Wayland, MA (US); Peng Dai, Auburndale, MA (US); Xuechao Xing, Wilmington, MA (US); Jing He, Somerville, MA (US)

(73) Assignee: ENANTA PHARMACEUTICALS, INC., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/222,380

(22) Filed: Dec. 17, 2018

(65) Prior Publication Data

US 2019/0194245 A1      Jun. 27, 2019

Related U.S. Application Data

(63) Continuation of application No. 14/951,989, filed on Nov. 25, 2015, now Pat. No. 10,208,081.

(60) Provisional application No. 62/084,769, filed on Nov. 26, 2014, provisional application No. 62/103,374, filed on Jan. 14, 2015.

(51) Int. Cl.
| | | |
|---|---|---|
| C07J 41/00 | (2006.01) | |
| C07J 43/00 | (2006.01) | |
| C07J 9/00 | (2006.01) | |
| C07J 51/00 | (2006.01) | |

(52) U.S. Cl.
CPC ........ *C07J 41/0066* (2013.01); *C07J 41/0055* (2013.01); *C07J 41/0088* (2013.01); *C07J 43/003* (2013.01); *C07J 43/006* (2013.01); *C07J 9/005* (2013.01); *C07J 41/0094* (2013.01); *C07J 51/00* (2013.01)

(58) Field of Classification Search
CPC .... C07J 9/005; C07J 41/0055; C07J 41/0066; C07J 41/0088; C07J 41/0094; A61K 31/575

See application file for complete search history.

(56) References Cited

U.S. PATENT DOCUMENTS

| | | |
|---|---|---|
| 4,202,876 A | 5/1980 | Monks et al. |
| 5,466,815 A | 11/1995 | Enhsen et al. |
| 5,512,558 A | 4/1996 | Enhsen et al. |
| 5,646,316 A | 7/1997 | Jacobson et al. |
| 5,656,277 A | 8/1997 | Berlati et al. |
| 7,858,608 B2 | 12/2010 | Pellicciari et al. |
| 2005/0054559 A1 | 3/2005 | Gallop et al. |
| 2007/0142340 A1 | 6/2007 | Pellicciari et al. |
| 2008/0039435 A1 | 2/2008 | Pellicciari et al. |
| 2008/0182832 A1 | 7/2008 | Pellicciari et al. |
| 2008/0214515 A1 | 9/2008 | Ferrari et al. |
| 2009/0062526 A1 | 3/2009 | Yu et al. |
| 2009/0163474 A1 | 6/2009 | Zhang et al. |
| 2010/0063018 A1 | 3/2010 | Pellicciari et al. |
| 2010/0324004 A1 | 12/2010 | McLane et al. |
| 2011/0172198 A1 | 7/2011 | Pellicciari et al. |
| 2013/0116218 A1 | 5/2013 | Kaplan et al. |
| 2013/0345188 A1 | 12/2013 | Steiner et al. |
| 2014/0057886 A1 | 2/2014 | Pellicciari et al. |
| 2014/0186438 A1 | 7/2014 | Manku et al. |
| 2014/0187633 A1 | 7/2014 | Manku et al. |
| 2014/0206657 A1 | 7/2014 | Yu et al. |
| 2014/0371190 A1 | 12/2014 | Pellicciari |
| 2015/0112089 A1 | 4/2015 | Finch et al. |
| 2016/0130297 A1 | 5/2016 | Xing et al. |

(Continued)

FOREIGN PATENT DOCUMENTS

| | | |
|---|---|---|
| CN | 105175473 A | 12/2015 |
| CN | 106478759 A | 3/2017 |

(Continued)

OTHER PUBLICATIONS

"Mosesin-4' at www.chemspider.com/ Chemical-Structure.10375019. html (retrieved from the internet Oct. 11, 2016)".

(Continued)

*Primary Examiner* — Barbara P Badio

(74) *Attorney, Agent, or Firm* — Edgar W. Harlan; Carolyn S. Elmore; Elmore Patent Law Group, P.C.

(57) ABSTRACT

The present invention provides compounds of Formula I,

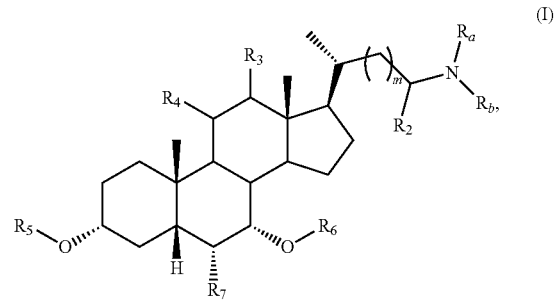

pharmaceutical compositions comprising these compounds and methods of using these compounds to prevent or treat FXR-mediated or TGR5-mediated diseases or conditions.

15 Claims, No Drawings

(56) References Cited

U.S. PATENT DOCUMENTS

| | | | |
|---|---|---|---|
| 2016/0145295 | A1 | 5/2016 | He et al. |
| 2016/0145296 | A1 | 5/2016 | Shen et al. |
| 2016/0176917 | A1 | 6/2016 | Shen et al. |
| 2016/0185815 | A1 | 6/2016 | Shen et al. |
| 2016/0229886 | A1 | 8/2016 | Or et al. |
| 2016/0289262 | A1 | 10/2016 | Or et al. |
| 2017/0101434 | A1 | 4/2017 | Pellicciari et al. |
| 2017/0240585 | A1 | 8/2017 | Shen et al. |
| 2017/0240586 | A1 | 8/2017 | Or et al. |
| 2017/0240587 | A1 | 8/2017 | Or et al. |
| 2017/0260225 | A1 | 9/2017 | Pellicciari et al. |
| 2018/0148469 | A1 | 5/2018 | Wang et al. |
| 2018/0148470 | A1 | 5/2018 | Li et al. |
| 2018/0237471 | A1 | 8/2018 | Wang et al. |
| 2018/0291058 | A1 | 10/2018 | Wang et al. |

FOREIGN PATENT DOCUMENTS

| | | |
|---|---|---|
| CN | 106518946 A | 3/2017 |
| EA | 200970698 A1 | 2/2010 |
| EP | 0583566 A2 | 2/1994 |
| EP | 1364645 A1 | 11/2003 |
| EP | 1947108 A1 | 7/2008 |
| EP | 3290429 A1 | 3/2018 |
| JP | H1160594 A | 3/1999 |
| JP | H11109628 A | 4/1999 |
| WO | 8702367 A2 | 4/1987 |
| WO | 9526325 A1 | 10/1995 |
| WO | 0037077 A1 | 6/2000 |
| WO | 0228881 A1 | 4/2002 |
| WO | 03030612 A2 | 4/2003 |
| WO | 03086303 A2 | 10/2003 |
| WO | 2005089316 A2 | 9/2005 |
| WO | 2007089907 A2 | 8/2007 |
| WO | 2007095174 A2 | 8/2007 |
| WO | 2007111994 A2 | 10/2007 |
| WO | 2008009407 A2 | 1/2008 |
| WO | 2008091540 A2 | 7/2008 |
| WO | 2010014836 A2 | 2/2010 |
| WO | 2010093845 A1 | 8/2010 |
| WO | 2013020108 A2 | 2/2013 |
| WO | 2013166176 A1 | 11/2013 |
| WO | 2013192097 A1 | 12/2013 |
| WO | 2014036379 A2 | 3/2014 |
| WO | 2014184271 A1 | 11/2014 |
| WO | 2015017813 A2 | 2/2015 |
| WO | 2015181275 A1 | 12/2015 |
| WO | 2016173493 A1 | 11/2016 |
| WO | 2016173524 A1 | 11/2016 |
| WO | 2016205475 A2 | 12/2016 |
| WO | 2017027396 A1 | 2/2017 |
| WO | 2017053826 A1 | 3/2017 |
| WO | 2017129125 A1 | 8/2017 |

OTHER PUBLICATIONS

"PubChem-CID-122592927, Create Date: Dec. 8, 2016".

"PubChem-CID-122592945, Create Date: Dec. 8, 2016".

Ali, et al., "Recent advances in the development of farnesoid X receptor agonists", Ann Transl Med, 3(1), 2015, 1-16.

Ballatore, C. et al., "Carboxylic Acid (Bio)Isosteres in Drug Design", ChemMedChem., vol. 8, No. 3, 2013, 385-395.

Banker, G. S. et al., Modern Pharmaceutics, 3rd., Marcel Dekker, Inc., NY, 1996, 596.

Briere, D. A. et al., "Novel small molecule agonist of TGR5 possesses anti-diabetic effects but causes gallbladder filling in mice", PLoS, one, vol. 10(8), 2015, 1-17.

Bundgaard, H., "Design of Prodrugs: Bioreversible derivatives for various functional groups and chenmical entitites", Hans Bundgaard: "Design of Prodrugs", Elsevier, Amsterdam, New York, Oxford; Chapeter 1, 1985.

Coleman, J. P. et al., "Metabolic Fate and Hepatocyte Toxicity of Reverse Amide Analogs of Conjugated Ursodeoxycholate in the Rat", J. Steroid Biochem. Molec. Biol., vol. 64, No. 1/2, 1998, 91-101.

Crawley, "Farnesoid X Receptor Modulators: a patent review", Expert Opinion on Therapeutic Patents, 20(8), 2010, 1047-1057.

Fini, A. et al., "Basic Cholane Derivatives. XI: Comparison between Acid and Basic Derivatives", Journal of Pharmaceutical Sciences, vol. 81, No. 7, 1992, 726-730.

Fini, A. et al., "Quantitative Structure-Antimicrobial Activity Relationship in 5B-Cholanyl-24-benzylamine Derivatives", Journal of Pharmaceutical Sciences, vol. 79, No. 7, 1990, 603-605.

Gioiello, A, et al., "Extending SAR of bile acids as FXR ligands: discovery of 23-N-(carbocinnamyloxy)-3[alpha],7[alpha]dihydroxy-6[alpha]-ethyl-24-nor-5[beta]-ch o 1 an-23-amine", Bioorganic & Medicinal Chemistry, vol. 19, No. 8, Apr. 15, 2011, 2650-2658.

Griffiths, W. J. et al., "Charge-remote fragmentation of bile acids derivatized with amino-sulphonic acids", Rapid Communications in Mass Spectrometry, vol. 7, No. 3, Mar. 1, 1993, 235-240.

Honorio, K. M. et al., "Hologram QSAR Studies on Farnesoid X Receptor Activators", Letters in Drug Design & Discovery, vol. 3, 2006, 261-267.

Kim, H-S, et al., "Synthesis and Antimicrobial Activity of New 3a-Hydroxy-23,24-bisnorcholane Polyamine Carbamates", Bioorganic & Medicinal Chemistry Letters, 11(23), 2001, 3065-3068.

Macchiarulo, A. et al., "Probing the Binding Site of Bile Acids in TGR5", Medicinal Chemistry Letters, 4(12):, 2011, 1158-1162.

Mayorquin-Torres, M. C. et al., "application of palladium-catalyzed carboxyl anhydride-boronic acid cross coupling in the synthesis of novel bile acids analogs and modified side chains", Steroids, vol. 101, 2015, 21-27.

Nikolaienko, P. V. et al., "Rapid way to fluorescent cholic-based chemosensor precursors", International Electronic Conference on Synthetic Organic Chemistry, 2011, 1-4.

Okahata, Y. et al., "Catalytic Hydrolysis of p-Nitrophenyl Esters in the Presence of Representative Ammonium Aggregates. Specific u Activation of a Cholesteryl Nucleophile Bound to a Dialkylammonium Bilayer Membrane", Bulletin of hte Chemical Society of Japan, vol. 52(12), Dec. 1, 1979, 3647-3653.

Opsenica, I. M. et al., "4-Amino-7-chloroquinolines: Probing Ligand Efficiency Provides Botulinum Neurotoxin Serotype a Light Chain Inhibitors with Significant Antiprotozoal Activity", J. Med. Chem., vol. 56, 2013, 5860-5871.
Pellicciari, R. et al., "6α-Ethyl-Chenodeoxycholic Acid (6-ECDCA), a Potent and Selective FXR Agonist Endowed with Anticholestatic Activity", Journal of Medicinal Chemistry, 45(17), 2002, 3569-3572.
Pellicciari, R. et al., "Back Door Modulation of the Farnesoid X Receptor: Design, Synthesis and Biological Evaluation of a Series of Side Chain Modified Chenodeoxycholic Acid Derivatives", Journal of Medicinal Chem., American Chemical Society, vol. 49, Jun. 15, 2006, 4208-4215.
Pellicciari, R. et al., "Bile Acid Derivatives as Ligands of the Farnesoid X Receptor. Synthesis, Evaluation, and Structure-Activity Relationship of a Series of Body and Side Chain Modified Analogues of Chenodeoxycholic Acid", Journal of Medicinal Chemistry, American Chemical Society, vol. 47, Jul. 23, 2004, 4559-4569.
Pore, V. S. et al., "Design and synthesis of fluconazole/bile acid conjugate using click reaction", Tetrahedron, vol. 62, 2006, 11178-11186.
Sajisha, et al., "Remarkable isomer-selective gelation of aromatic solvents by a polymorph of a urea-linked bile acid-amino acid conjugate", RSC Advances, vol. 4(81), Abstract Only, 2014, 43167-43171.
Sato, et al., "Novel Potent and Selective Bile Acid Derivatives as TGR5 Agonists: Biological Screening, Structure-Activity Relationships, and Molecular Modeling Studies", J. Med. Chem., 51(6), 2008, 1831-1841.
Sepe, et al., "Farnesoid X receptor modulators (2011-2014): a patent review", Expert Opinion on Therapeutic Patents, 25:8, 2015, 885-896.
Silverman, R. B., "Prodrugs and Drug Delivery Systems", The Organic Chemistry of Drug Design and Drug Action. Published by Academic Press, 1992, 352-397.

(56) References Cited

OTHER PUBLICATIONS

Solaja, B. A. et al., "Novel 4-Aminoquinolines Active against Chloroquine-Resistant and Sensitive P. falciparum Strains that also Inhibit Botulinum Serotype A", J. Med. Chem., vol. 51, 2008, 4388-4391.
Willemen, H. M. et al., "Alkyl Derivatives of Cholic Acid as Organogelators: One-Component and Two-Component Gels", Langmuir, vol. 18(19), 2002, 7102-7106.
Wolff, M. E., Burger's Medicinal Chemistry and Drug Discovery, Fifth Edition, vol. 5(1): Principles and Practice published by John Wiley and Sons, 1994, 975-977.
U.S. Appl. No. 16/222,380, filed Dec. 17, 2018.
Okada, J., "Preparation of bile acid derivatives and their use as nasal absorption enhancers", Database CA [Online] Chemical Abstracts Service, Columbus, Ohio, US; retrieved from STN Database accession No. 1999:142390.
Okahata, Y. et al., "Base-catalyzed proton abstraction from .beta.-(p-nitrophenoxy)propiophenone in the presence of single-chain, double-chain, and triple-chain ammonium bilayer membrane aggregates", Database CA [Online] Chemical Abstracts Service, Database accession No. 1980:549272, abstract, 1980.
Roda, A. et al., "Effect of Basic Cholane Derivatives on Intestinal Cholic Acid Metabolism: In Vitro and In Vivo Activity", Journal of Pharmaceutical Sciences, vol. 81, No. 3, 1992, 237-240.
Meijide, F. et al., "Spontaneous Formation in the Solid State of Carbamate Derivatives of Bile Acids", Crystal Growth and Design, 11(1), 2011, 356-361.
Videnovic, M. et al., "Second Generation Steroidal 4-Aminoquinolines Are Potent, Dual-Target Inhibitors . . . ", J. Med. Chem., 57(10), Apr. 17, 2014, 4134-4153.
Zaragoza Dorwald, F., "Side Reactions in Organic Synthesis", 2005, Wiley-VCH Verlag GmbH & Co. KGaA, Weinheim, Preface. p. IX, 2005.

BILE ACID DERIVATIVES AS FXR/TGR5 AGONISTS AND METHODS OF USE THEREOF

RELATED APPLICATIONS

This application is a continuation of U.S. application Ser. No. 14/951,989, filed Nov. 25, 2015, which claims the benefit of U.S. Provisional Application No. 62/084,769, filed on Nov. 26, 2014, and U.S. Provisional Application No. 62/103,374, filed on Jan. 14, 2015. The entire teachings of the above applications are incorporated herein by reference.

TECHNICAL FIELD

The present invention relates generally to compounds and pharmaceutical compositions useful as FXR/TGR5 modulators. Specifically, the present invention relates to bile acid derivatives and methods for their preparation and use.

BACKGROUND OF THE INVENTION

Farnesoid X Receptor (FXR) is an orphan nuclear receptor initially identified from a rat liver cDNA library (B M. Forman, et al., *Cell,* 1995, 81(5), 687-693) that is most closely related to the insect ecdysone receptor. FXR is a member of the nuclear receptor family of ligand-activated transcription factors that includes receptors for the steroid, retinoid, and thyroid hormones (DJ. Mangelsdorf, et al., *Cell,* 1995, 83(6), 841-850). The relevant physiological ligands of FXR are bile acids (D. Parks et al., *Science,* 1999, 284(5418), 1362-1365). The most potent one is chenodeoxycholic acid (CDCA), which regulates the expression of several genes that participate in bile acid homeostasis. Farnesol and derivatives, together called farnesoids, are originally described to activate the rat orthologue at high concentration but they do not activate the human or mouse receptor. FXR is expressed in the liver, throughout the entire gastrointestinal tract including the esophagus, stomach, duodenum, small intestine, colon, ovary, adrenal gland and kidney. Beyond controlling intracellular gene expression, FXR seems to be also involved in paracrine and endocrine signaling by upregulating the expression of the cytokine Fibroblast Growth Factor (J. Holt et al., *Genes Dev.,* 2003, 17(13), 1581-1591; T. Inagaki et al., *Cell Metab.,* 2005, 2(4), 217-225).

Small molecule compounds which act as FXR modulators have been disclosed in the following publications: WO 2000/037077, WO 2003/015771, WO 2004/048349, WO 2007/076260, WO 2007/092751, WO 2007/140174, WO 2007/140183, WO 2008/051942, WO 2008/157270, WO 2009/005998, WO 2009/012125, WO 2008/025539, WO 2008/025540, WO 2011/020615, and WO 2013/007387.

Further small molecule FXR modulators have been recently reviewed (R. C. Buijsman et al. *Curr. Med. Chem.* 2005, 12, 1017-1075).

TGR5 receptor is a G-protein-coupled receptor that has been identified as a cell-surface receptor that is responsive to bile acids (BAs). The primary structure of TGR5 and its responsiveness to bile acids has been found to be highly conserved in TGR5 among human, bovine, rabbit, rat, and mouse, and thus suggests that TGR5 has important physiological functions. TGR5 has been found to be widely distributed in not only lymphoid tissues but also in other tissues. High levels of TGR5 mRNA have been detected in placenta, spleen, and monocytes/macrophages. Bile acids have been shown to induce internalization of the TGR5 fusion protein from the cell membrane to the cytoplasm (Kawamata et al., *J. Bio. Chem.,* 2003, 278, 9435). TGR5 has been found to be identical to hGPCR19 reported by Takeda et al., *FEBS Lett.* 2002, 520, 97-101.

TGR5 is associated with the intracellular accumulation of cAMP, which is widely expressed in diverse cell types. While the activation of this membrane receptor in macrophages decreases pro-inflammatory cytokine production, (Kawamata, Y., et al., *J. Biol. Chem.* 2003, 278, 9435-9440) the stimulation of TGR5 by BAs in adipocytes and myocytes enhances energy expenditure (Watanabe, M., et al. *Nature.* 2006, 439, 484-489). This latter effect involves the cAMP-dependent induction of type 2 iodothyronine deiodinase (D2), which by, locally converting T4 into T3, gives rise to increased thyroid hormone activity. Consistent with the role of TGR5 in the control of energy metabolism, female TGR5 knock-out mice show a significant fat accumulation with body weight gain when challenged with a high fat diet, indicating that the lack of TGR5 decreases energy expenditure and elicits obesity (Maruyama, T., et al., *J. Endocrinol.* 2006, 191, 197-205). In addition, and in line with the involvement of TGR5 in energy homeostasis, bile acid activation of the membrane receptor has also been reported to promote the production of glucagon-like peptide 1 (GLP-1) in murine enteroendocrine cell lines (Katsuma, S., *Biochem. Biophys. Res. Commun.,* 2005, 329, 386-390). On the basis of all the above observations, TGR5 is an attractive target for the treatment of disease e.g., obesity, diabetes and metabolic syndrome.

In addition to the use of TGR5 agonists for the treatment and prevention of metabolic diseases, compounds that modulate TGR5 modulators are also useful for the treatment of other diseases e.g., central nervous diseases as well as inflammatory diseases (WO 01/77325 and WO 02/84286). Modulators of TGR5 also provide methods of regulating bile acid and cholesterol homeostasis, fatty acid absorption, and protein and carbohydrate digestion.

There is a need for the development of FXR and/or TGR5 modulators for the treatment and prevention of disease. The present invention has identified compounds, which contain an amino, urea, sulfonyurea or sulfonamide moieties, which modulate FXR and/or TGR as well as methods of using these compounds to treat disease.

SUMMARY OF THE INVENTION

In one aspect, the invention provides compounds represented by Formula I, or pharmaceutically acceptable salts, stereoisomers, solvates, hydrates or combinations thereof:

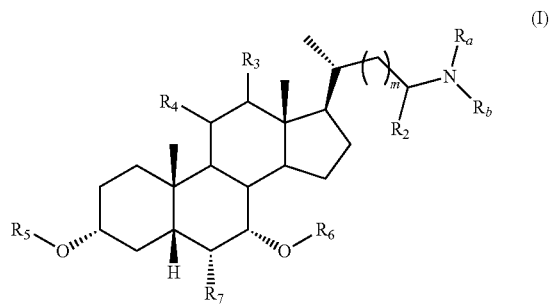

wherein:

$R_a$ is hydrogen or substituted or unsubstituted —$C_1$-$C_8$ alkyl; preferably $R_a$ is hydrogen or methyl; more preferably, $R_a$ is hydrogen;
$R_b$ is selected from the group consisting of:
1) Hydrogen;
2) —C(O)NR$_{10}$R$_{11}$;
3) —C(O)NHSO$_2$R$_1$; and
4) —SO$_2$R$_1$;
$R_1$ is selected from the group consisting of:
1) Halogen;
2) Hydroxyl;
3) Substituted or unsubstituted —$C_1$-$C_8$ alkyl;
4) Substituted or unsubstituted —$C_2$-$C_8$ alkenyl;
5) Substituted or unsubstituted —$C_2$-$C_8$ alkynyl;
6) Substituted or unsubstituted —$C_3$-$C_8$ cycloalkyl;
7) Substituted or unsubstituted aryl;
8) Substituted or unsubstituted arylalkyl;
9) Substituted or unsubstituted heterocycloalkyl;
10) Substituted or unsubstituted heteroaryl;
11) Substituted or unsubstituted heteroarylalkyl; and
12) —NR$_{10}$R$_{11}$;
$R_2$ is selected from the group consisting of:
1) Hydrogen;
2) Substituted or unsubstituted —$C_1$-$C_8$ alkyl;
3) Substituted or unsubstituted —$C_2$-$C_8$ alkenyl;
4) Substituted or unsubstituted —$C_2$-$C_8$ alkynyl;
5) Substituted or unsubstituted arylalkyl; and
6) Substituted or unsubstituted aryl;
preferably $R_2$ is hydrogen or methyl.
m is selected from 0, 1, 2 and 3, preferably m is 0, 1 or 2.
$R_3$ is hydrogen, hydroxyl, —OSO$_3$H, —OSO$_3^-$, —OAc, —OPO$_3$H$_2$ or —OPO$_3^{2-}$, preferably $R_3$ is hydrogen or hydroxyl.
$R_4$ is hydrogen, halogen, CN, N$_3$, hydroxyl, —OSO$_3$H, —OSO$_3^-$, —OAc, —OPO$_3$H$_2$, —OPO$_3^{2-}$, —SR$_2$ or —NHR$_2$, wherein, R$_2$ is as defined previously; preferably R$_4$ is hydrogen.
Or $R_3$ and $R_4$ are taken together with the carbon atoms to which they are attached to form —CH=CH— or a cycloalkyl ring or heterocycloalkyl ring such as, but not limited to cyclopropyl, or epoxide.
$R_5$ and $R_6$ are independently selected from hydrogen or hydroxyl protecting group such as, but not limited to acetyl, trimethyl silyl, or benzyl; preferably $R_5$ and $R_6$ are hydrogen. $R_7$ is selected from the group consisting of:
1) Hydrogen;
2) Halogen;
3) Substituted or unsubstituted —$C_1$-$C_8$ alkyl;
4) Substituted or unsubstituted —$C_2$-$C_8$ alkenyl;
5) Substituted or unsubstituted —$C_2$-$C_8$ alkynyl; and
6) Substituted or unsubstituted —$C_3$-$C_8$ cycloalkyl;
preferably $R_7$ is $C_1$-$C_4$-alkyl, more preferably $R_7$ is ethyl;
$R_{10}$ and $R_{11}$ are each independently selected from hydrogen, substituted or unsubstituted —$C_1$-$C_8$ alkyl, substituted or unsubstituted —$C_2$-$C_8$ alkenyl, substituted or unsubstituted —$C_2$-$C_8$ alkynyl, substituted or unsubstituted —$C_3$-$C_8$ cycloalkyl, substituted or unsubstituted heterocycloalkyl, or $R_{10}$ and $R_{11}$ are taken together with the nitrogen atom they attached to form a heterocyclic ring; preferably, $R_{11}$ is hydrogen.

In another embodiment, the present invention provides a pharmaceutical composition comprising a therapeutically effective amount of a compound or combination of compounds of the present invention, or a pharmaceutically acceptable salt form, stereoisomer, solvate, hydrate or combination thereof, in combination with a pharmaceutically acceptable carrier or excipient.

In another embodiment, the present invention provides a method for the prevention or treatment of an FXR mediated disease or condition. The method comprises administering a therapeutically effective amount of a compound of the invention. The present invention also provides the use of a compound of the invention for the preparation of a medicament for the prevention or treatment of an FXR mediated disease or condition.

In yet another embodiment, the present invention provides a method for the prevention or treatment of a TGR5 mediated disease or condition. The method comprises administering a therapeutically effective amount of a compound of the invention. The present invention also provides the use of a compound of the invention for the preparation of a medicament for the prevention or treatment of a TGR5 mediated disease or condition.

In certain embodiments, a disease that involves modulation of the TGR5 receptor is selected from metabolic disease, inflammatory disease, liver disease, autoimmune disease, cardiac disease, kidney disease, cancer, and gastrointestinal disease.

DETAILED DESCRIPTION OF THE INVENTION

A first embodiment of the invention is a compound represented by Formula I as described above, or a pharmaceutically acceptable salt, hydrate, solvate, ester or prodrug thereof. In preferred compounds of Formula I, $R_2$, $R_3$, $R_4$, $R_5$, and $R_6$ are each hydrogen and $R_7$ is ethyl.

In one embodiment, the invention provides compounds of Formula I',

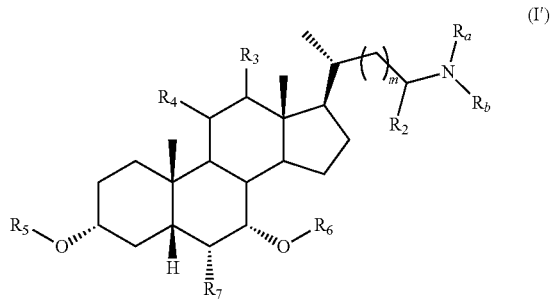

or a pharmaceutically acceptable salt or prodrug thereof, wherein:
$R_a$ is hydrogen;
$R_b$ is —C(O)NHSO$_2$R$_1$;
$R_1$ is selected from the group consisting of:
1) Halogen;
2) Hydroxyl;
3) Substituted or unsubstituted —$C_1$-$C_8$ alkyl;
4) Substituted or unsubstituted —$C_2$-$C_8$ alkenyl;
5) Substituted or unsubstituted —$C_2$-$C_8$ alkynyl;
6) Substituted or unsubstituted —$C_3$-$C_8$ cycloalkyl;
7) Substituted or unsubstituted aryl;
8) Substituted or unsubstituted alkylaryl;
9) Substituted or unsubstituted heterocycloalkyl;
10) Substituted or unsubstituted heteroaryl;
11) Substituted or unsubstituted alkylheteroaryl; and
12) —NR$_{10}$R$_{11}$;
$R_2$ is selected from the group consisting of:
1) Hydrogen;
2) Substituted or unsubstituted —$C_1$-$C_8$ alkyl;

3) Substituted or unsubstituted —$C_2$-$C_8$ alkenyl;

4) Substituted or unsubstituted —$C_2$-$C_8$ alkynyl;

5) Substituted or unsubstituted alkylaryl; and

6) Substituted or unsubstituted aryl;

Preferably $R_2$ is hydrogen or methyl;

m is selected from 0, 1, 2 and 3, preferably m is from 0, 1 or 2.

$R_3$ is hydrogen, hydroxyl, —$OSO_3H$, —$OSO_3^-$, —OAc, —$OPO_3H_2$ or —$OPO_3^{2-}$, preferably $R_3$ is hydrogen or hydroxyl.

$R_4$ is hydrogen, halogen, CN, $N_3$, hydroxyl, —$OSO_3H$, —$OSO_3^-$, —OAc, —$OPO_3H_2$, —$OPO_3^{2-}$, —$SR_2$ or —$NHR_2$, wherein, $R_2$ is as defined previously; preferably $R_4$ is hydrogen.

Or $R_3$ and $R_4$ are taken together with the carbon atoms they attached form —CH=CH— or a cycloalkyl ring or heterocycloalkyl ring such as, but not limited to cyclopropyl, or epoxide.

$R_5$ and $R_6$ are independently selected from hydrogen or hydroxyl protecting group such as, but not limited to acetyl, trimethylsilyl, or benzyl; preferably $R_5$ and $R_6$ are hydrogen.

$R_7$ is selected from the group consisting of:

1) Hydrogen;

2) Halogen;

3) Substituted or unsubstituted —$C_1$-$C_8$ alkyl;

4) Substituted or unsubstituted —$C_2$-$C_8$ alkenyl;

5) Substituted or unsubstituted —$C_2$-$C_8$ alkynyl; and

6) Substituted or unsubstituted —$C_3$-$C_8$ cycloalkyl;

preferably $R_7$ is $C_1$-$C_4$-alkyl, more preferably $R_7$ is ethyl;

$R_{10}$ and $R_{11}$ are each independently selected from hydrogen, substituted or unsubstituted —$C_1$-$C_8$ alkyl, substituted or unsubstituted —$C_2$-$C_8$ alkenyl, Substituted or unsubstituted —$C_2$-$C_8$ alkynyl, substituted or unsubstituted —$C_3$-$C_8$ cycloalkyl, or $R_{10}$ and $R_{11}$, taken together with the nitrogen atom to which they are attached, form a heterocyclic ring; preferably $R_{11}$ is hydrogen.

In preferred embodiments, the compounds of the invention have the stereochemistry set forth in Formula IA:

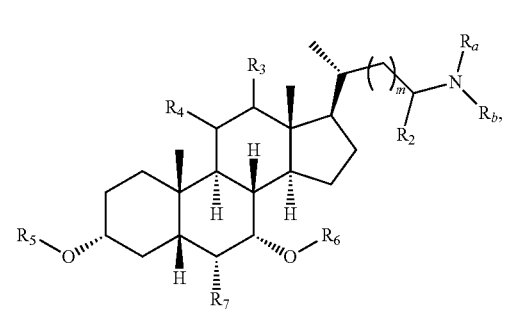

(IA)

where m, $R_a$, $R_b$, $R_2$, $R_3$, $R_4$, $R_5$, $R_6$, and $R_7$ have the meanings given for these variables in Formula I or Formula I'.

A second embodiment of the invention is a compound represented by Formula II or a pharmaceutically acceptable salt, hydrate, solvate, ester or prodrug thereof:

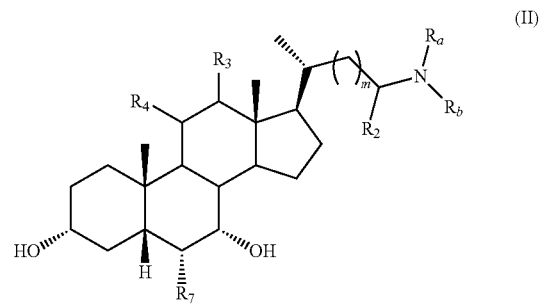

(II)

wherein $R_a$, $R_b$, $R_2$, $R_3$, $R_4$, $R_7$ and m are as previously defined in Formula I or I'.

A third embodiment of the invention is a compound represented by Formula III or a pharmaceutically acceptable salt, hydrate, solvate, ester or prodrug thereof:

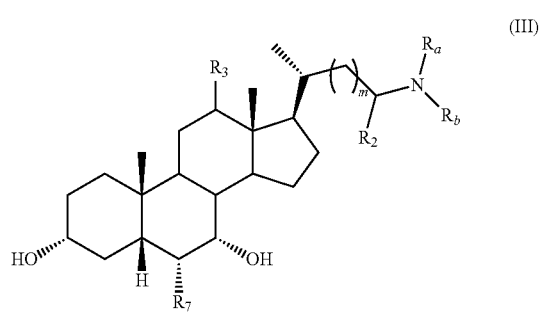

(III)

wherein $R_a$, $R_b$, $R_2$, $R_3$, $R_7$ and m are as previously defined in Formula I or I'.

Illustrative structures of Formula (III) can be represented, but not limited, by formula (III-1~III-54), where $R_1$, $R_7$, $R_{10}$ and m are as previously defined in Formula I or

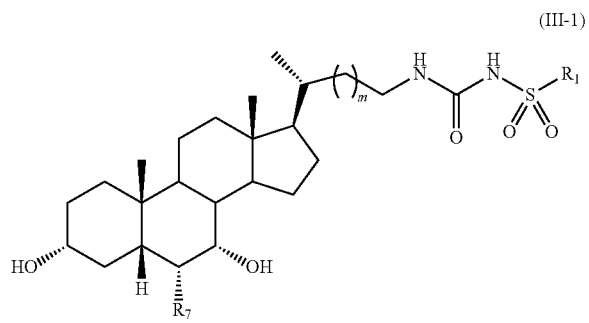

(III-1)

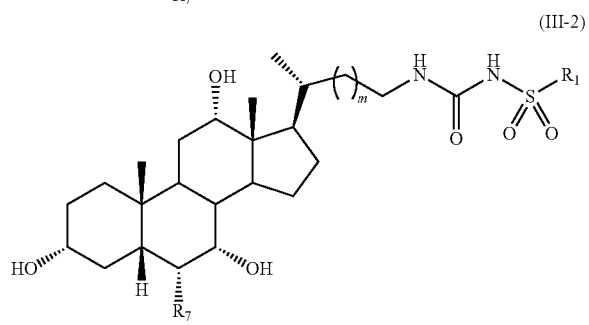

(III-2)

(III-3)
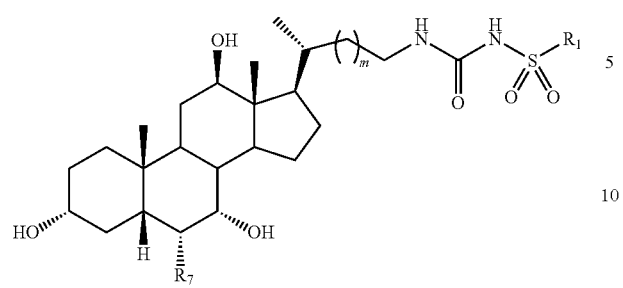
(III-4)
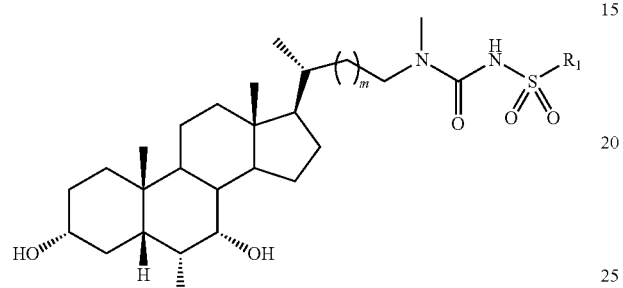
(III-5)
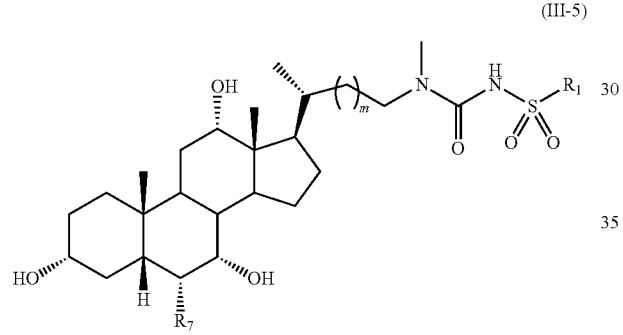
(III-6)
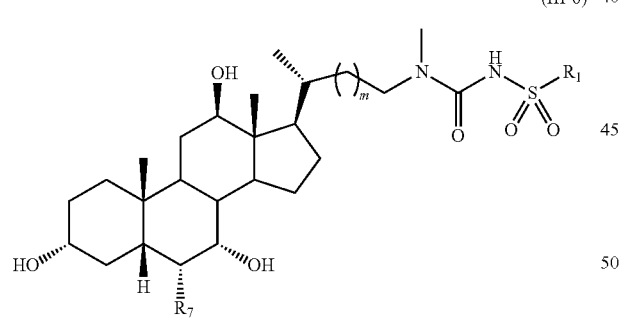
(III-7)
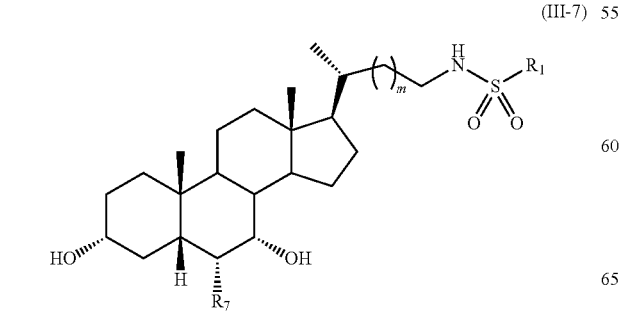
(III-8)
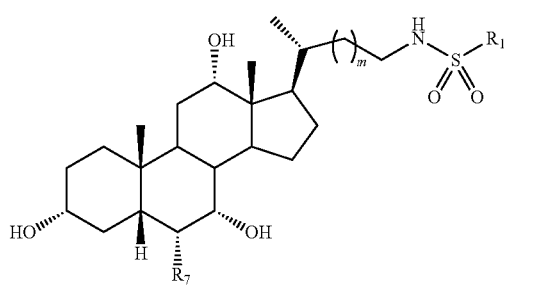
(III-9)
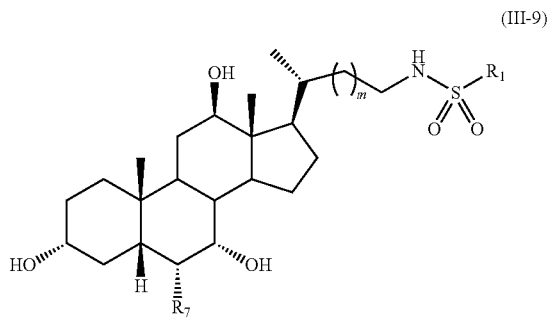
(III-10)
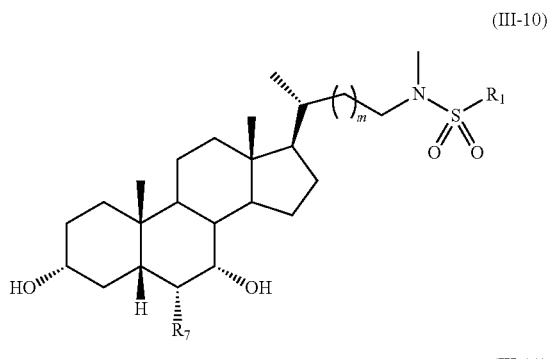
(III-11)
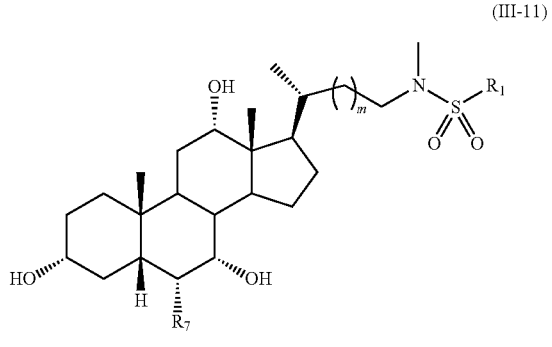
(III-12)
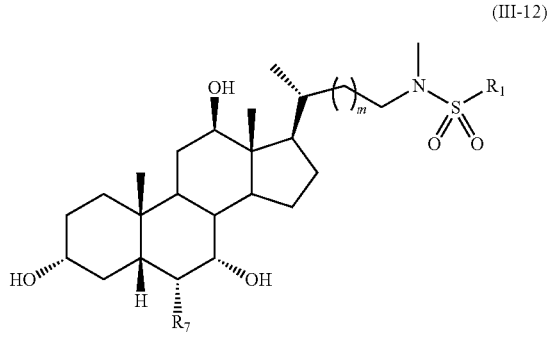

-continued
(III-13)
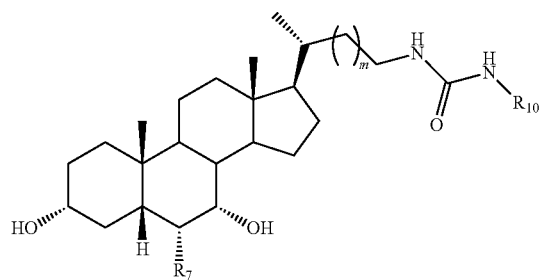
(III-14)
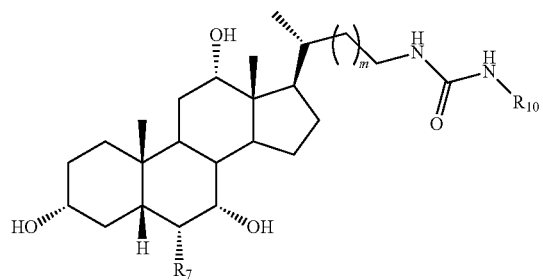
(III-15)
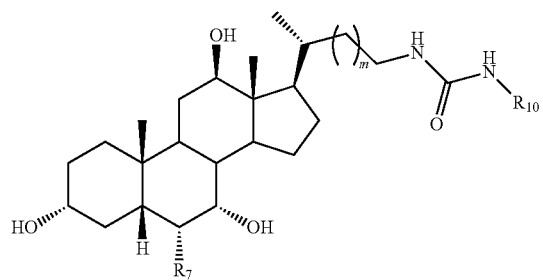
(III-16)
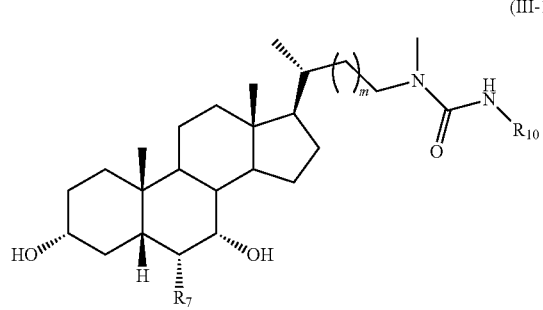
(III-17)
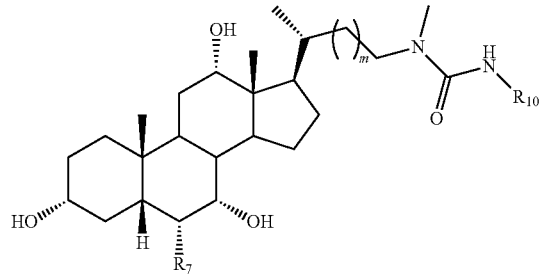
(III-18)
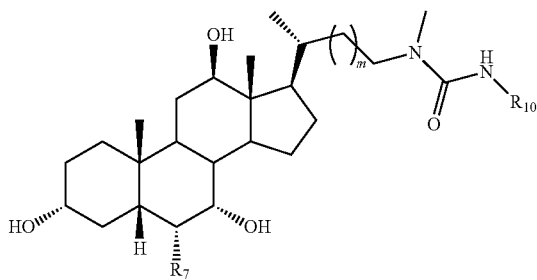
(III-19)
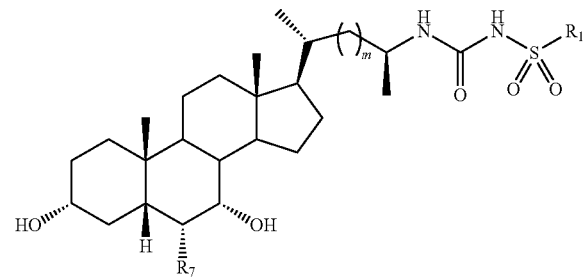
(III-20)
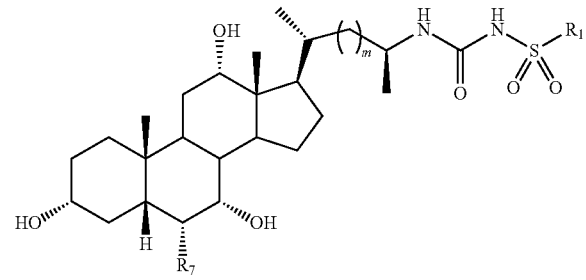
(III-21)
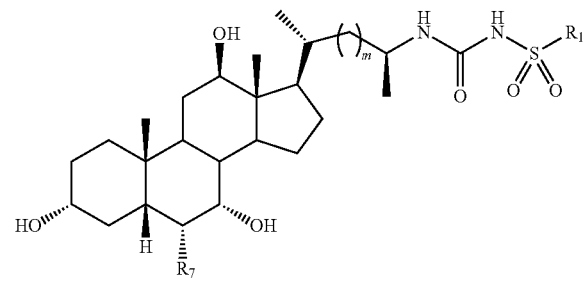
(III-22)
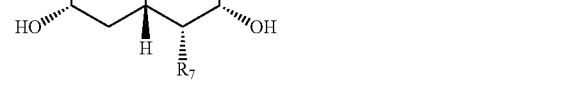

-continued
(III-23)
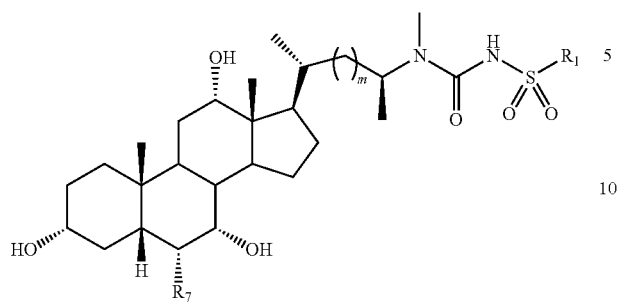
(III-24)
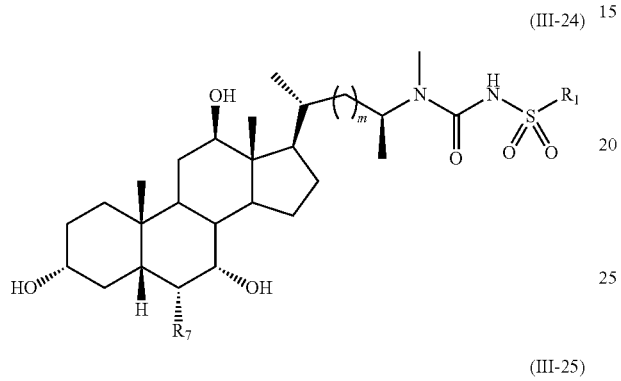
(III-25)
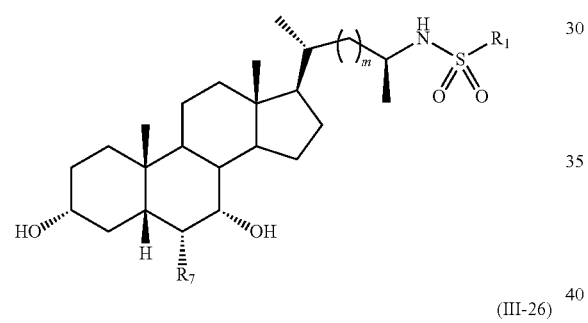
(III-26)
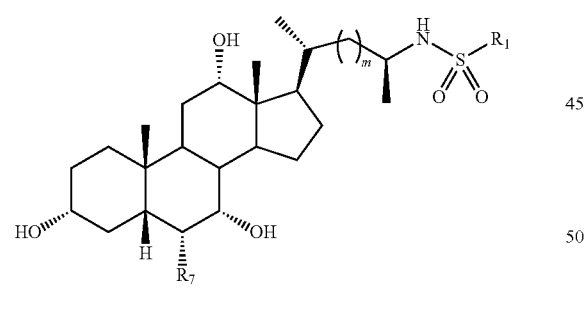
(III-27)
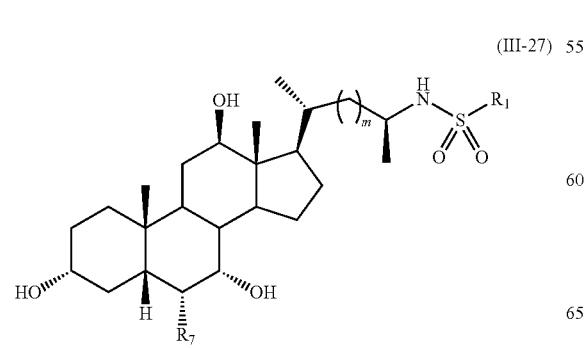
-continued
(III-28)
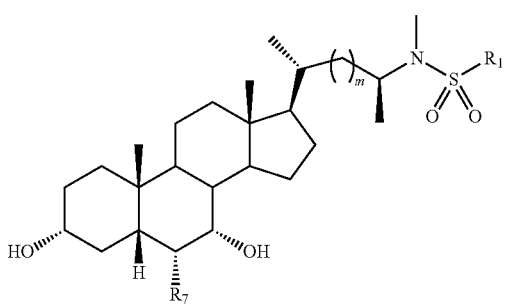
(III-29)
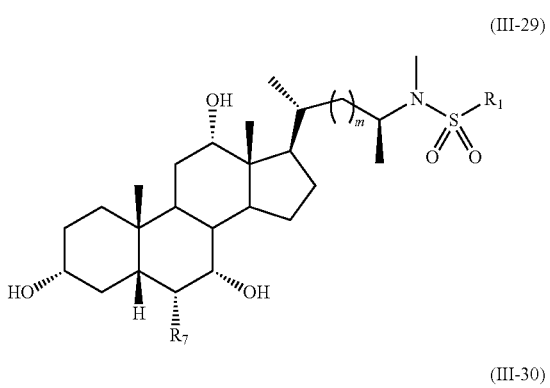
(III-30)
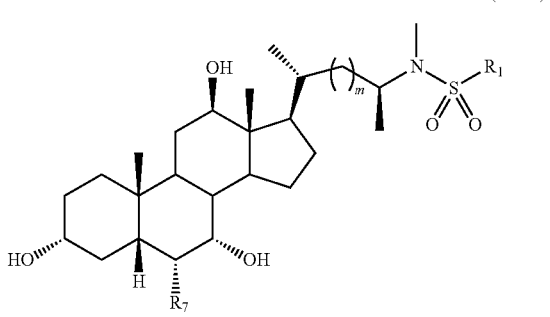
(III-31)
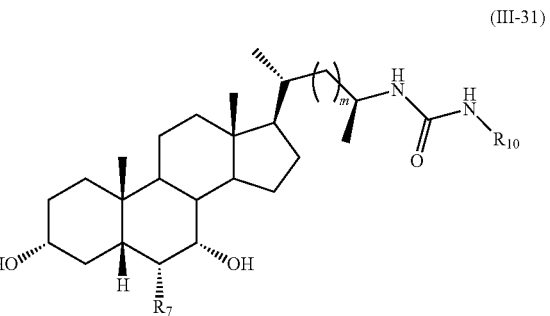
(III-32)
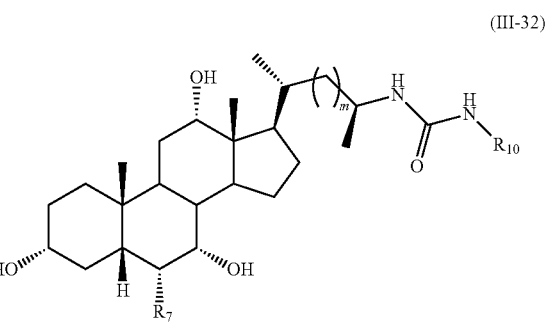

-continued
(III-33)
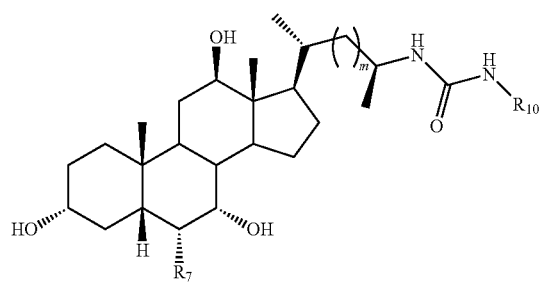
(III-34)
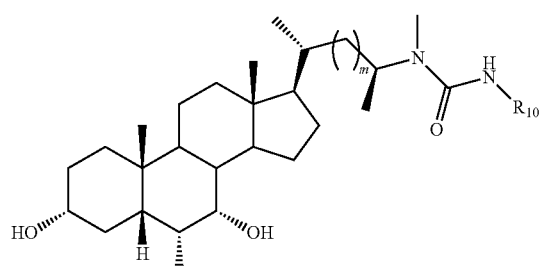
(III-35)
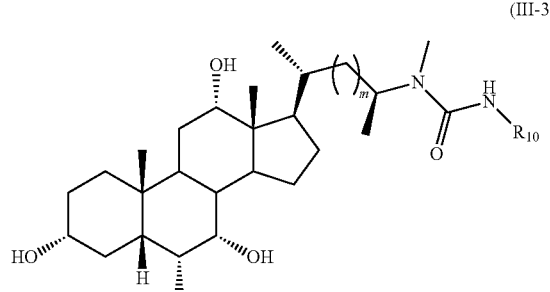
(III-36)
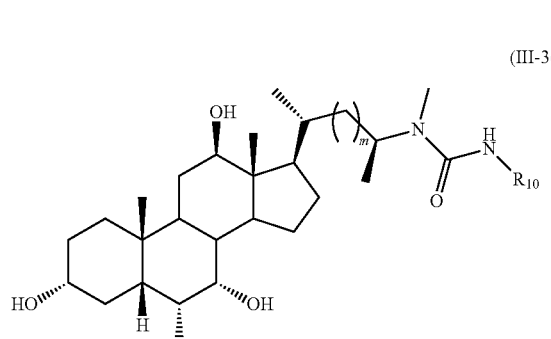
(III-37)
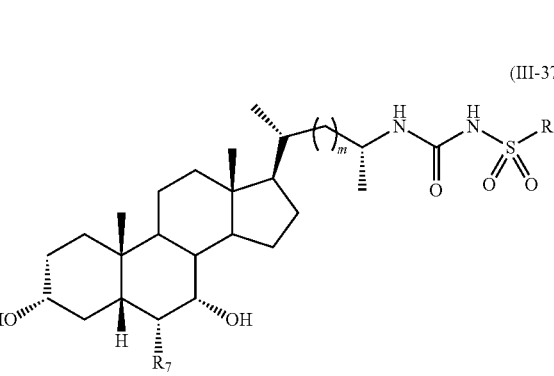
-continued
(III-38)
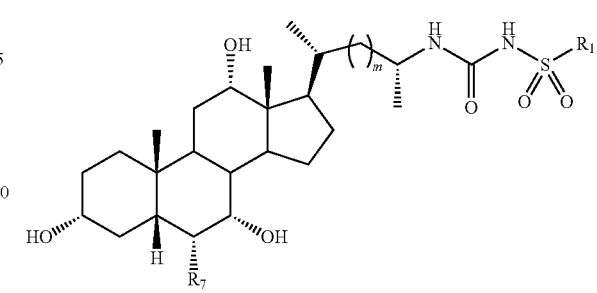
(III-39)
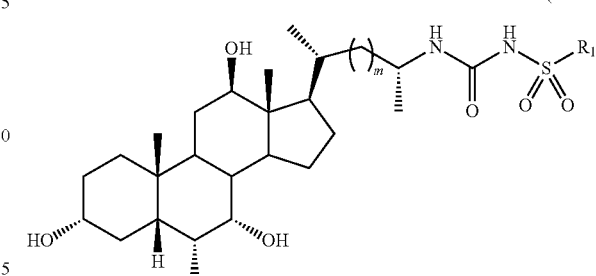
(III-40)
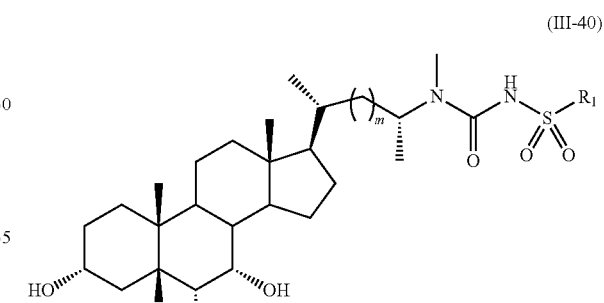
(III-41)
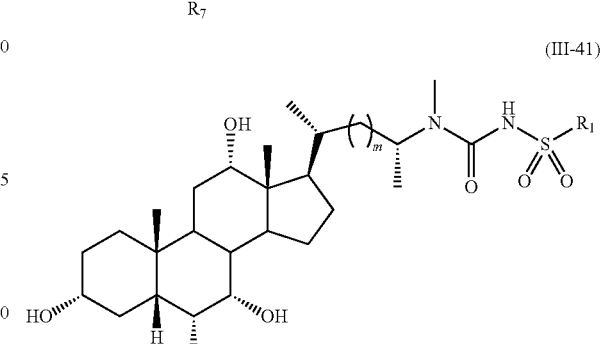
(III-42)
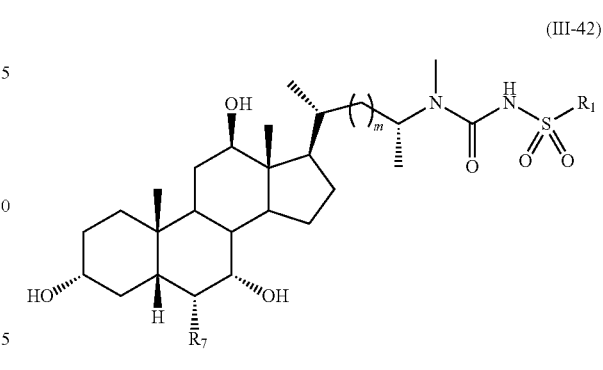

(III-43)
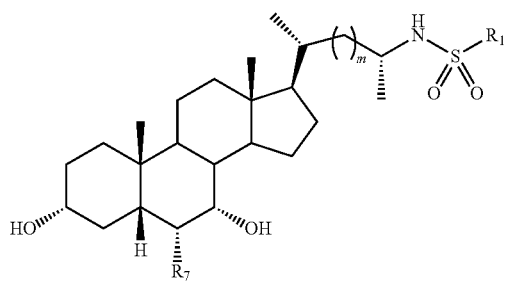
(III-44)
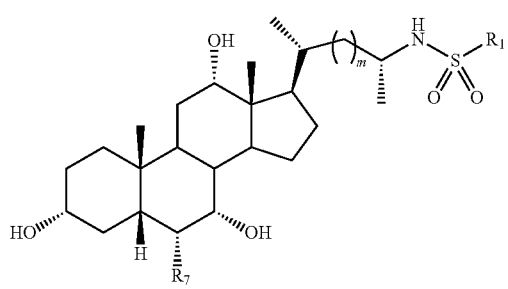
(III-45)
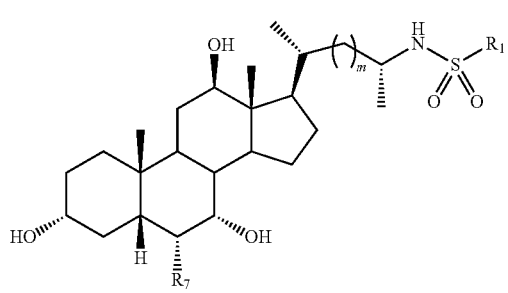
(III-46)
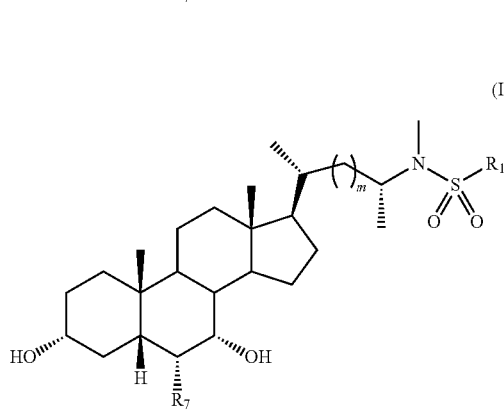
(III-47)
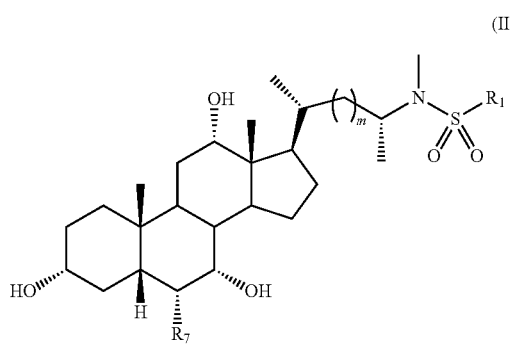
(III-48)
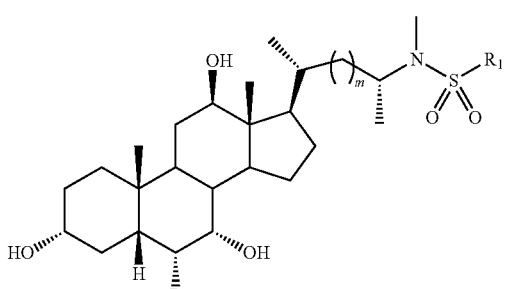
(III-49)
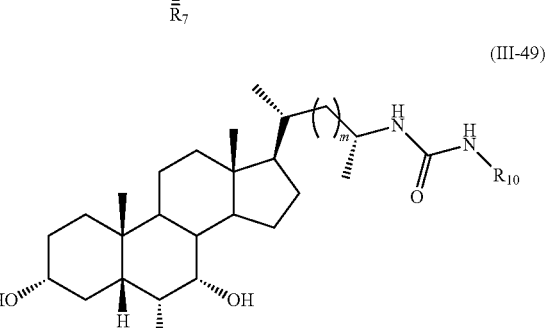
(III-50)
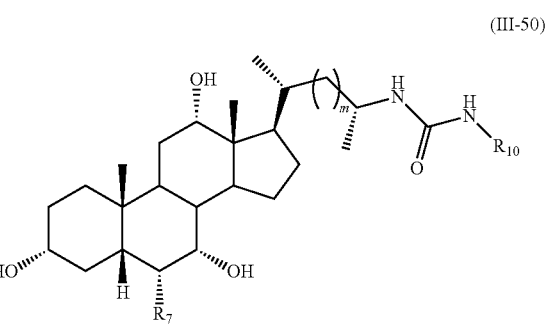
(III-51)
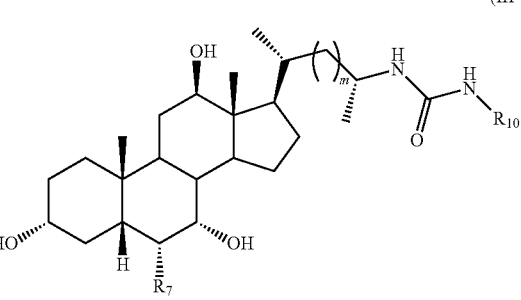
(III-52)
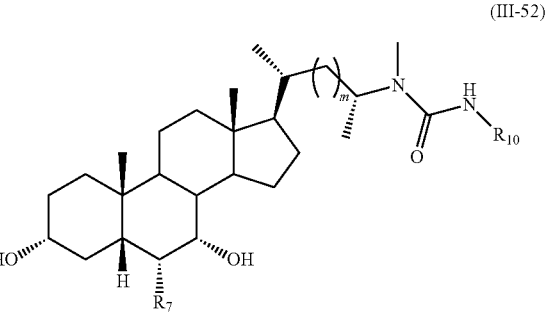

-continued (III-53)

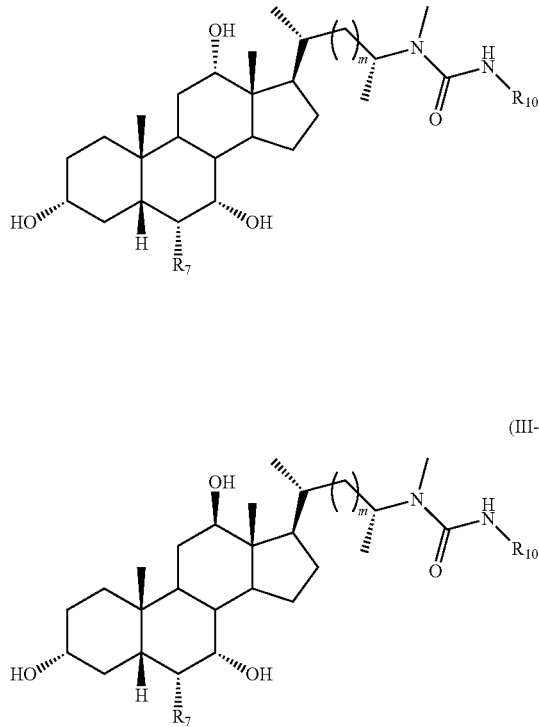

(III-54)

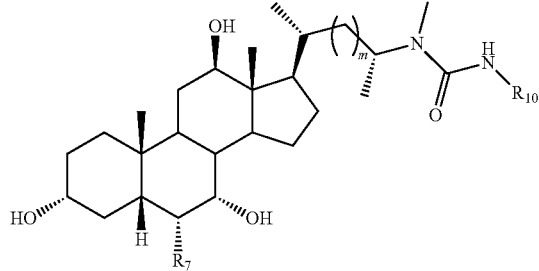

A fourth embodiment of the invention is a compound represented by Formula IV-A, IV-B, IV-C, or IV-D or a pharmaceutically acceptable salt, solvate, hydrate, ester or prodrug thereof, -continued

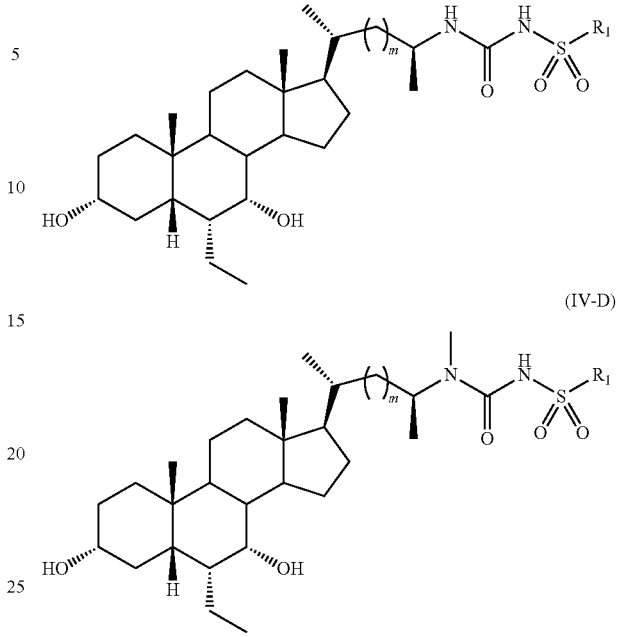

wherein $R_1$ and m are as previously defined in Formula I or I'.

In certain embodiments of the compounds of the invention, $R_1$ is $C_1$-$C_4$-alkyl, halogenated $C_1$-$C_4$-alkyl, $C_1$-$C_4$-alkenyl, phenyl-$C_1$-$C_4$-alkyl, substituted or unsubstituted $C_3$-$C_6$-cycloalkyl, $C_1$-$C_6$-cycloalkyl-$C_1$-$C_4$-alkyl, 5- or 6-membered heterocycloalkyl, amino, substituted or unsubstituted phenyl or halogen.

In certain embodiments of the compounds of the invention, $R_1$ is ethyl, butyl, t-butyl, propyl, benzyl, vinyl, allyl, $CF_3$,

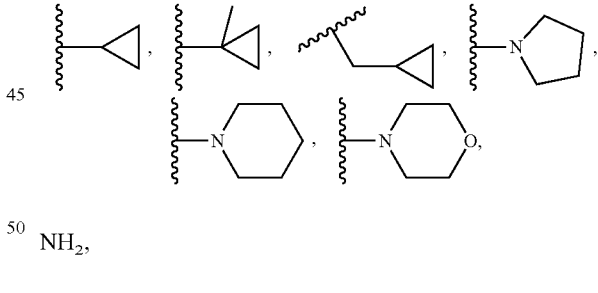

$NH_2$,

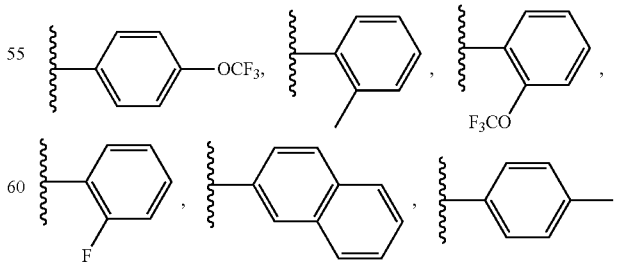

or fluoro; or $R_1$ is methyl, isopropyl or phenyl. In certain embodiments of the compounds of the invention, $R_1$ is dimethylamino or p-tert-butylphenyl.

In certain embodiments of the invention, $R_1$ is selected from the groups set forth in the table below:
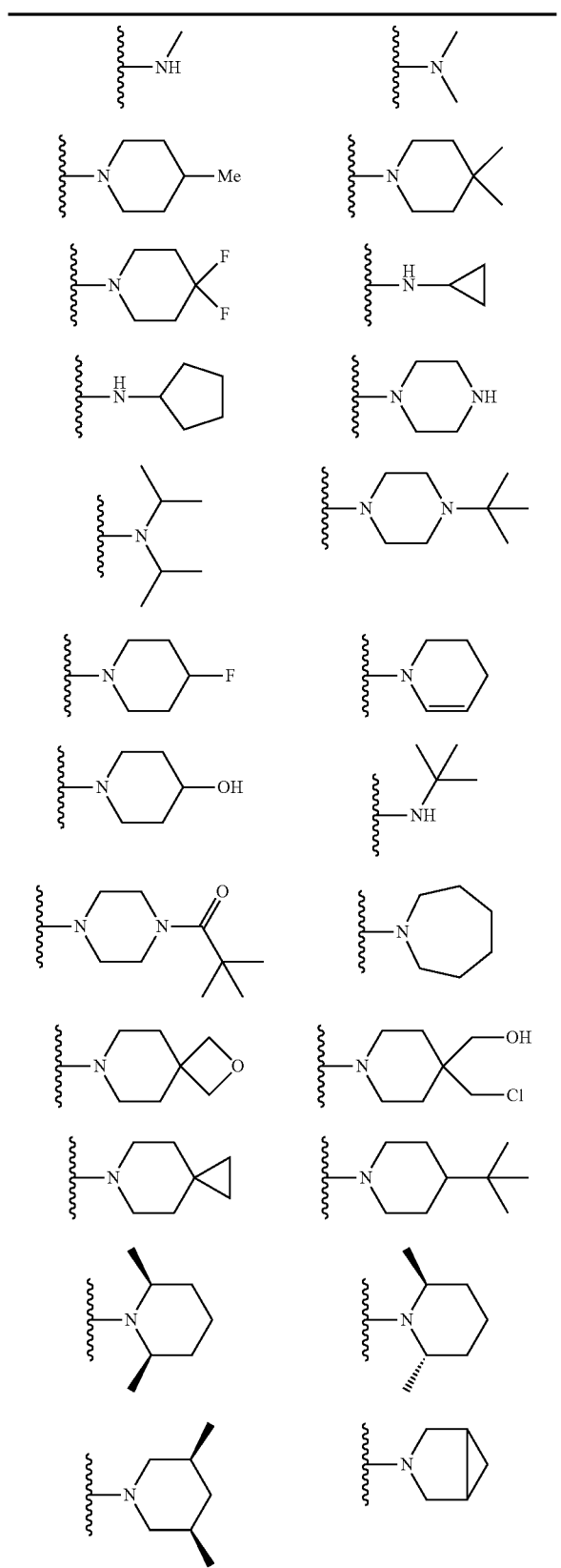
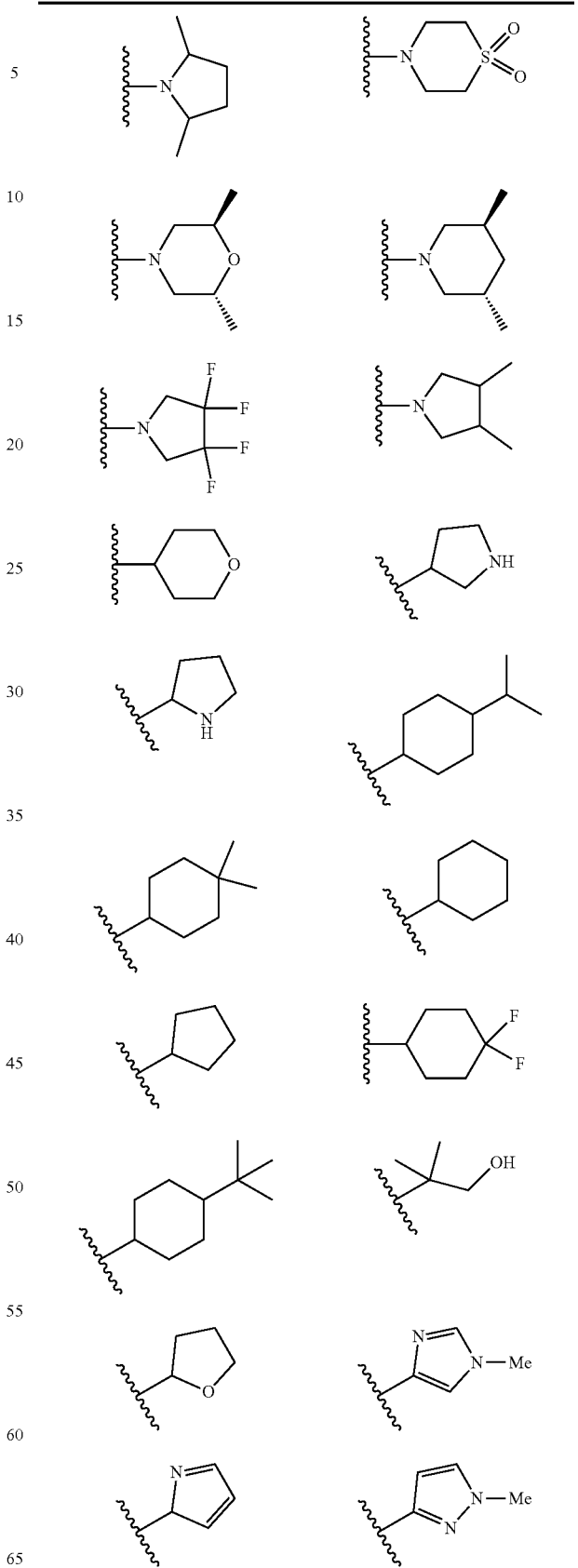

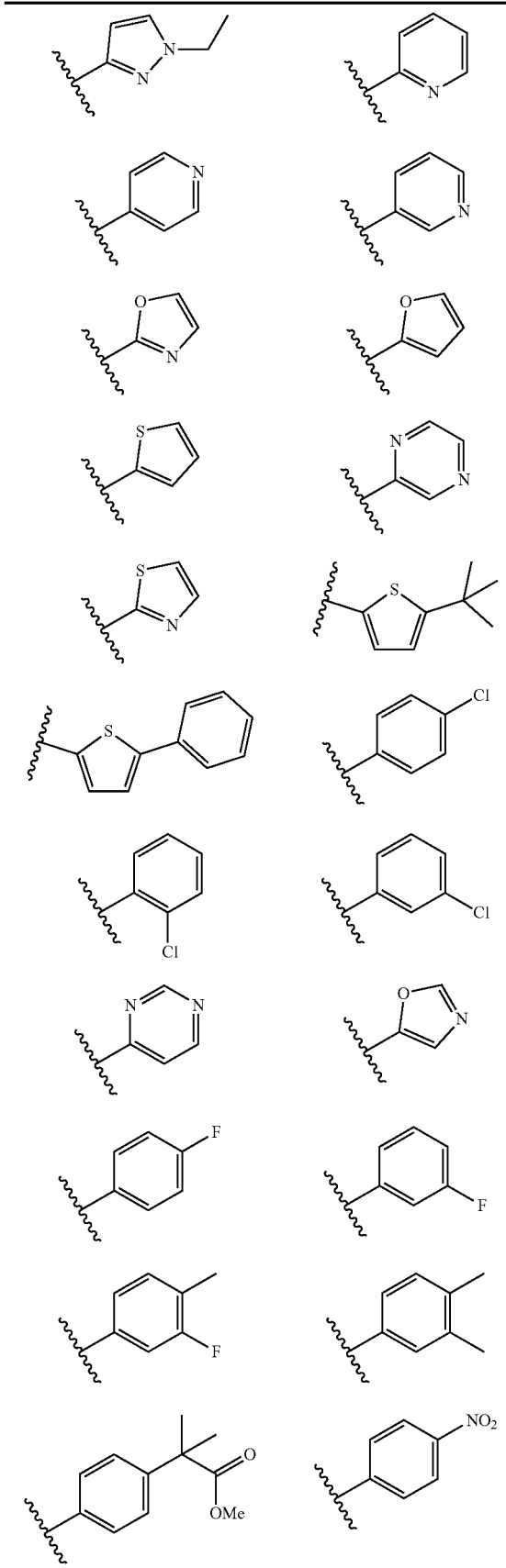
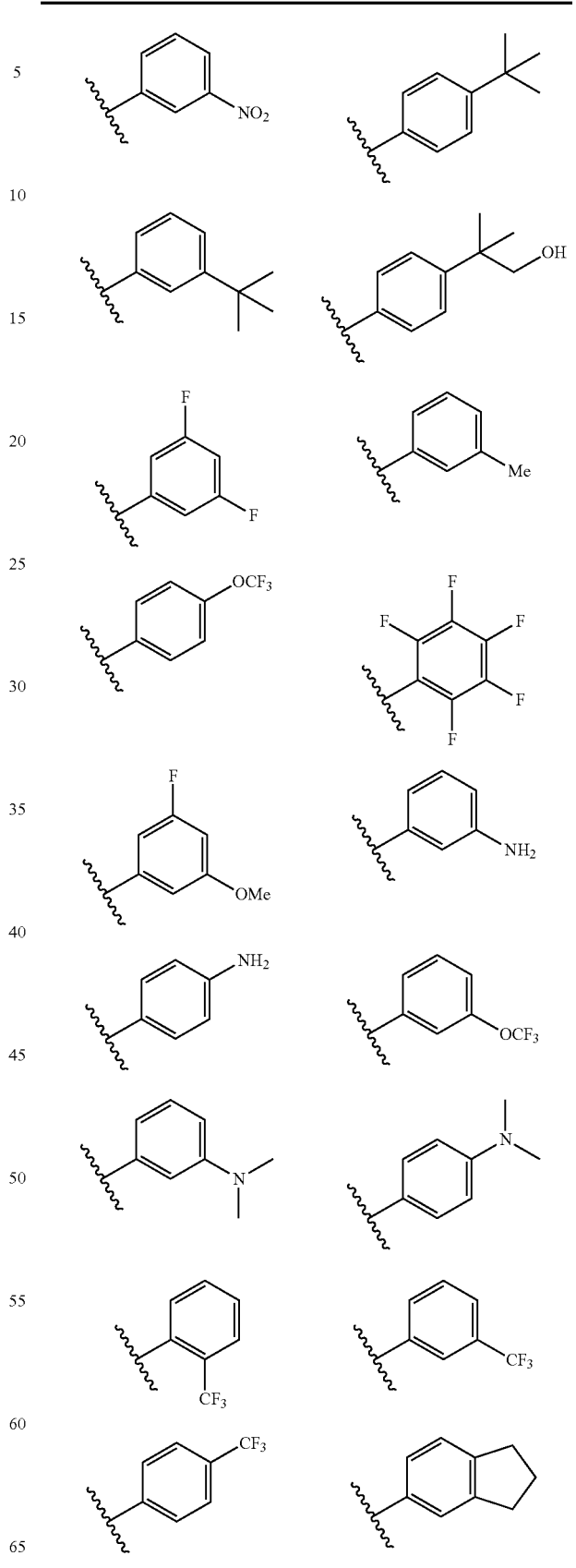

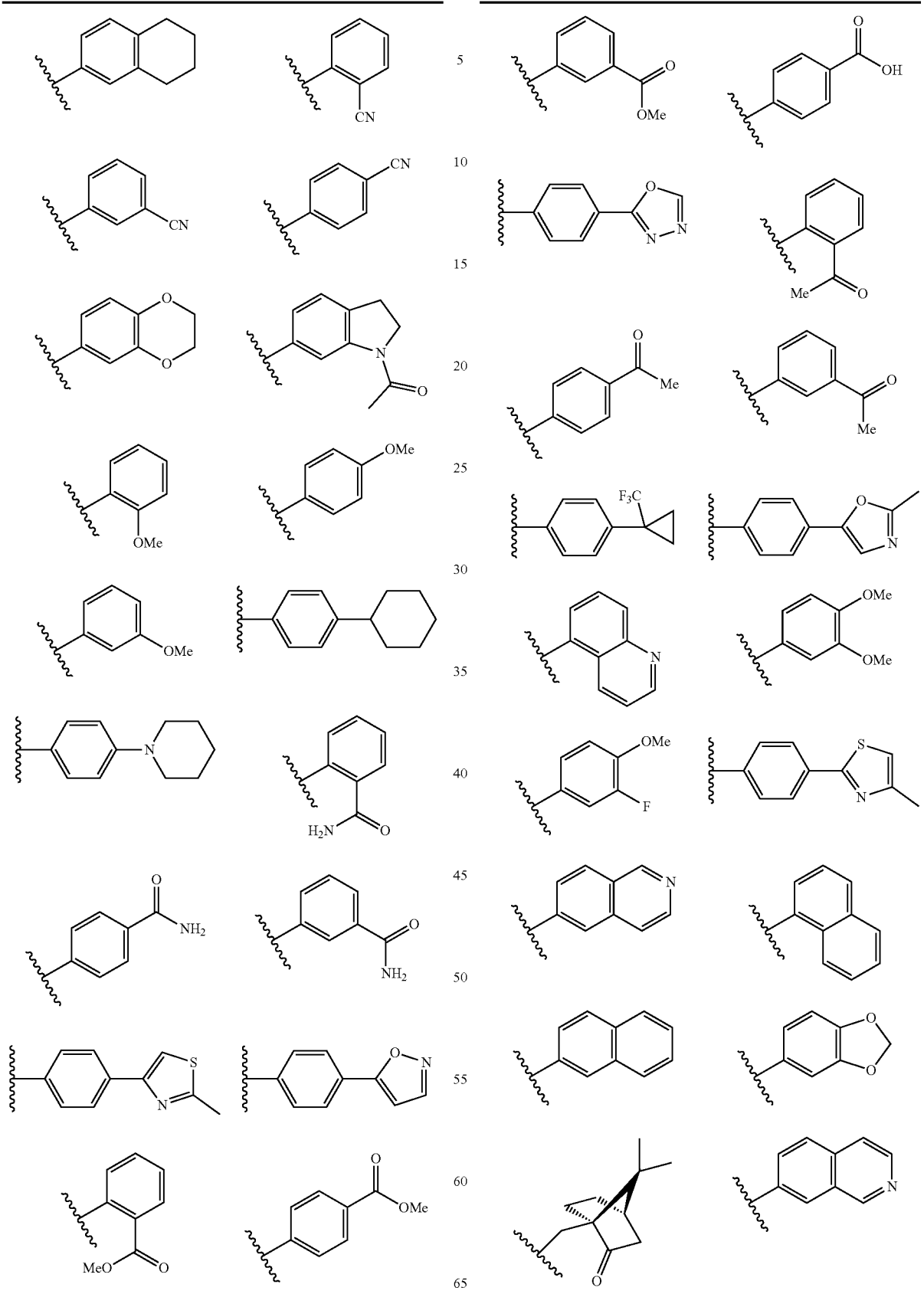

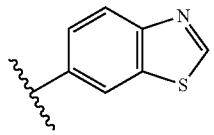 [SMILES: *c1ccc2ncsc2c1] 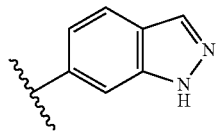 [SMILES: *c1ccc2cn[nH]c2c1]

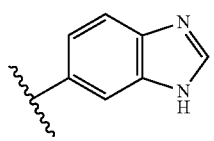 [SMILES: *c1ccc2nc[nH]c2c1] 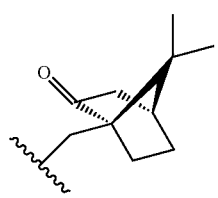

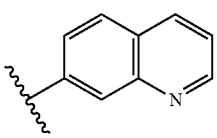 [SMILES: *c1ccc2cccnc2c1] 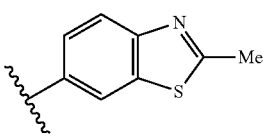 [SMILES: *c1ccc2nc(C)sc2c1]

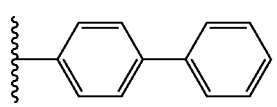 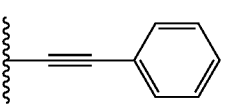

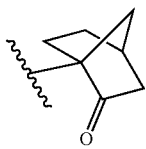 [SMILES: *C12CCC(CC1=O)C2] 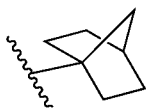 [SMILES: *C12CCC(CC1)C2]

In certain embodiments of the compounds of the invention, $R_{11}$ is hydrogen and $R_{10}$ is hydrogen, $C_1$-$C_4$-alkyl, halogenated $C_1$-$C_4$-alkyl, $C_1$-$C_4$-alkenyl, phenyl-$C_1$-$C_4$-alkyl, substituted or unsubstituted $C_3$-$C_6$-cycloalkyl, $C_1$-$C_6$-cycloalkyl-$C_1$-$C_4$-alkyl, 5- or 6-membered heterocycloalkyl, or substituted or unsubstituted phenyl.

In certain embodiments of the compounds of the invention, $R_{11}$ is hydrogen and $R_{10}$ is hydrogen, methyl, ethyl, isopropyl, butyl, t-butyl, propyl, benzyl, vinyl, allyl, $CF_3$,

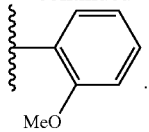

Representative compounds of the invention include, but are not limited to, the following compounds (compounds 1 to 75 in Table 1) according to Formula IV-A, wherein, $R_1$ and m are delineated for each compound in Table 1.

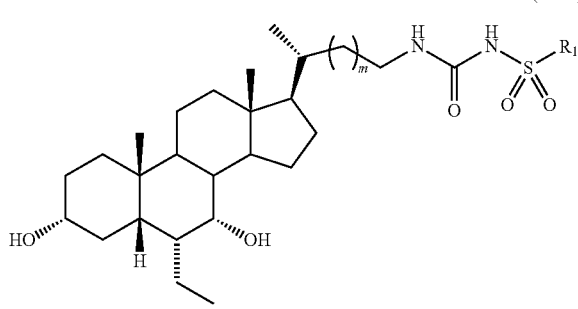

(IV-A)

TABLE 1

| Compound | m | $R_1$ |
|---|---|---|
| 1 | 0 | Methyl |
| 2 | 0 | Ethyl |
| 3 | 0 | Isopropyl |
| 4 | 0 | Butyl |
| 5 | 0 | t-Butyl |
| 6 | 0 | Propyl |
| 7 | 0 | Benzyl |
| 8 | 0 | Vinyl |
| 9 | 0 | Allyl |
| 10 | 0 | $CF_3$ |
| 11 | 0 |  |
| 12 | 0 |  |
| 13 | 0 |  |
| 14 | 0 |  |
| 15 | 0 |  |
| 16 | 0 |  |

TABLE 1-continued
| Compound | m | R₁ |
|---|---|---|
| 17 | 0 | NH₂ |
| 18 | 0 | 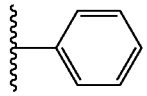 |
| 19 | 0 | 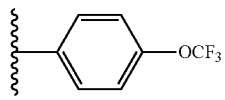 |
| 20 | 0 | 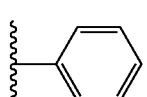 |
| 21 | 0 | 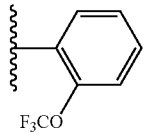 |
| 22 | 0 | 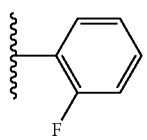 [SMILES: *c1ccccc1F] |
| 23 | 0 | 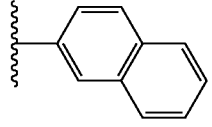 [SMILES: *c1ccc2ccccc2c1] |
| 24 | 0 | 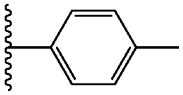 |
| 25 | 0 | F |
| 26 | 1 | Methyl |
| 27 | 1 | Ethyl |
| 28 | 1 | Isopropyl |
| 29 | 1 | Butyl |
| 30 | 1 | t-Butyl |
| 31 | 1 | Propyl |
| 32 | 1 | Benzyl |
| 33 | 1 | Vinyl |
| 34 | 1 | Allyl |
| 35 | 1 | CF₃ |
| 36 | 1 |  |
| 37 | 1 |  |
| 38 | 1 |  |
| 39 | 1 | 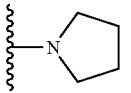 |
| 40 | 1 | 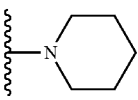 |
| 41 | 1 | 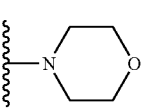 |
| 42 | 1 | NH₂ |
| 43 | 1 | 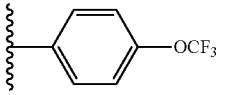 |
| 44 | 1 | 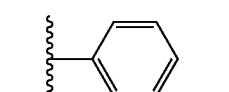 |
| 45 | 1 | 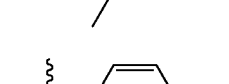 |
| 46 | 1 | 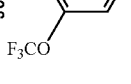 |
| 47 | 1 | 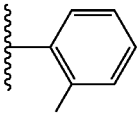 |
| 48 | 1 | 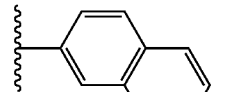 |
| 49 | 1 |  |
| 50 | 1 | F |
| 51 | 2 | Methyl |
| 52 | 2 | Ethyl |
| 53 | 2 | Isopropyl |
| 54 | 2 | Butyl |
| 55 | 2 | t-Butyl |
| 56 | 2 | Propyl |
| 57 | 2 | Benzyl |
| 58 | 2 | Vinyl |
| 59 | 2 | Allyl |
| 60 | 2 | CF₃ |

TABLE 1-continued
| Compound | m | R₁ |
|---|---|---|
| 61 | 2 |  |
| 62 | 2 |  |
| 63 | 2 | 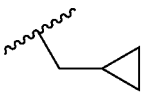 [SMILES: *CC1CC1] |
| 64 | 2 | 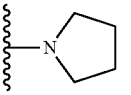 |
| 65 | 2 | 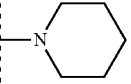 |
| 66 | 2 | 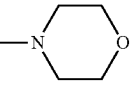 |
| 67 | 2 | NH₂ |
| 68 | 2 | 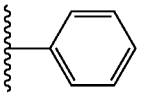 [SMILES: *c1ccccc1] |
| 69 | 2 | 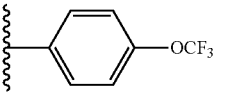 [SMILES: *c1ccc(OC(F)(F)F)cc1] |
| 70 | 2 | 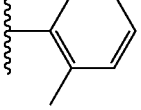 |
| 71 | 2 | 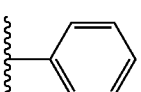 |
| 72 | 2 | 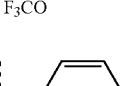 |
| 73 | 2 | 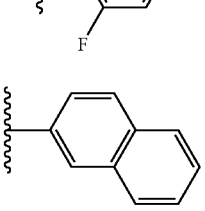 |
| 74 | 2 |  |
| 75 | 2 | F |
Representative compounds of the invention include, but are not limited to, the following compounds (compounds 76 to 150 in Table 2) according to Formula IV-B, wherein, R₁ and m are delineated for each compound in Table 2.
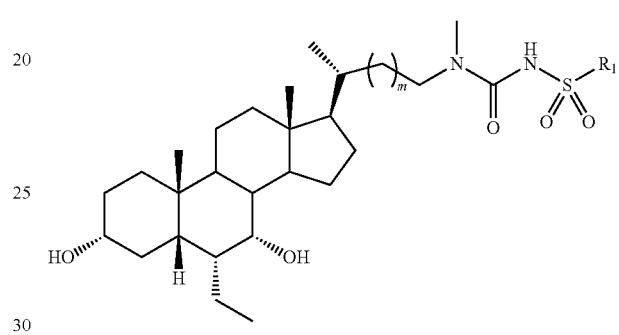
(IV-B)
TABLE 2
| Compound | m | R₁ |
|---|---|---|
| 76 | 0 | Methyl |
| 77 | 0 | Ethyl |
| 78 | 0 | Isopropyl |
| 79 | 0 | Butyl |
| 80 | 0 | t-Butyl |
| 81 | 0 | Propyl |
| 82 | 0 | Benzyl |
| 83 | 0 | Vinyl |
| 84 | 0 | Allyl |
| 85 | 0 | CF₃ |
| 86 | 0 |  |
| 87 | 0 |  |
| 88 | 0 |  |
| 89 | 0 |  |
| 90 | 0 |  |

TABLE 2-continued
| Compound | m | R₁ |
|---|---|---|
| 91 | 0 | 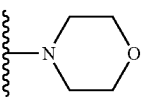 |
| 92 | 0 | NH₂ |
| 93 | 0 | 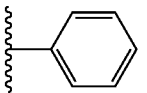 [SMILES: *c1ccccc1] |
| 94 | 0 | 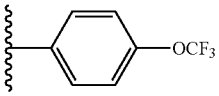 |
| 95 | 0 | 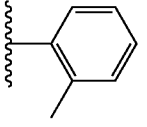 [SMILES: *c1ccccc1C] |
| 96 | 0 | 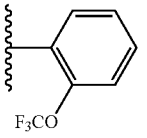 |
| 97 | 0 | 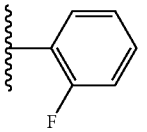 [SMILES: *c1ccccc1F] |
| 98 | 0 | 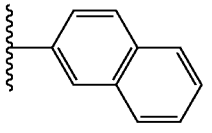 [SMILES: *c1ccc2ccccc2c1] |
| 99 | 0 | 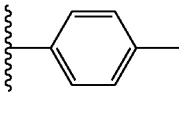 [SMILES: *c1ccc(C)cc1] |
| 100 | 0 | F |
| 101 | 1 | Methyl |
| 102 | 1 | Ethyl |
| 103 | 1 | Isopropyl |
| 104 | 1 | Butyl |
| 105 | 1 | t-Butyl |
| 106 | 1 | Propyl |
| 107 | 1 | Benzyl |
| 108 | 1 | Vinyl |
| 109 | 1 | Allyl |
| 110 | 1 | CF₃ |
| 111 | 1 |  |
| 112 | 1 |  |
TABLE 2-continued
| Compound | m | R₁ |
|---|---|---|
| 113 | 1 | 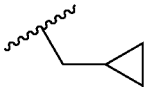 [SMILES: *CC1CC1] |
| 114 | 1 | 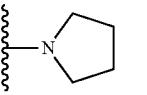 |
| 115 | 1 |  |
| 116 | 1 | 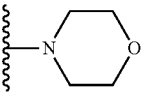 |
| 117 | 1 | NH₂ |
| 118 | 1 | 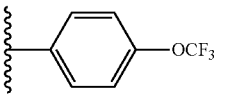 |
| 119 | 1 | 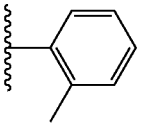 [SMILES: *c1ccccc1C] |
| 120 | 1 | 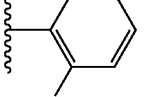 |
| 121 | 1 | 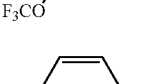 |
| 122 | 1 | 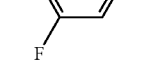 |
| 123 | 1 | 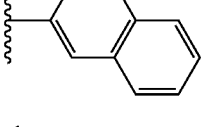 |
| 124 | 1 | 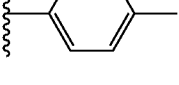 |
| 125 | 1 | F |
| 126 | 2 | Methyl |
| 127 | 2 | Ethyl |
| 128 | 2 | Isopropyl |
| 129 | 2 | Butyl |
| 130 | 2 | t-Butyl |
| 131 | 2 | Propyl |
| 132 | 2 | Benzyl |
| 133 | 2 | Vinyl |

TABLE 2-continued

| Compound | m | R₁ |
|---|---|---|
| 134 | 2 | Allyl |
| 135 | 2 | CF₃ |
| 136 | 2 | (cyclopropyl) |
| 137 | 2 | (1-methylcyclopropyl) |
| 138 | 2 | (cyclopropylmethyl) |
| 139 | 2 | (pyrrolidin-1-yl) |
| 140 | 2 | (piperidin-1-yl) |
| 141 | 2 | (morpholin-4-yl) |
| 142 | 2 | NH₂ |
| 143 | 2 | (phenyl) |
| 144 | 2 | (4-OCF₃-phenyl) |
| 145 | 2 | (2-methylphenyl) |
| 146 | 2 | (2-OCF₃-phenyl) |
| 147 | 2 | (2-fluorophenyl) |
| 148 | 2 | (naphthalen-2-yl) |
| 149 | 2 | (4-methylphenyl) |
| 150 | 2 | F |

A fifth embodiment of the invention is a compound represented by Formula V-A and V-B or a pharmaceutically acceptable salt, solvate, hydrate, ester or prodrug thereof.

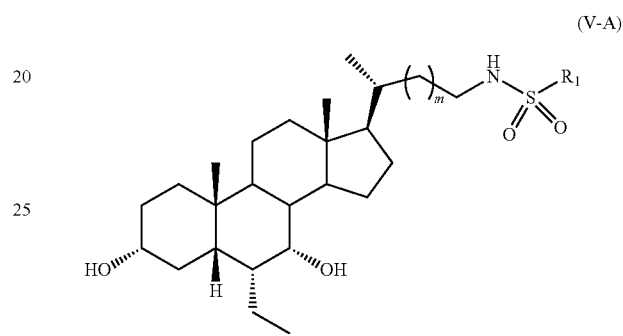

(V-A)

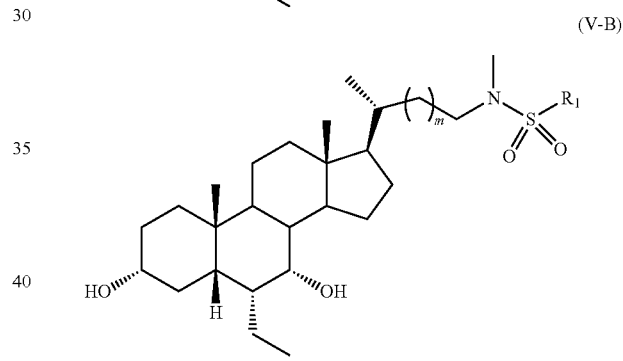

(V-B)

wherein $R_1$ and m are as previously defined in Formula I or I'.

Representative compounds of the invention include, but are not limited to, the following compounds (compounds 151 to 225 in Table 3) according to Formula V-A, wherein, $R_1$ and m are delineated for each compound in Table 3.

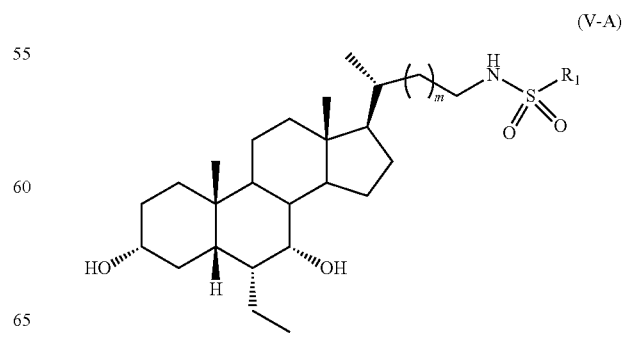

(V-A)

TABLE 3

| Compound | m | R₁ |
|---|---|---|
| 151 | 0 | Methyl |
| 152 | 0 | Ethyl |
| 153 | 0 | Isopropyl |
| 154 | 0 | Butyl |
| 155 | 0 | t-Butyl |
| 156 | 0 | Propyl |
| 157 | 0 | Benzyl |
| 158 | 0 | Vinyl |
| 159 | 0 | Allyl |
| 160 | 0 | CF₃ |
| 161 | 0 | cyclopropyl |
| 162 | 0 | 1-methylcyclopropyl |
| 163 | 0 | cyclopropylmethyl |
| 164 | 0 | pyrrolidinyl |
| 165 | 0 | piperidinyl |
| 166 | 0 | morpholinyl |
| 167 | 0 | NH₂ |
| 168 | 0 | phenyl |
| 169 | 0 | 4-OCF₃-phenyl |
| 170 | 0 | 2-methylphenyl |
| 171 | 0 | 2-OCF₃-phenyl |
| 172 | 0 | 2-F-phenyl |
| 173 | 0 | 2-naphthyl |
| 174 | 0 | 4-methylphenyl |
| 175 | 0 | F |
| 176 | 1 | Methyl |
| 177 | 1 | Ethyl |
| 178 | 1 | Isopropyl |
| 179 | 1 | Butyl |
| 180 | 1 | t-Butyl |
| 181 | 1 | Propyl |
| 182 | 1 | Benzyl |
| 183 | 1 | Vinyl |
| 184 | 1 | Allyl |
| 185 | 1 | CF₃ |
| 186 | 1 | cyclopropyl |
| 187 | 1 | 1-methylcyclopropyl |
| 188 | 1 | cyclopropylmethyl |
| 189 | 1 | pyrrolidinyl |
| 190 | 1 | piperidinyl |
| 191 | 1 | morpholinyl |
| 192 | 1 | NH₂ |
| 193 | 1 | phenyl |
| 194 | 1 | 4-OCF₃-phenyl |
| 195 | 1 | 2-methylphenyl |

TABLE 3-continued

| Compound | m | R₁ |
|---|---|---|
| 196 | 1 | 2-(trifluoromethoxy)phenyl |
| 197 | 1 | 2-fluorophenyl |
| 198 | 1 | isoquinolin-6-yl |
| 199 | 1 | 4-methylphenyl |
| 200 | 1 | F |
| 201 | 2 | Methyl |
| 202 | 2 | Ethyl |
| 203 | 2 | Isopropyl |
| 204 | 2 | Butyl |
| 205 | 2 | t-Butyl |
| 206 | 2 | Propyl |
| 207 | 2 | Benzyl |
| 208 | 2 | Vinyl |
| 209 | 2 | Allyl |
| 210 | 2 | CF₃ |
| 211 | 2 | cyclopropyl |
| 212 | 2 | 1-methylcyclopropyl |
| 213 | 2 | cyclopropylmethyl |
| 214 | 2 | pyrrolidin-1-yl |
| 215 | 2 | piperidin-1-yl |
| 216 | 2 | morpholin-4-yl |
| 217 | 2 | NH₂ |
| 218 | 2 | phenyl |
| 219 | 2 | 4-(trifluoromethoxy)phenyl |
| 220 | 2 | 2-methylphenyl |
| 221 | 2 | 2-(trifluoromethoxy)phenyl |
| 222 | 2 | 2-fluorophenyl |
| 223 | 2 | naphthalen-2-yl |
| 224 | 2 | 4-methylphenyl |
| 225 | 2 | F |

Representative compounds of the invention include, but are not limited to, the following compounds (compounds 226 to 300 in Table 4) according to Formula V-B, wherein, R₁ and m are delineated for each compound in Table 4.

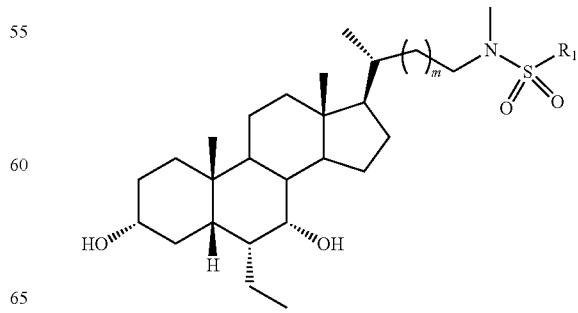

(V-B)

TABLE 4

| Compound | m | R₁ |
|---|---|---|
| 226 | 0 | Methyl |
| 227 | 0 | Ethyl |
| 228 | 0 | Isopropyl |
| 229 | 0 | Butyl |
| 230 | 0 | t-Butyl |
| 231 | 0 | Propyl |
| 232 | 0 | Benzyl |
| 233 | 0 | Vinyl |
| 234 | 0 | Allyl |
| 235 | 0 | CF₃ |
| 236 | 0 | cyclopropyl |
| 237 | 0 | 1-methylcyclopropyl |
| 238 | 0 | cyclopropylmethyl |
| 239 | 0 | pyrrolidin-1-yl |
| 240 | 0 | piperidin-1-yl |
| 241 | 0 | morpholin-4-yl |
| 242 | 0 | NH₂ |
| 243 | 0 | phenyl |
| 244 | 0 | 4-(OCF₃)phenyl |
| 245 | 0 | 2-methylphenyl |
| 246 | 0 | 2-(OCF₃)phenyl |
| 247 | 0 | 2-fluorophenyl |
| 248 | 0 | isoquinolin-3-yl |
| 249 | 0 | 4-methylphenyl |
| 250 | 0 | F |
| 251 | 1 | Methyl |
| 252 | 1 | Ethyl |
| 253 | 1 | Isopropyl |
| 254 | 1 | Butyl |
| 255 | 1 | t-Butyl |
| 256 | 1 | Propyl |
| 257 | 1 | Benzyl |
| 258 | 1 | Vinyl |
| 259 | 1 | Allyl |
| 260 | 1 | CF₃ |
| 261 | 1 | cyclopropyl |
| 262 | 1 | 1-methylcyclopropyl |
| 263 | 1 | cyclopropylmethyl |
| 264 | 1 | pyrrolidin-1-yl |
| 265 | 1 | piperidin-1-yl |
| 266 | 1 | morpholin-4-yl |
| 267 | 1 | NH₂ |
| 268 | 1 | phenyl |
| 269 | 1 | 4-(OCF₃)phenyl |
| 270 | 1 | 2-methylphenyl |

TABLE 4-continued

| Compound | m | R₁ |
|---|---|---|
| 271 | 1 | 2-(F₃CO)-phenyl |
| 272 | 1 | 2-F-phenyl |
| 273 | 1 | naphthalen-2-yl |
| 274 | 1 | 4-methylphenyl |
| 275 | 1 | F |
| 276 | 2 | Methyl |
| 277 | 2 | Ethyl |
| 278 | 2 | Isopropyl |
| 279 | 2 | Butyl |
| 280 | 2 | t-Butyl |
| 281 | 2 | Propyl |
| 282 | 2 | Benzyl |
| 283 | 2 | Vinyl |
| 284 | 2 | Allyl |
| 285 | 2 | CF₃ |
| 286 | 2 | cyclopropyl |
| 287 | 2 | cyclopropyl |
| 288 | 2 | cyclopropylmethyl |
| 289 | 2 | pyrrolidin-1-yl |
| 290 | 2 | piperidin-1-yl |
| 291 | 2 | morpholin-4-yl |
| 292 | 2 | NH₂ |
| 293 | 2 | phenyl |
| 294 | 2 | 4-(OCF₃)-phenyl |
| 295 | 2 | 2-methylphenyl |
| 296 | 2 | 2-(F₃CO)-phenyl |
| 297 | 2 | 2-F-phenyl |
| 298 | 2 | naphthalen-2-yl |
| 299 | 2 | 4-methylphenyl |
| 300 | 2 | F |

A sixth embodiment of the invention is a compound represented by Formula VI-A or VI-B or a pharmaceutically acceptable salt, solvate, hydrate, ester or prodrug thereof:

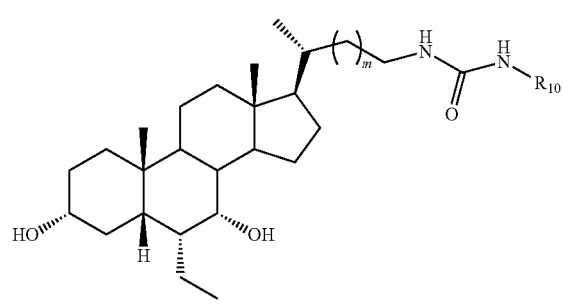

(VI-A)

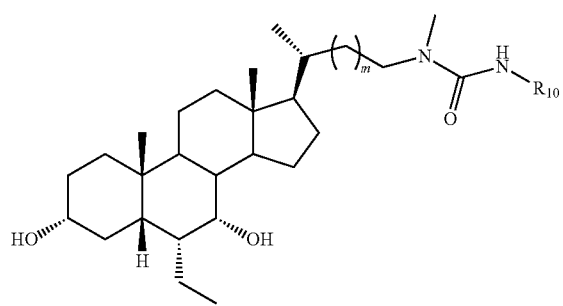

(VI-B)

wherein $R_{10}$ and m are as previously defined in Formula I or I'.

Representative compounds of the invention include, but are not limited to, the following compounds (compounds 301 to 375 in Table 5) according to Formula VI-A, wherein, $R_{10}$ and m are delineated for each compound in Table 5.

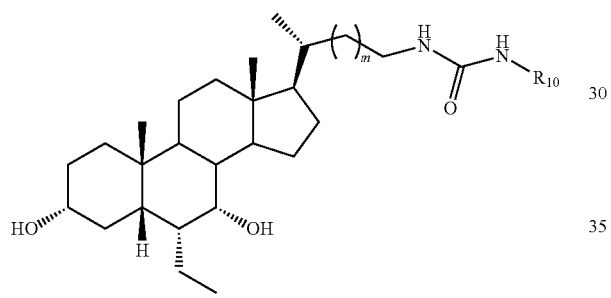

(VI-A)

TABLE 5

| Compound | m | $R_{10}$ |
|---|---|---|
| 301 | 0 | Methyl |
| 302 | 0 | Ethyl |
| 303 | 0 | Isopropyl |
| 304 | 0 | Butyl |
| 305 | 0 | t-Butyl |
| 306 | 0 | Propyl |
| 307 | 0 | Benzyl |
| 308 | 0 | Vinyl |
| 309 | 0 | Allyl |
| 310 | 0 | $CF_3$ |
| 311 | 0 | cyclopropyl |
| 312 | 0 | methylcyclopropyl |
| 313 | 0 | cyclopropylmethyl |

TABLE 5-continued

| Compound | m | $R_{10}$ |
|---|---|---|
| 314 | 0 | pyrrolidinyl |
| 315 | 0 | piperidinyl |
| 316 | 0 | morpholinyl |
| 317 | 0 | H |
| 318 | 0 | phenyl |
| 319 | 0 | 4-$OCF_3$-phenyl |
| 320 | 0 | 2-methylphenyl |
| 321 | 0 | 2-$OCF_3$-phenyl |
| 322 | 0 | 2-fluorophenyl |
| 323 | 0 | naphthyl |
| 324 | 0 | 4-methylphenyl |
| 325 | 0 | 2-methoxyphenyl |
| 326 | 1 | Methyl |
| 327 | 1 | Ethyl |
| 328 | 1 | Isopropyl |
| 329 | 1 | Butyl |
| 330 | 1 | t-Butyl |
| 331 | 1 | Propyl |
| 332 | 1 | Benzyl |
| 333 | 1 | Vinyl |

TABLE 5-continued
| Compound | m | R₁₀ |
|---|---|---|
| 334 | 1 | Allyl |
| 335 | 1 | CF₃ |
| 336 | 1 |  |
| 337 | 1 |  |
| 338 | 1 | 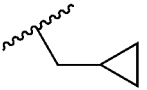 |
| 339 | 1 | 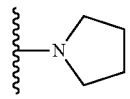 |
| 340 | 1 | 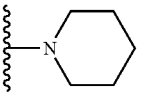 |
| 341 | 1 | 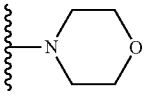 |
| 342 | 1 | H |
| 343 | 1 | 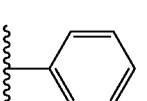 |
| 344 | 1 | 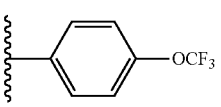 [SMILES: *c1ccc(OC(F)(F)F)cc1] |
| 345 | 1 | 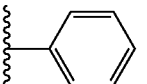 |
| 346 | 1 | 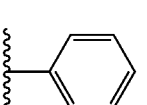 |
| 347 | 1 | 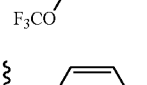 |
| 348 | 1 | 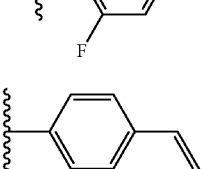 |
| 349 | 1 |  |
| 350 | 1 | 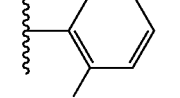 |
| 351 | 2 | Methyl |
| 352 | 2 | Ethyl |
| 353 | 2 | Isopropyl |
| 354 | 2 | Butyl |
| 355 | 2 | t-Butyl |
| 356 | 2 | Propyl |
| 357 | 2 | Benzyl |
| 358 | 2 | Vinyl |
| 359 | 2 | Allyl |
| 360 | 2 | CF₃ |
| 361 | 2 | 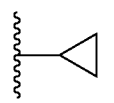 |
| 362 | 2 | 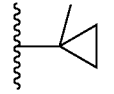 |
| 363 | 2 | 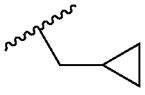 [SMILES: *CC1CC1] |
| 364 | 2 | 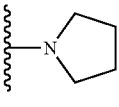 |
| 365 | 2 | 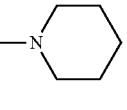 |
| 366 | 2 | 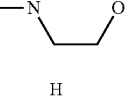 |
| 367 | 2 | H |
| 368 | 2 | 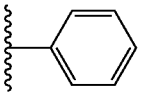 |
| 369 | 2 | 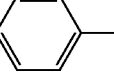 |
| 370 | 2 | 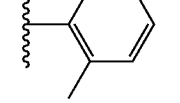 |

TABLE 5-continued

| Compound | m | R$_{10}$ |
|---|---|---|
| 371 | 2 | 2-(F$_3$CO)phenyl |
| 372 | 2 | 2-fluorophenyl |
| 373 | 2 | 2-naphthyl |
| 374 | 2 | 4-methylphenyl |
| 375 | 2 | 2-methoxyphenyl |

Representative compounds of the invention include, but are not limited to, the following compounds (compounds 376 to 450 in Table 6) according to Formula VI-B, wherein, R$_{10}$ and m are delineated for each compound in Table 6.

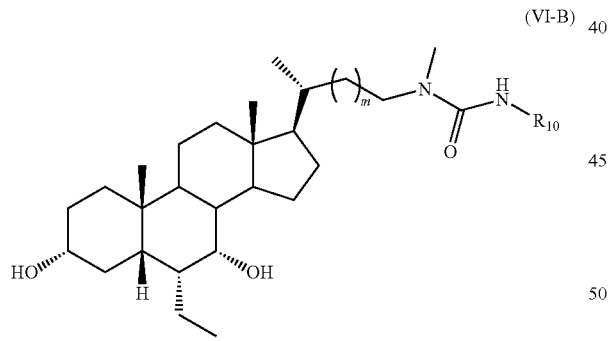

(VI-B)

TABLE 6

| Compound | m | R$_{10}$ |
|---|---|---|
| 376 | 0 | Methyl |
| 377 | 0 | Ethyl |
| 378 | 0 | Isopropyl |
| 379 | 0 | Butyl |
| 380 | 0 | t-Butyl |
| 381 | 0 | Propyl |
| 382 | 0 | Benzyl |
| 383 | 0 | Vinyl |
| 384 | 0 | Allyl |
| 385 | 0 | CF$_3$ |

TABLE 6-continued

| Compound | m | R$_{10}$ |
|---|---|---|
| 386 | 0 | cyclopropyl |
| 387 | 0 | 1-methylcyclopropyl |
| 388 | 0 | cyclopropylmethyl |
| 389 | 0 | pyrrolidin-1-yl |
| 390 | 0 | piperidin-1-yl |
| 391 | 0 | morpholin-4-yl |
| 392 | 0 | H |
| 393 | 0 | phenyl |
| 394 | 0 | 4-(OCF$_3$)phenyl |
| 395 | 0 | 2-methylphenyl |
| 396 | 0 | 2-(F$_3$CO)phenyl |
| 397 | 0 | 2-fluorophenyl |
| 398 | 0 | 2-naphthyl |
| 399 | 0 | 4-methylphenyl |

TABLE 6-continued
| Compound | m | R$_{10}$ |
|---|---|---|
| 400 | 0 | 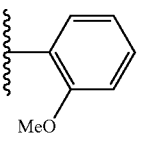 [SMILES: *c1ccccc1OC] |
| 401 | 1 | Methyl |
| 402 | 1 | Ethyl |
| 403 | 1 | Isopropyl |
| 404 | 1 | Butyl |
| 405 | 1 | t-Butyl |
| 406 | 1 | Propyl |
| 407 | 1 | Benzyl |
| 408 | 1 | Vinyl |
| 409 | 1 | Allyl |
| 410 | 1 | CF$_3$ |
| 411 | 1 |  |
| 412 | 1 |  |
| 413 | 1 | 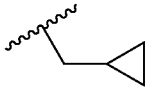 |
| 414 | 1 | 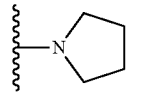 |
| 415 | 1 | 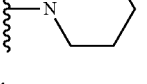 |
| 416 | 1 | 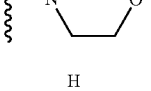 |
| 417 | 1 | H |
| 418 | 1 | 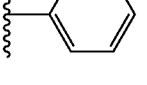 |
| 419 | 1 | 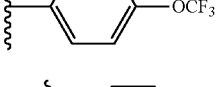 |
| 420 | 1 | 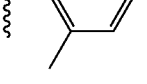 |
| 421 | 1 | 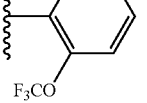 |
TABLE 6-continued
| Compound | m | R$_{10}$ |
|---|---|---|
| 422 | 1 | 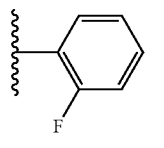 |
| 423 | 1 | 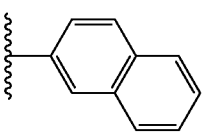 [SMILES: *c1ccc2ccccc2c1] |
| 424 | 1 | 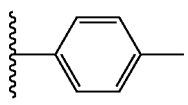 [SMILES: *c1ccc(C)cc1] |
| 425 | 1 | 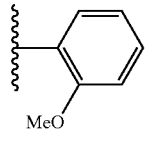 [SMILES: *c1ccccc1OC] |
| 426 | 2 | Methyl |
| 427 | 2 | Ethyl |
| 428 | 2 | Isopropyl |
| 429 | 2 | Butyl |
| 430 | 2 | t-Butyl |
| 431 | 2 | Propyl |
| 432 | 2 | Benzyl |
| 433 | 2 | Vinyl |
| 434 | 2 | Allyl |
| 435 | 2 | CF$_3$ |
| 436 | 2 | 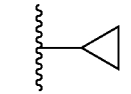 |
| 437 | 2 | 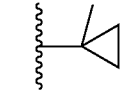 |
| 438 | 2 | 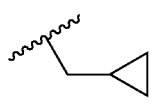 [SMILES: *CC1CC1] |
| 439 | 2 | 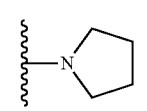 |
| 440 | 2 | 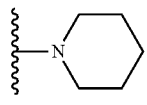 [SMILES: *N1CCCCC1] |
| 441 | 2 | 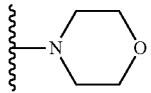 [SMILES: *N1CCOCC1] |
| 442 | 2 | H |
| 443 | 2 | 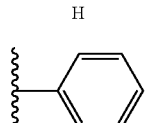 |

TABLE 6-continued

| Compound | m | R₁₀ |
|---|---|---|
| 444 | 2 | 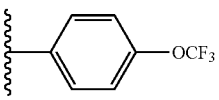 [SMILES: *c1ccc(OC(F)(F)F)cc1] 4-OCF₃-phenyl |
| 445 | 2 | 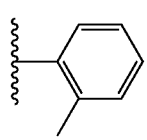 [SMILES: *c1ccccc1C] 2-methylphenyl |
| 446 | 2 | 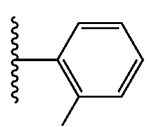 2-(F₃CO)phenyl |
| 447 | 2 | 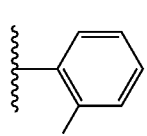 2-F-phenyl |
| 448 | 2 | 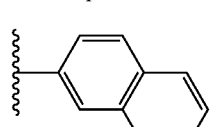 2-naphthyl |
| 449 | 2 | 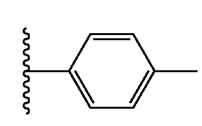 [SMILES: *c1ccc(C)cc1] 4-methylphenyl |
| 450 | 2 | 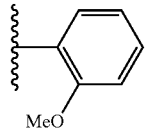 2-MeO-phenyl |

Representative compounds of the invention include, but are not limited to, the following compounds (compounds 451 to 525 in Table 7) according to Formula IV-C, wherein, R₁ and m are delineated for each compound in Table 7.

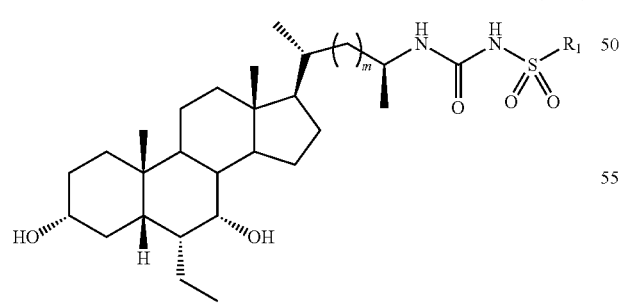

(IV-C)

TABLE 7

| Compound | m | R₁ |
|---|---|---|
| 451 | 0 | Methyl |
| 452 | 0 | Ethyl |

TABLE 7-continued

| Compound | m | R₁ |
|---|---|---|
| 453 | 0 | Isopropyl |
| 454 | 0 | Butyl |
| 455 | 0 | t-Butyl |
| 456 | 0 | Propyl |
| 457 | 0 | Benzyl |
| 458 | 0 | Vinyl |
| 459 | 0 | Allyl |
| 460 | 0 | CF₃ |
| 461 | 0 |  cyclopropyl |
| 462 | 0 |  methylcyclopropyl |
| 463 | 0 |  cyclopropylmethyl |
| 464 | 0 | 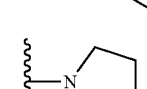 pyrrolidinyl |
| 465 | 0 | 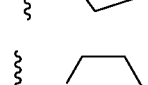 piperidinyl |
| 466 | 0 | 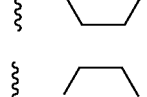 morpholinyl |
| 467 | 0 | NH₂ |
| 468 | 0 | 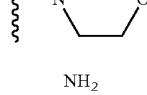 phenyl |
| 469 | 0 | 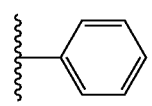 [SMILES: *c1ccccc1] 4-OCF₃-phenyl |
| 470 | 0 | 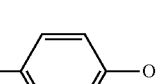 2-methylphenyl |
| 471 | 0 | 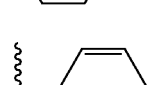 2-(F₃CO)phenyl |
| 472 | 0 | 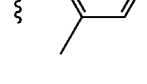 2-F-phenyl |

TABLE 7-continued

| Compound | m | R₁ |
|---|---|---|
| 473 | 0 | naphthalen-2-yl |
| 474 | 0 | 4-methylphenyl |
| 475 | 0 | F |
| 476 | 1 | Methyl |
| 477 | 1 | Ethyl |
| 478 | 1 | Isopropyl |
| 479 | 1 | Butyl |
| 480 | 1 | t-Butyl |
| 481 | 1 | Propyl |
| 482 | 1 | Benzyl |
| 483 | 1 | Vinyl |
| 484 | 1 | Allyl |
| 485 | 1 | CF₃ |
| 486 | 1 | cyclopropyl |
| 487 | 1 | 1-methylcyclopropyl |
| 488 | 1 | cyclopropylmethyl |
| 489 | 1 | pyrrolidin-1-yl |
| 490 | 1 | piperidin-1-yl |
| 491 | 1 | morpholin-4-yl |
| 492 | 1 | NH₂ |
| 493 | 1 | phenyl |
| 494 | 1 | 4-(trifluoromethoxy)phenyl |
| 495 | 1 | 2-methylphenyl |

TABLE 7-continued

| Compound | m | R₁ |
|---|---|---|
| 496 | 1 | 2-(trifluoromethoxy)phenyl |
| 497 | 1 | 2-fluorophenyl |
| 498 | 1 | naphthalen-2-yl |
| 499 | 1 | 4-methylphenyl |
| 500 | 1 | F |
| 501 | 2 | Methyl |
| 502 | 2 | Ethyl |
| 503 | 2 | Isopropyl |
| 504 | 2 | Butyl |
| 505 | 2 | t-Butyl |
| 506 | 2 | Propyl |
| 507 | 2 | Benzyl |
| 508 | 2 | Vinyl |
| 509 | 2 | Allyl |
| 510 | 2 | CF₃ |
| 511 | 2 | cyclopropyl |
| 512 | 2 | 1-methylcyclopropyl |
| 513 | 2 | cyclopropylmethyl |
| 514 | 2 | pyrrolidin-1-yl |
| 515 | 2 | piperidin-1-yl |
| 516 | 2 | morpholin-4-yl |
| 517 | 2 | NH₂ |
| 518 | 2 | phenyl |

TABLE 7-continued

| Compound | m | R₁ |
|---|---|---|
| 519 | 2 | 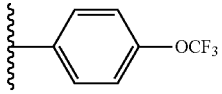 [SMILES: *c1ccc(OC(F)(F)F)cc1] 4-OCF₃-phenyl |
| 520 | 2 | 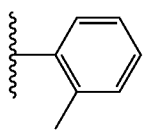 2-methylphenyl |
| 521 | 2 | 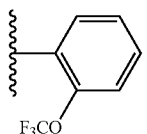 2-OCF₃-phenyl (F₃CO) |
| 522 | 2 | 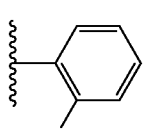 2-F-phenyl |
| 523 | 2 | 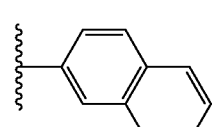 naphthyl |
| 524 | 2 | 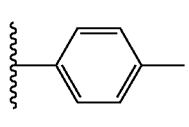 [SMILES: *c1ccc(C)cc1] 4-methylphenyl |
| 525 | 2 | F |

Representative compounds of the invention include, but are not limited to, the following compounds (compounds 526 to 600 in Table 8) according to Formula IV-D, wherein, R₁ and m are delineated for each compound in Table 8.

(IV-D)

TABLE 8

| Compound | m | R₁ |
|---|---|---|
| 526 | 0 | Methyl |
| 527 | 0 | Ethyl |
| 528 | 0 | Isopropyl |
| 529 | 0 | Butyl |

TABLE 8-continued

| Compound | m | R₁ |
|---|---|---|
| 530 | 0 | t-Butyl |
| 531 | 0 | Propyl |
| 532 | 0 | Benzyl |
| 533 | 0 | Vinyl |
| 534 | 0 | Allyl |
| 535 | 0 | CF₃ |
| 536 | 0 |  cyclopropyl |
| 537 | 0 |  methylcyclopropyl |
| 538 | 0 | 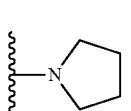 cyclopropylmethyl |
| 539 | 0 | 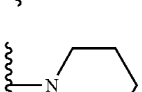 pyrrolidinyl |
| 540 | 0 | 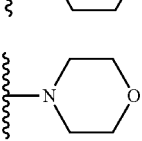 piperidinyl |
| 541 | 0 | 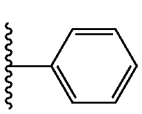 [SMILES: *c1ccccc1] morpholinyl |
| 542 | 0 | NH₂ |
| 543 | 0 | 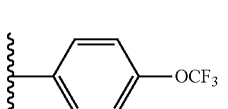 phenyl |
| 544 | 0 | 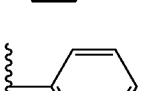 4-OCF₃-phenyl |
| 545 | 0 | 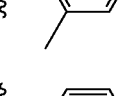 2-methylphenyl |
| 546 | 0 | 2-OCF₃-phenyl (F₃CO) |
| 547 | 0 | 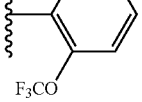 2-F-phenyl |

TABLE 8-continued

| Compound | m | R₁ |
|---|---|---|
| 548 | 0 | 2-naphthyl |
| 549 | 0 | 4-methylphenyl |
| 550 | 0 | F |
| 551 | 1 | Methyl |
| 552 | 1 | Ethyl |
| 553 | 1 | Isopropyl |
| 554 | 1 | Butyl |
| 555 | 1 | t-Butyl |
| 556 | 1 | Propyl |
| 557 | 1 | Benzyl |
| 558 | 1 | Vinyl |
| 559 | 1 | Allyl |
| 560 | 1 | CF₃ |
| 561 | 1 | cyclopropyl |
| 562 | 1 | 1-methylcyclopropyl |
| 563 | 1 | cyclopropylmethyl |
| 564 | 1 | pyrrolidin-1-yl |
| 565 | 1 | piperidin-1-yl |
| 566 | 1 | morpholin-4-yl |
| 567 | 1 | NH₂ |
| 568 | 1 | phenyl |
| 569 | 1 | 4-(OCF₃)phenyl |
| 570 | 1 | 2-methylphenyl |
| 571 | 1 | 2-(OCF₃)phenyl |
| 572 | 1 | 2-fluorophenyl |
| 573 | 1 | 2-naphthyl |
| 574 | 1 | 4-methylphenyl |
| 575 | 1 | F |
| 576 | 2 | Methyl |
| 577 | 2 | Ethyl |
| 578 | 2 | Isopropyl |
| 579 | 2 | Butyl |
| 580 | 2 | t-Butyl |
| 581 | 2 | Propyl |
| 582 | 2 | Benzyl |
| 583 | 2 | Vinyl |
| 584 | 2 | Allyl |
| 585 | 2 | CF₃ |
| 586 | 2 | cyclopropyl |
| 587 | 2 | 1-methylcyclopropyl |
| 588 | 2 | cyclopropylmethyl |
| 589 | 2 | pyrrolidin-1-yl |
| 590 | 2 | piperidin-1-yl |
| 591 | 2 | morpholin-4-yl |
| 592 | 2 | NH₂ |
| 593 | 2 | phenyl |

TABLE 8-continued

| Compound | m | $R_1$ |
|---|---|---|
| 594 | 2 | 4-OCF₃-phenyl |
| 595 | 2 | 2-methylphenyl |
| 596 | 2 | 2-OCF₃-phenyl |
| 597 | 2 | 2-fluorophenyl |
| 598 | 2 | 2-naphthyl |
| 599 | 2 | 4-methylphenyl |
| 600 | 2 | F |

A seventh embodiment of the invention is a compound represented by Formula VII-A or VII-B or a pharmaceutically acceptable salt, solvate, hydrate, ester or prodrug thereof:

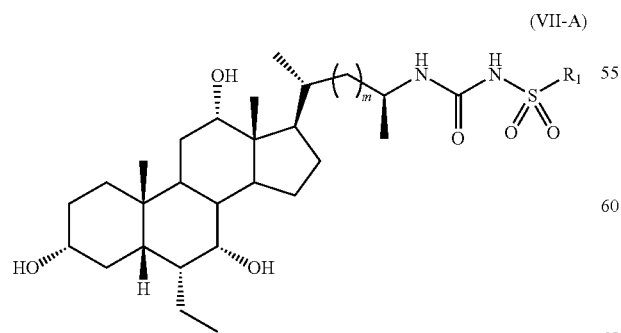

(VII-A)

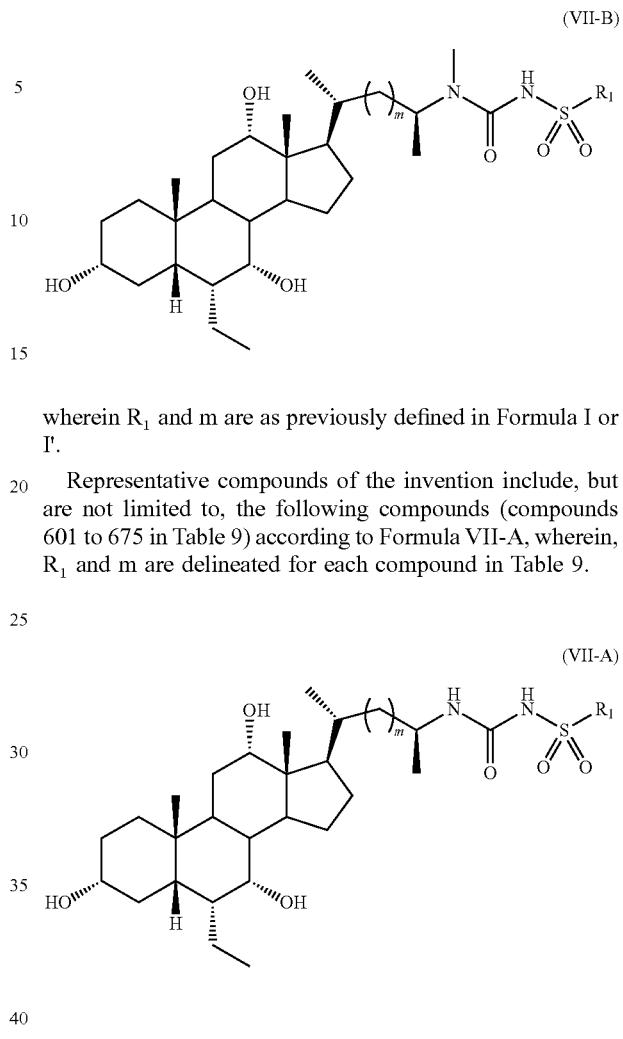

wherein $R_1$ and m are as previously defined in Formula I or I'.

Representative compounds of the invention include, but are not limited to, the following compounds (compounds 601 to 675 in Table 9) according to Formula VII-A, wherein, $R_1$ and m are delineated for each compound in Table 9.

TABLE 9

| Compound | m | $R_1$ |
|---|---|---|
| 601 | 0 | Methyl |
| 602 | 0 | Ethyl |
| 603 | 0 | Isopropyl |
| 604 | 0 | Butyl |
| 605 | 0 | t-Butyl |
| 606 | 0 | Propyl |
| 607 | 0 | Benzyl |
| 608 | 0 | Vinyl |
| 609 | 0 | Allyl |
| 610 | 0 | CF₃ |
| 611 | 0 | cyclopropyl |
| 612 | 0 | 1-methylcyclopropyl |
| 613 | 0 | cyclopropylmethyl |

TABLE 9-continued
| Compound | m | R₁ |
|---|---|---|
| 614 | 0 | 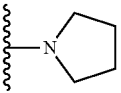 |
| 615 | 0 | 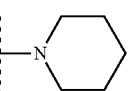 |
| 616 | 0 | 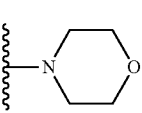 |
| 617 | 0 | $NH_2$ |
| 618 | 0 | 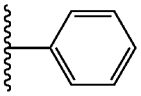 |
| 619 | 0 | 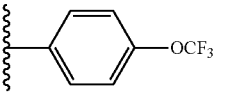 [SMILES: *c1ccc(OC(F)(F)F)cc1] |
| 620 | 0 | 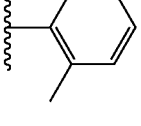 |
| 621 | 0 | 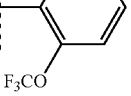 |
| 622 | 0 | 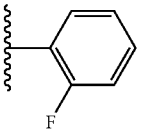 [SMILES: *c1ccccc1F] |
| 623 | 0 | 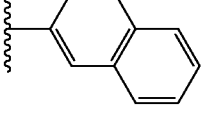 |
| 624 | 0 | 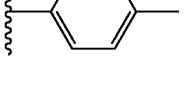 |
| 625 | 0 | F |
| 626 | 1 | Methyl |
| 627 | 1 | Ethyl |
| 628 | 1 | Isopropyl |
| 629 | 1 | Butyl |
| 630 | 1 | t-Butyl |
| 631 | 1 | Propyl |
| 632 | 1 | Benzyl |
| 633 | 1 | Vinyl |
| 634 | 1 | Allyl |
| 635 | 1 | $CF_3$ |
TABLE 9-continued
| Compound | m | R₁ |
|---|---|---|
| 636 | 1 |  |
| 637 | 1 |  |
| 638 | 1 |  |
| 639 | 1 |  |
| 640 | 1 |  |
| 641 | 1 |  |
| 642 | 1 | $NH_2$ |
| 643 | 1 |  |
| 644 | 1 | 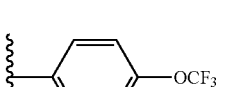 |
| 645 | 1 |  |
| 646 | 1 |  |
| 647 | 1 |  |
| 648 | 1 | 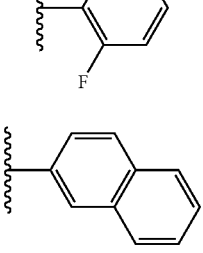 |

TABLE 9-continued

| Compound | m | R₁ |
|---|---|---|
| 649 | 1 | 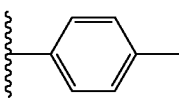 [SMILES: *c1ccc(C)cc1] |
| 650 | 1 | F |
| 651 | 2 | Methyl |
| 652 | 2 | Ethyl |
| 653 | 2 | Isopropyl |
| 654 | 2 | Butyl |
| 655 | 2 | t-Butyl |
| 656 | 2 | Propyl |
| 657 | 2 | Benzyl |
| 658 | 2 | Vinyl |
| 659 | 2 | Allyl |
| 660 | 2 | CF₃ |
| 661 | 2 |  |
| 662 | 2 |  |
| 663 | 2 | 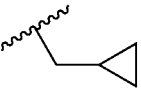 [SMILES: *CC1CC1] |
| 664 | 2 | 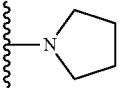 [SMILES: *N1CCCC1] |
| 665 | 2 | 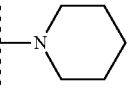 |
| 666 | 2 | 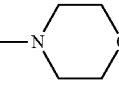 |
| 667 | 2 | NH₂ |
| 668 | 2 | 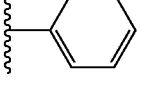 |
| 669 | 2 | 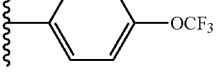 |
| 670 | 2 | 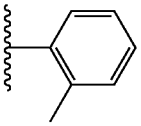 [SMILES: *c1ccccc1C] |
| 671 | 2 | 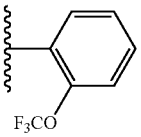 |
| 672 | 2 | 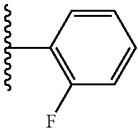 [SMILES: *c1ccccc1F] |
| 673 | 2 | 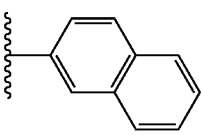 |
| 674 | 2 | 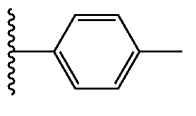 |
| 675 | 2 | F |

Representative compounds of the invention include, but are not limited to, the following compounds (compounds 676 to 750 in Table 10) according to Formula VII-A, wherein, $R_1$ and m are delineated for each compound in Table 10.

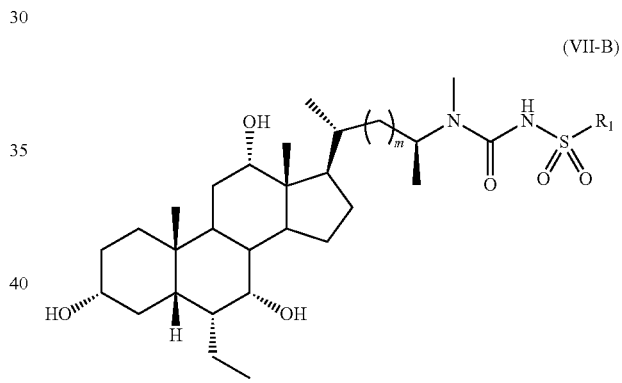

(VII-B)

| Compound | m | R₁₀ |
|---|---|---|
| 676 | 0 | Methyl |
| 677 | 0 | Ethyl |
| 678 | 0 | Isopropyl |
| 679 | 0 | Butyl |
| 680 | 0 | t-Butyl |
| 681 | 0 | Propyl |
| 682 | 0 | Benzyl |
| 683 | 0 | Vinyl |
| 684 | 0 | Allyl |
| 685 | 0 | CF₃ |
| 686 | 0 |  |
| 687 | 0 |  |

| Compound | m | R₁₀ |
|---|---|---|
| 688 | 0 |  |
| 689 | 0 | 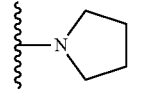 |
| 690 | 0 | 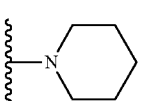 |
| 691 | 0 | 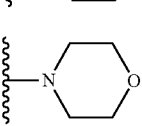 |
| 692 | 0 | H |
| 693 | 0 | 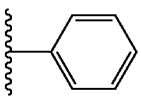 |
| 694 | 0 | 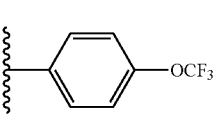 |
| 695 | 0 | 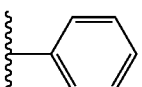 |
| 696 | 0 | 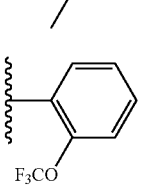 |
| 697 | 0 | 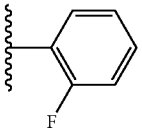 [SMILES: *c1ccccc1F] |
| 698 | 0 | 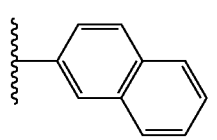 [SMILES: *c1ccc2ccccc2c1] |
| 699 | 0 |  |
| 700 | 0 | 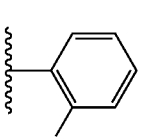 |
| 701 | 1 | Methyl |
| 702 | 1 | Ethyl |
| 703 | 1 | Isopropyl |
| 704 | 1 | Butyl |
| 705 | 1 | t-Butyl |
| 706 | 1 | Propyl |
| 707 | 1 | Benzyl |
| 708 | 1 | Vinyl |
| 709 | 1 | Allyl |
| 710 | 1 | CF₃ |
| 711 | 1 |  |
| 712 | 1 |  |
| 713 | 1 |  |
| 714 | 1 |  |
| 715 | 1 |  |
| 716 | 1 |  |
| 717 | 1 | H |
| 718 | 1 |  |
| 719 | 1 | 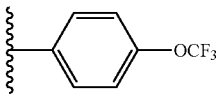 [SMILES: *c1ccc(OC(F)(F)F)cc1] |
| 720 | 1 |  |
| 721 | 1 |  |
| 722 | 1 |  |

-continued

| Compound | m | R₁₀ |
|---|---|---|
| 723 | 1 | 2-naphthyl |
| 724 | 1 | 4-methylphenyl |
| 725 | 1 | 2-methoxyphenyl (MeO) |
| 726 | 2 | Methyl |
| 727 | 2 | Ethyl |
| 728 | 2 | Isopropyl |
| 729 | 2 | Butyl |
| 730 | 2 | t-Butyl |
| 731 | 2 | Propyl |
| 732 | 2 | Benzyl |
| 733 | 2 | Vinyl |
| 734 | 2 | Allyl |
| 735 | 2 | CF₃ |
| 736 | 2 | cyclopropyl |
| 737 | 2 | 1-methylcyclopropyl |
| 738 | 2 | cyclopropylmethyl |
| 739 | 2 | pyrrolidinyl |
| 740 | 2 | piperidinyl |
| 741 | 2 | morpholinyl |
| 742 | 2 | H |
| 743 | 2 | phenyl |
| 744 | 2 | 4-(OCF₃)phenyl |

-continued

| Compound | m | R₁₀ |
|---|---|---|
| 745 | 2 | 2-methylphenyl |
| 746 | 2 | 2-(F₃CO)phenyl |
| 747 | 2 | 2-fluorophenyl |
| 748 | 2 | 2-naphthyl |
| 749 | 2 | 4-methylphenyl |
| 750 | 2 | 2-methoxyphenyl (MeO) |

In certain embodiments, the present invention provides a method for the prevention or treatment of an FXR mediated disease or condition. The method comprises administering a therapeutically effective amount of a compound of the invention. The present invention also provides the use of a compound of the invention for the preparation of a medicament for the prevention or treatment of an FXR mediated disease or condition.

In certain embodiments, the FXR-mediated disease or condition is cardiovascular disease, atherosclerosis, arteriosclerosis, hypercholesteremia, or hyperlipidemia chronic liver disease, gastrointestinal disease, renal disease, metabolic disease, cancer (i.e., colorectal cancer), or neurological indications such as stroke.

In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohn's disease and ulcerative colitis), irritable bowel syndrome (MS), bacterial overgrowth, malabsorption, post-radiation colitis, or microscopic colitis.

In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease.

In certain embodiments, the cardiovascular disease is atherosclerosis, arteriosclerosis, dyslipidemia, hypercholesterolemia, or hypertriglyceridemia.

In certain embodiments, the metabolic disease is insulin resistance, Type I and Type II diabetes, or obesity.

In yet another embodiment, the invention provides the use of the compound or pharmaceutical composition of the invention, in the manufacture of a medicament for a treating or preventing a disease in a subject that involves modulation of the TGR5 receptor. The invention includes a method of treating or preventing a disease that involves modulation of the TGR5 receptor in a subject by administering a compound or pharmaceutical composition of the invention.

In certain embodiments, a disease that involves modulation of the TGR5 receptor is selected from metabolic disease, inflammatory disease, liver disease, autoimmune disease, cardiac disease, kidney disease, cancer, and gastrointestinal disease.

In one aspect, the invention provides for the use, wherein the disease is an inflammatory disease selected from allergy, osteoarthritis, appendicitis, bronchial asthma, pancreatitis, allergic rash, and psoriasis. The invention includes a method of treating or preventing an inflammatory disease selected from allergy, osteoarthritis, appendicitis, bronchial asthma, pancreatitis, allergic rash, and psoriasis.

In one aspect, the invention provides for the use, wherein the disease is an autoimmune disease selected from rheumatoid arthritis, multiple sclerosis, and type I diabetes. The invention includes a method of treating or preventing an autoimmune disease selected from rheumatoid arthritis, multiple sclerosis, and type I diabetes.

In one aspect, the invention provides for the use, wherein the disease is a gastrointestinal disease selected from inflammatory bowel disease (Crohn's disease, ulcerative colitis), short bowel syndrome (post-radiation colitis), microscopic colitis, irritable bowel syndrome (malabsorption), and bacterial overgrowth. The invention includes a method of treating or preventing a gastrointestinal disease selected from inflammatory bowel disease (Crohn's disease, ulcerative colitis), short bowel syndrome (post-radiation colitis), microscopic colitis, irritable bowel syndrome (malabsorption), and bacterial overgrowth.

In one aspect, the invention provides for the use, wherein the disease is kidney disease selected from diabetic nephropathy, chronic renal failure, hypertensive nephrosclerosis, chronic glomerulonephritis, chronic transplant glomerulopathy, chronic interstitial nephritis, and polycystic kidney disease. The invention includes a method of treating or preventing kidney disease selected from diabetic nephropathy, chronic renal failure, hypertensive nephrosclerosis, chronic glomerulonephritis, chronic transplant glomerulopathy, chronic interstitial nephritis, and polycystic kidney disease.

In one aspect, the invention provides for the use, wherein the disease is cancer selected from colorectal cancer, liver cancer, hepatocellular carcinoma, cholangio carcinoma, renal cancer, gastric cancer, pancreatic cancer, prostate cancer, and insulanoma. The invention includes a method of treating or preventing cancer selected from colorectal cancer, liver cancer, hepatocellular carcinoma, cholangio carcinoma, renal cancer, gastric cancer, pancreatic cancer, prostate cancer, and insulanoma.

In one aspect, the compound is a selective FXR agonist over TGR5 activator.

In one aspect, the compound is a selective TGR5 agonist over FXR activator.

In one aspect, the compound is a dual agonist for both FXR and TGR5.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "alkyl", as used herein, refers to a saturated, monovalent straight- or branched-chain hydrocarbon group. Preferred alkyl radicals include $C_1$-$C_6$ alkyl and $C_1$-$C_8$ alkyl radicals. Examples of $C_1$-$C_6$ alkyl groups include, but are not limited to, methyl, ethyl, propyl, isopropyl, n-butyl, tert-butyl, neopentyl, n-hexyl groups; and examples of $C_1$-$C_8$ alkyl groups include, but are not limited to, methyl, ethyl, propyl, isopropyl, n-butyl, tert-butyl, neopentyl, n-hexyl, heptyl, and octyl groups.

The term "alkenyl", as used herein, denote a monovalent group derived from a hydrocarbon moiety by the removal of a single hydrogen atom wherein the hydrocarbon moiety has at least one carbon-carbon double bond. Preferred alkenyl groups include $C_2$-$C_6$ alkenyl and $C_2$-$C_8$ alkenyl groups. Alkenyl groups include, but are not limited to, for example, ethenyl, propenyl, butenyl, 1-methyl-2-buten-1-yl, heptenyl, octenyl and the like.

The term "alkynyl", as used herein, denotes a monovalent group derived from a hydrocarbon moiety by the removal of a single hydrogen atom wherein the hydrocarbon moiety has at least one carbon-carbon triple bond. Preferred alkynyl groups include $C_2$-$C_6$ alkynyl and $C_2$-$C_8$ alkynyl groups. Representative alkynyl groups include, but are not limited to, for example, ethynyl, 1-propynyl, 1-butynyl, heptynyl, octynyl and the like.

The term "carbocycle" refers to a saturated (e.g., "cycloalkyl"), partially saturated (e.g., "cycloalkenyl" or "cycloalkynyl") or completely unsaturated (e.g., "aryl") ring system containing zero heteroatom ring atom. "Ring atoms" or "ring members" are the atoms bound together to form the ring or rings. Where a carbocycle group is a divalent moiety linking two other elements in a depicted chemical structure (such as Z in Formula IA), the carbocycle group can be attached to the two other elements through any two substitutable ring atoms. A $C_4$-$C_6$ carbocycle has 4-6 ring atoms.

The term "cycloalkyl", as used herein, denotes a monovalent group derived from a monocyclic or polycyclic saturated carbocyclic ring compound by the removal of a single hydrogen atom. Preferred cycloalkyl groups include $C_3$-$C_8$ cycloalkyl and $C_3$-$C_{12}$ cycloalkyl groups. Examples of $C_3$-$C_8$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl.

The term "cycloalkenyl" as used herein, denote a monovalent group derived from a monocyclic or polycyclic carbocyclic ring compound having at least one carbon-carbon double bond by the removal of a single hydrogen atom. Preferred cycloalkenyl groups include $C_3$-$C_8$ cycloalkenyl and $C_3$-$C_{12}$ cycloalkenyl groups. Examples of $C_3$-$C_8$-cycloalkenyl include, but are not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, and the like.

The term "aryl," as used herein, refers to a mono- or bicyclic carbocyclic ring system having one or two aromatic rings including, but not limited to, phenyl, naphthyl, tetrahydronaphthyl, indanyl, indenyl and the like.

The term "arylalkyl," as used herein, refers to a $C_1$-$C_3$ alkyl or $C_1$-$C_6$ alkyl residue attached to an aryl ring. Examples include, but are not limited to, benzyl, phenethyl and the like.

The term "heteroaryl," as used herein, refers to a mono-, bi-, or tri-cyclic aromatic radical or ring having from five to ten ring atoms of which at least one ring atom is selected from S, O and N; wherein any N or S contained within the ring may be optionally oxidized. Preferred heteroaryl groups are monocyclic or bicyclic. Heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroarylalkyl," as used herein, refers to a $C_1$-$C_3$ alkyl or $C_1$-$C_6$ alkyl residue residue attached to a heteroaryl ring. Examples include, but are not limited to, pyridinylmethyl, pyrimidinylethyl and the like.

The term "substituted" as used herein, refers to independent replacement of one, two, or three or more of the hydrogen atoms thereon with substituents including, but not limited to, deuterium, —F, —Cl, —Br, —I, —OH, protected hydroxy, —NO$_2$, —CN, —NH$_2$, N$_3$, protected amino, alkoxy, thioalkoxy, oxo, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2C_{12}$-alkenyl, —O—$C_2$-$C_{12}$-alkynyl, —O—$C_3$-$C_{12}$-cycloalkyl, —O-aryl, —O-heteroaryl, —O— heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkynyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH— aryl, —OCONH— heteroaryl, —OCONH— heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_{12}$-alkenyl, —NHCO$_2$—$C_2$-$C_{12}$-alkynyl, —NHCO$_2$—$C_3$-$C_{12}$-cycloalkyl, —NHCO$_2$— aryl, —NHCO$_2$— heteroaryl, —NHCO$_2$— heterocycloalkyl, —NHC(O)NH$_2$, —NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH— heteroaryl, —NHC(O)NH-heterocycloalkyl, NHC(S)NH$_2$, —NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl —SO$_2$NH$_2$, —SO$_2$NH—$C_1$-$C_{12}$-alkyl, —SO$_2$NH—$C_2$-$C_{12}$-alkenyl, —SO$_2$NH—$C_2$-$C_{12}$-alkynyl, —SO$_2$NH—$C_3$-$C_{12}$-cycloalkyl, —SO$_2$NH-aryl, —SO$_2$NH— heteroaryl, —SO$_2$NH— heterocycloalkyl, —NHSO$_2$—$C_1$-$C_{12}$-alkyl, —NHSO$_2$—$C_2$-$C_{12}$-alkenyl, —NHSO$_2$—$C_2$-$C_{12}$-alkynyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S— heterocycloalkyl, methylthiomethyl, or -L'-R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. It is understood that the aryls, heteroaryls, alkyls, and the like can be further substituted. In some cases, each substituent in a substituted moiety is additionally optionally substituted with one or more groups, each group being independently selected from —F, —Cl, —Br, —I, —OH, —NO$_2$, —CN, or —NH$_2$.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo [2.2.1] heptyl, and bicyclo [2.2.2] octyl. Such alicyclic groups may be further substituted.

The term "heterocycloalkyl" and "heterocyclic" can be used interchangeably and refer to a non-aromatic 3-, 4-, 5-, 6- or 7-membered ring or a bi- or tri-cyclic group fused system, where: (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (v) any of the above rings may be fused to a benzene ring, and (vi) the remaining ring atoms are carbon atoms which may be optionally oxo-substituted. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted to give substituted heterocyclic.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, hetoerarylalkylene and heterocycloalkylene groups are to be included in the above definitions, and are applicable to provide the formulas herein with proper valency.

The term "hydroxy activating group", as used herein, refers to a labile chemical moiety which is known in the art to activate a hydroxy group so that it will depart during synthetic procedures such as in a substitution or elimination reactions. Examples of hydroxy activating group include, but not limited to, mesylate, tosylate, triflate, p-nitrobenzoate, phosphonate and the like.

The term "activated hydroxy", as used herein, refers to a hydroxy group activated with a hydroxy activating group, as defined above, including mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, and methoxymethyl groups.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G., S. M. Wuts, *Protective Groups in Organic Synthesis*, 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl) ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2, 2-trichloroethoxymethyl, 2-(trimethyl silyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The terms "halo" and "halogen," as used herein, refer to an atom selected from fluorine, chlorine, bromine and iodine.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Pharmaceutically acceptable salts can also be prepared by deprotonation of the parent compound with a suitable base, thereby forming the anionic conjugate base of the parent compound. In such salts the counter ion is a cation. Suitable cations include ammonium and metal cations, such as alkali metal cations, including $Li^+$, $Na^+$, $K^+$ and $Cs^+$, and alkaline earth metal cations, such as $Mg^{2+}$ and $Ca^{2+}$.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethyl succinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), *Design of Prodrugs,* Elsevier (1985); Widder, et al. (ed.), *Methods in Enzymology,* Vol. 4, Academic Press (1985); Krogsgaard-Larsen, et al., (ed). "Design and Application of Prodrugs, *Textbook of Drug Design and Development,* Chapter 5, 113-191 (1991); Bundgaard, et al., *Journal of Drug Deliver Reviews,* 8:1-38 (1992); Bundgaard, J. of *Pharmaceutical Sciences,* 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

The term "treating", as used herein, means relieving, lessening, reducing, eliminating, modulating, or ameliorating, i.e. causing regression of the disease state or condition. Treating can also include inhibiting, i.e. arresting the development, of a existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations,* VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1, 3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

ABBREVIATIONS

Abbreviations which have been used in the descriptions of the schemes and the examples that follow are:
ACN for acetonitrile;
BME for 2-mercaptoethanol;
BOP for benzotriazol-1-yloxy-tris(dimethylamino)phosphonium hexafluorophosphate;
BzCl for benzoyl chloride;
CDI for carbonyldiimidazole;
COD for cyclooctadiene;
DABCO for 1,4-diazabicyclo[2.2.2]octane;
DAST for diethylaminosulfur trifluoride;
DABCYL for 6-(N-4'-carboxy-4-(dimethylamino)azobenzene)-aminohexyl-1-O-(2-cyanoethyl)-(N,N-diisopropyl)-phosphoramidite;
DBU for 1, 8-Diazabicycloundec-7-ene;
DCC for N, N'-dicyclohexylcarbodiimide;
DCM for dichloromethane;
DIAD for diisopropyl azodicarboxylate;

DIBAL-H for diisobutylaluminum hydride;
DIPEA for diisopropyl ethylamine;
DMAP for N,N-dimethylaminopyridine;
DME for ethylene glycol dimethyl ether;
DMEM for Dulbecco's Modified Eagles Media;
DMF for N,N-dimethyl formamide;
DMSO for dimethylsulfoxide;
DSC for N, N'-disuccinimidyl carbonate;
DPPA for diphenylphosphoryl azide;
DUPHOS for

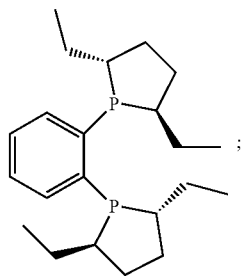 [SMILES: CC[C@@H]1CC[C@@H](CC)P1c1ccccc1P1[C@H](CC)CC[C@H]1CC]

EDANS for 5-(2-Amino-ethylamino)-naphthalene-1-sulfonic acid;
EDCI or EDC for 1-(3-diethylaminopropyl)-3-ethylcarbodiimide hydrochloride;
EtOAc for ethyl acetate;
EtOH for ethyl alcohol;
HATU for O (7-Azabenzotriazole-1-yl)-N,N,N',N'-tetramethyluronium hexafluorophosphate;
HCl for hydrochloric acid;
Hoveyda's Cat. for Dichloro(o-isopropoxyphenylmethylene) (tricyclohexylphosphine)ruthenium(II);
In for indium;
KHMDS is potassium bis(trimethylsilyl) amide;
Ms for mesyl;
NMM for N-4-methylmorpholine;
NMI for N-methylimidazole;
NMO for N-4-methylmorpholine-N-Oxide;
PyBrOP for Bromo-tri-pyrolidino-phosphonium hexafluorophosphate;
Ph for phenyl;
RCM for ring-closing metathesis;
RT for reverse transcription;
RT-PCR for reverse transcription-polymerase chain reaction;
TBME for tert-butyl methyl ether;
TEA for triethyl amine;
$Tf_2O$ for trifluoromethanesulfonic anhydride;
TFA for trifluoroacetic acid;
THF for tetrahydrofuran;
TLC for thin layer chromatography;
$(TMS)_2NH$ for hexamethyldisilazane;
TMSOTf for trimethylsilyl trifluoromethanesulfonate;
TBS for t-Butyldimethylsilyl;
TMS for trimethylsilyl;
TPAP tetrapropylammonium perruthenate;
TPP or $PPh_3$ for triphenylphosphine;
TrCl for trityl chloride;
DMTrCl for 4,4'-dimethoxytrityl chloride;
tBOC or Boc for tert-butyloxy carbonyl.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

As shown in Scheme 1, novel bile acid analogs of the compound of formula (1-5) are prepared from the compound of formula (1-1), wherein $R_1$, m, and $R_7$ are defined as previously, $P_1$ and $P_2$ are hydroxyl protecting groups. Thus, the two hydroxyl groups of the compound of formula (1-1) are protected with $P_1$ and $P_2$ groups to afford the compound of formula (1-2). $P_1$ and $P_2$ can be same or different. $P_1$ and $P_2$ can be any hydroxyl protecting group such as, but not limited to Ac, Bz, chloroacetyl, TES, TBS, MOM and Bn. A more detailed discussion of the procedures, reagents and conditions for protection of hydroxyl group is described in literature, for example, by T. W. Greene and P. G. M. Wuts in "*Protective Groups in Organic Synthesis*" $3^{rd}$ ed., John Wiley & Son, Inc., 1999. Then, the compound of formula (1-2) is converted to the acyl azide compound of formula (1-3) using suitable reagent such as, but not limited to, DPPA. The reaction solvent can be, but not limited to, THF, DCM and toluene. The preferred solvent is THF. The reaction temperature is from −20° C.~40° C. Further rearrangement of the compound of formula (1-3) at elevated temperature and reacting with sulfonamide afford the compound of formula (1-4). Then deprotection of $P_1$ and $P_2$ groups afford the sulfonylurea compound of formula (1-5). A more detailed discussion of the procedures, reagents and conditions for deprotection of hydroxyl pretecting groups is described in literature, for example, by T. W. Greene and P. G. M. Wuts in "*Protective Groups in Organic Synthesis*" $3^{rd}$ ed., John Wiley & Son, Inc., 1999.

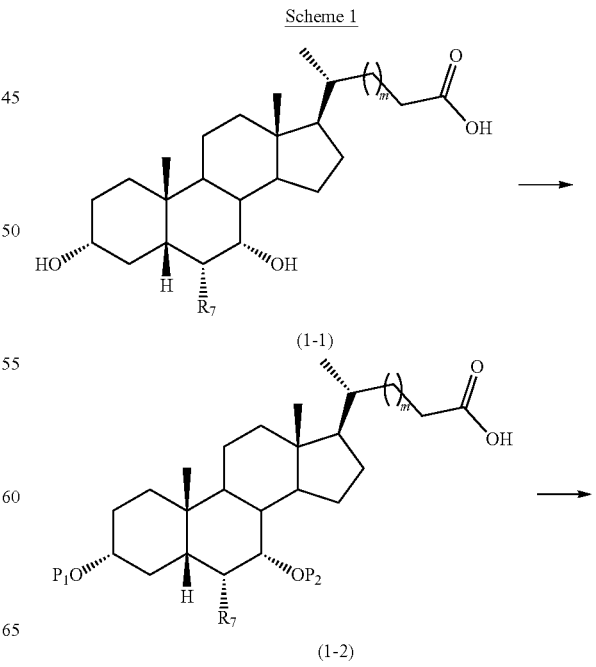

Scheme 1

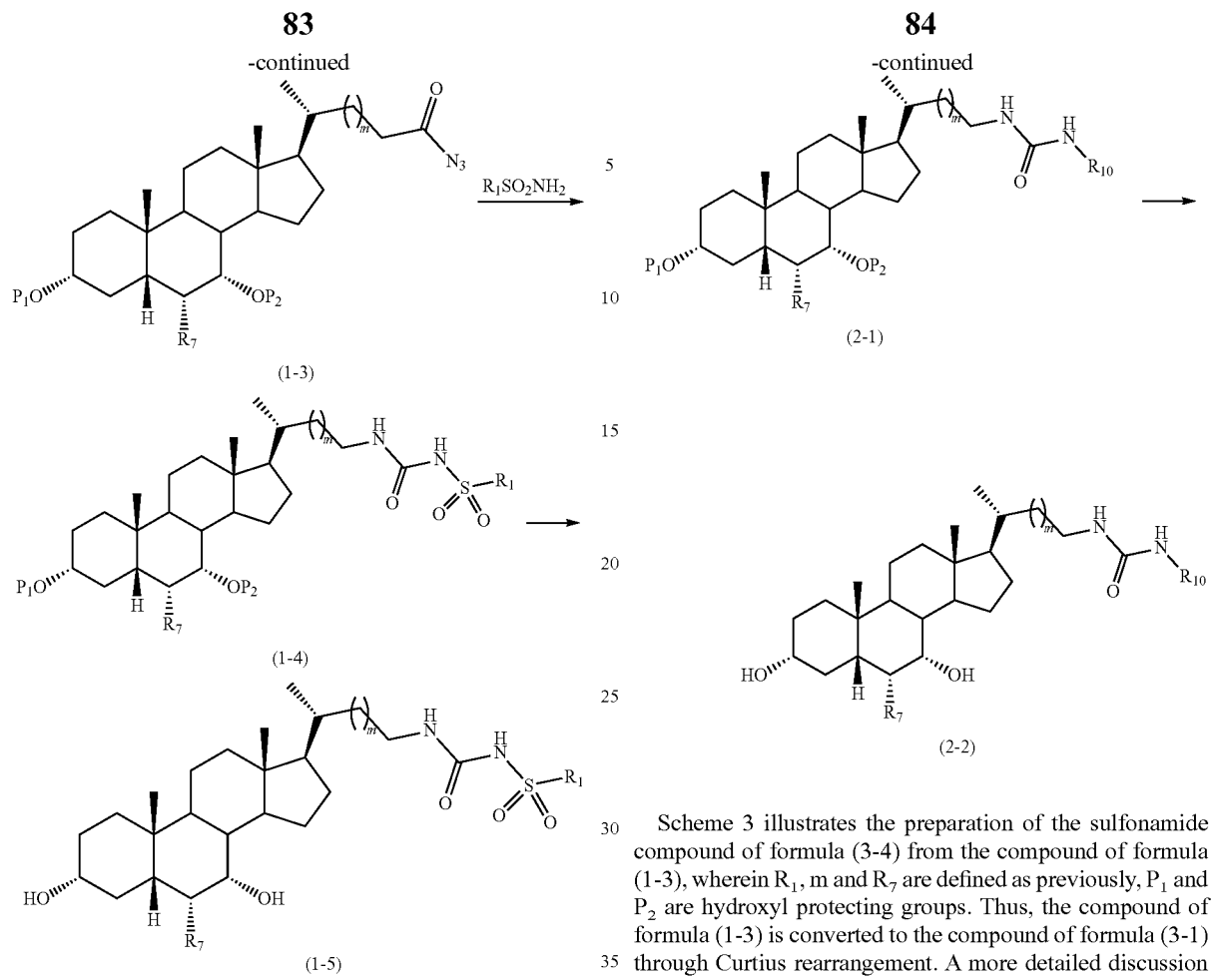

Scheme 2 illustrates the preparation of the urea compound of formula (2-2) from the compound of formula (1-3), wherein $R_{10}$, m, and $R_7$ are defined as previously, $P_1$ and $P_2$ are hydroxyl protecting groups. Thus, rearrangement of the compound of formula (1-3) at elevated temperature and reacting with amine afford the compound of formula (2-1). Then deprotection of $P_1$ and $P_2$ groups afford the urea compound of formula (2-2). A more detailed discussion of the procedures, reagents and conditions for deprotection of hydroxyl pretecting groups is described in literature, for example, by T. W. Greene and P. G. M. Wuts in "*Protective Groups in Organic Synthesis*" 3$^{rd}$ ed., John Wiley & Son, Inc., 1999.

Scheme 3 illustrates the preparation of the sulfonamide compound of formula (3-4) from the compound of formula (1-3), wherein $R_1$, m and $R_7$ are defined as previously, $P_1$ and $P_2$ are hydroxyl protecting groups. Thus, the compound of formula (1-3) is converted to the compound of formula (3-1) through Curtius rearrangement. A more detailed discussion of the procedures, reagents and conditions for Curtius rearrangement is described in literature, for example, by Jerry March in "Advanced Organic Chemistry" 4$^{th}$ ed., John Wiley & Son, Inc., 1992. Then Boc deprotection of the compound of formula (3-1) in acidic condition afford amine compound of formula (3-2). Then the compound of formula (3-2) reacts with sulfonyl chloride to give the sulfonamide compound of formula (3-3). Further deprotection of hydroxyl protecting group $P_1$ and $P_2$ to give the compound of formula (3-4). A more detailed discussion of the procedures, reagents and conditions for protection and deprotection of hydroxyl pretecting groups and amino protecting group are described in literature, for example, by T. W. Greene and P. G. M. Wuts in "*Protective Groups in Organic Synthesis*" 3$^{rd}$ ed., John Wiley & Son, Inc., 1999.

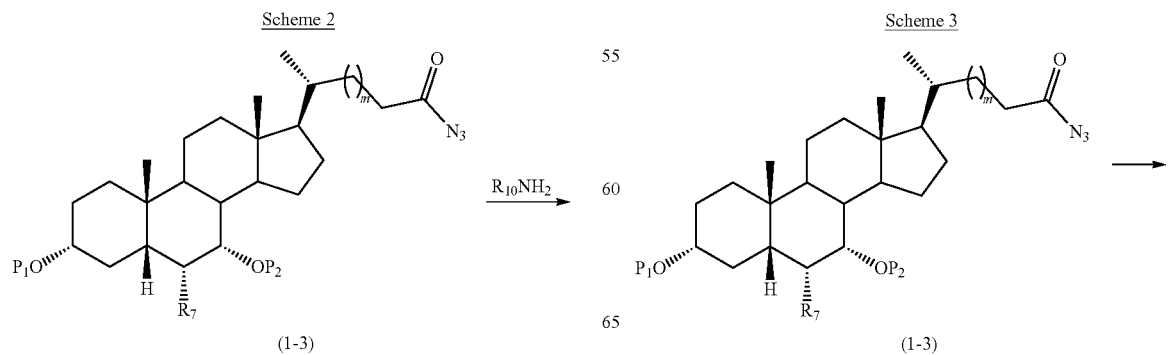

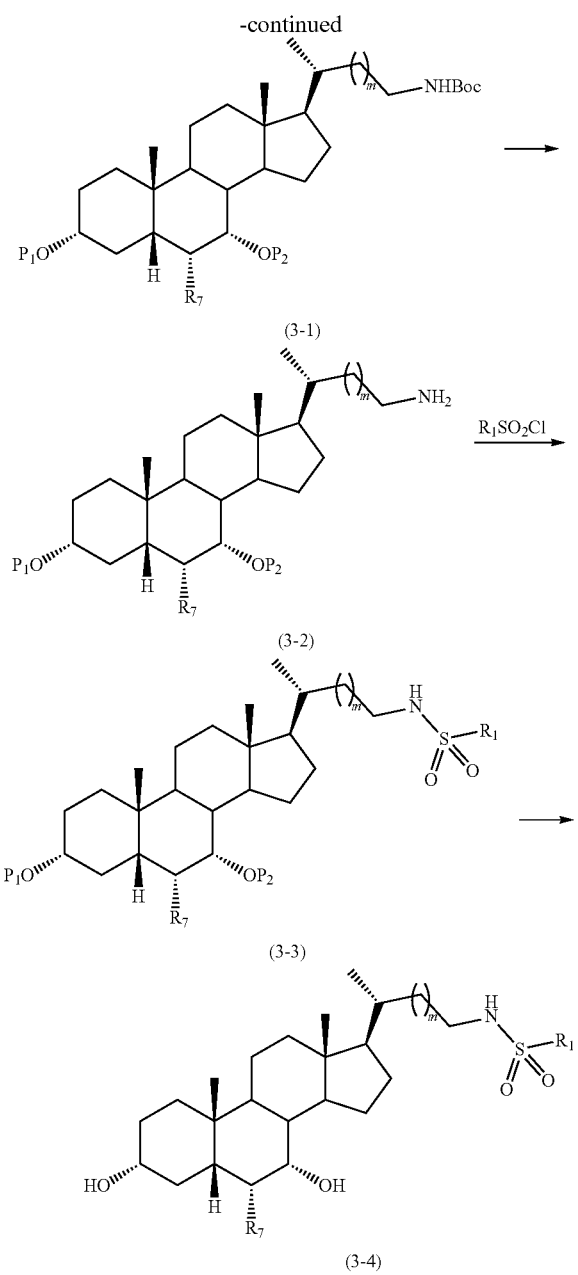

(3-1)

(3-2)

(3-3)

(3-4)

An alternative procedure to prepare sulfonamide compound of formula (4-3) is illustrated in scheme 4, wherein $R_1$, m and $R_7$ are defined as previously, $P_1$ and $P_2$ are hydroxyl protecting groups. The compound of formula (1-2) is coupled with sulfonamide using suitable coupling condition to give the compound of formula (4-1). The coupling reagent can be selected from, but not limited to, DCC, EDC, CDI, di-isopropyl carbodiimide, BOP-Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, $CH_2Cl_2$, DMF or THF. The reaction temperature can vary from 0° C. to about 50° C. The compound of formula (4-1) is treated with reducing agent to give the compound of formula (4-2). The reducing agent can be selected from, but not limited to $LiAlH_4$, $LiBH_4$, DIBAL, $BH_3$. The reaction is carried out in aprotic solvent such as, but not limited to, $CH_2Cl_2$, DMF or THF. The reaction temperature can vary from 0° C. to about 100° C. Further, deprotection of the compound of formula of (4-2) give the compound of formula (4-3). A more detailed discussion of the procedures, reagents and conditions for deprotection of hydroxyl pretecting groups is described in literature, for example, by T. W. Greene and P. G. M. Wuts in "*Protective Groups in Organic Synthesis*" $3^{rd}$ ed., John Wiley & Son, Inc., 1999.

Scheme 4

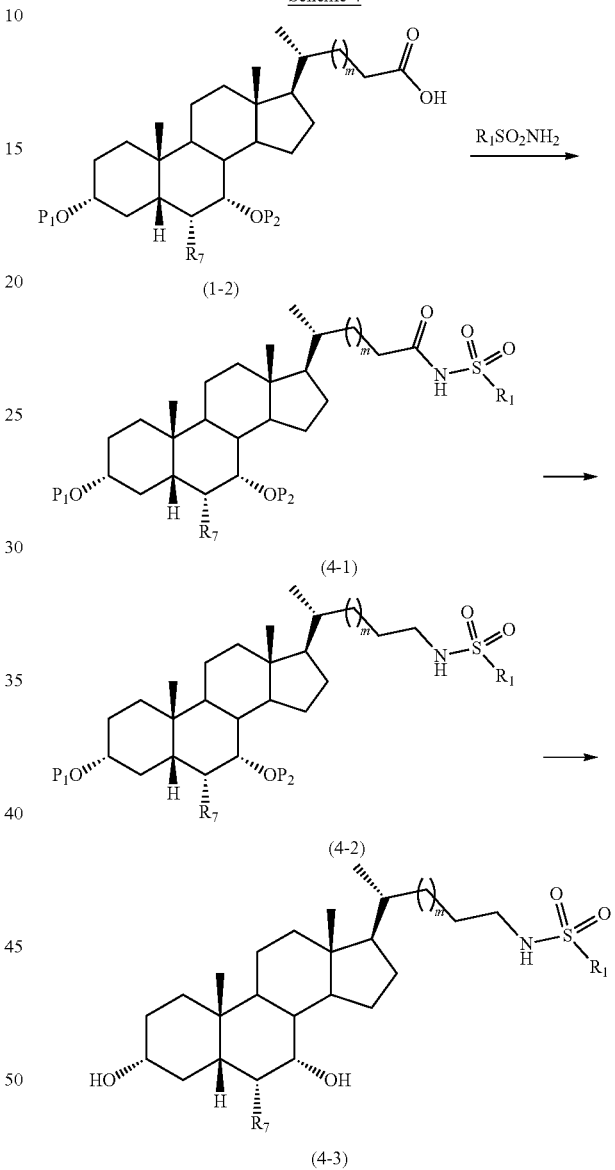

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

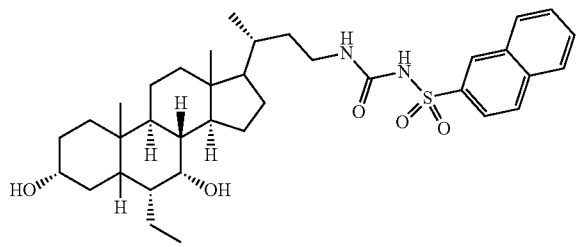

Step 1-1:

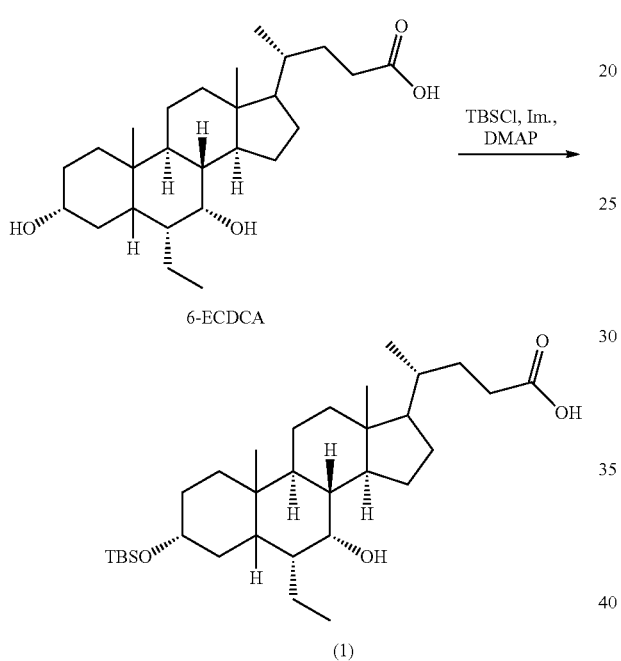

To a 1-dram vial were added 6(α)-ethyl-chenodeoxycholic acid (6-ECDCA) (100 mg, 0.24 mmol), anhydrous THF (3 mL), TBSCl (107.5 mg, 0.71 mmol), and imidazole (57.2 mg, 0.84 mmol) respectively and the reaction mixture was stirred at rt for 22 h. Transferred to a separation funnel, diluted with EtOAC (50 mL) and washed with brine-water (10 mL, 1:1 v/v). Dried, filtered and concentrated and the resulting white solid was dissolved in MeOH (10 mL) and was added K₂CO₃ (49.7 mg, 0.36 mmol). The mixture was stirred at room temperature for 30 min. and cooled to 0° C. Then the reaction mixture was acidified by addition of 0.1 N HCl to PH<7 and diluted with EtOAc (30 mL). After washed with brine (10 mL), dried, and concentrated, the resulting crude material purified by CombiFlash (12 g SiO₂, Acetone/Hexanes=0~40%) to give the compound (1) as a white solid, 88 mg, 65.6% yield over 2 steps.

Step 1-2:

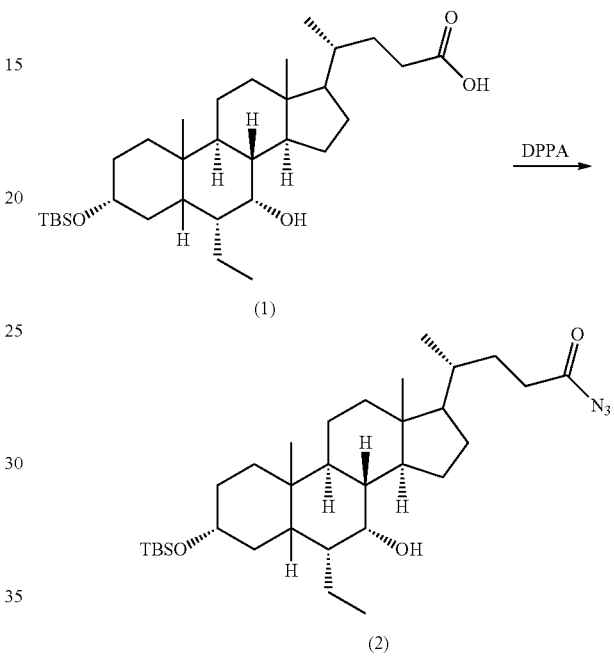

The TBS protected 6(α)-ethyl-chenodeoxycholic acid compound (1) (125 mg, 0.23 mmol) was dissolved in THF (2.0 mL) and cooled to 0° C. To the solution was added Et₃N (64 μL, 0.46 mmol) and diphenylphosphoryl azide (74 μL, 0.35 mmol). The mixture was stirred at 0° C. for 1.5 h, quenched with brine and extracted with DCM (2×). The combined organic layer was dried over Na₂SO₄, filtered and concentrated in vacuo at 25° C. The residue was taken up in hexane, filtered through Na₂SO₄ and concentrated in vacuo at 25° C. The crude product compound (2) (150 mg) was used for next step without purification.

Step 1-3:

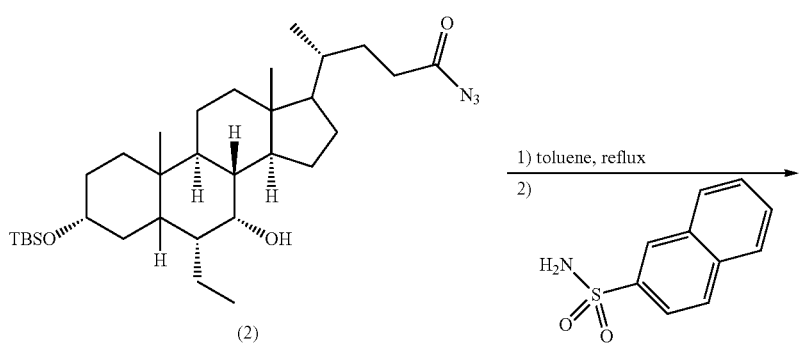

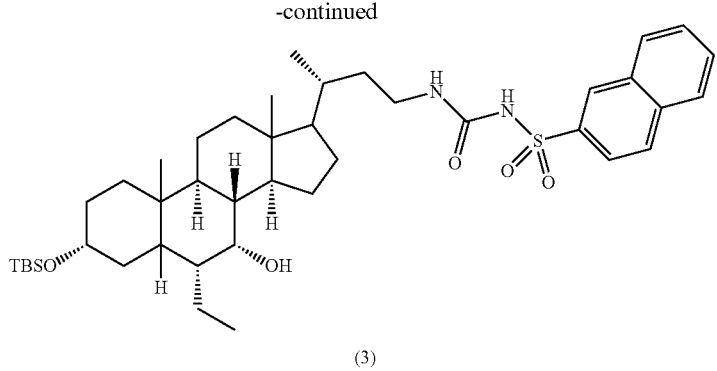

(3)

The acyl azide compound (2) obtained above (75 mg) was dissolved in toluene (2.5 mL) and refluxed for 5 hrs. The mixture was cooled to room temperature and added naphthalene-2-sulfonamide (58 mg, 0.24 mmol) and DBU (36 μL, 0.24 mmol). The reaction mixture was stirred at room temperature for 1 hr, quenched with aq. 1 M HCl, and extracted with EtOAc (2×). The combined organic layer was dried over $Na_2SO_4$, filtered and concentrated in vacuo. The residue was purified by $SiO_2$ chromatography with 0-50% EtOAc/hexane as eluent to provide N-sulfonyl urea compound (3) (74 mg).
Step 1-4:

The above obtained compound (3) (74 mg) was dissolved in MeOH (1.0 mL) followed by addition of 1 drop of 37% conc. HCl. The mixture was stirred at room temperature for 10 min, quenched with sat. $NaHCO_3$, and extracted with EtOAc (3×). The combined organic layer was dried over $Na_2SO_4$, filtered and concentrated in vacuo. The residue was by $SiO_2$ chromatography with 0-50% acetone/hexane as eluent to provide the compound of example 1 (44 mg).

The examples from example 2 to example 8 were prepared using same procedure as the one used in example 1. The MS data and 1H NMR data are delineated in Table 9.

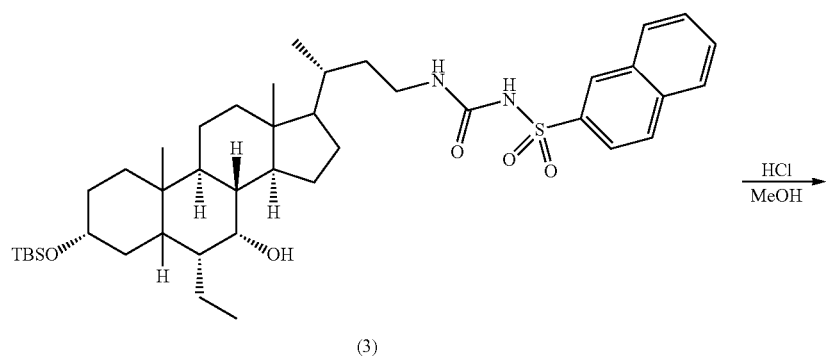

(3)

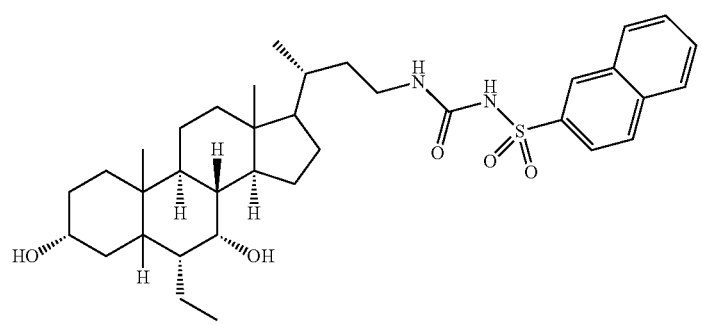

example 1

91
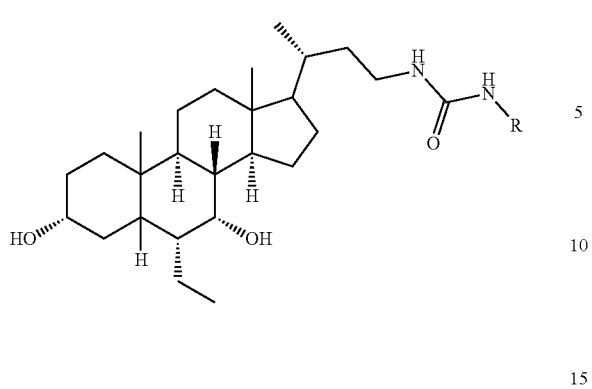
92
Example 8
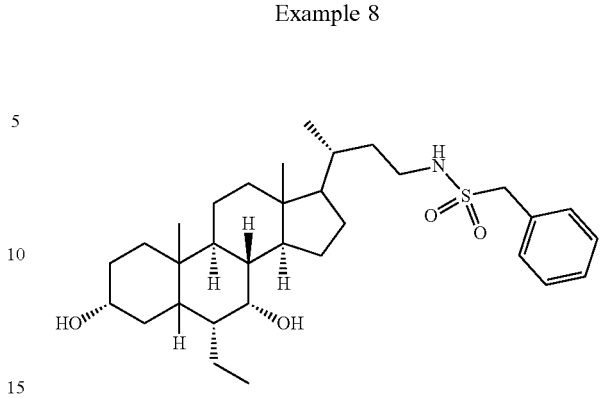
TABLE 9
| Example | R | ESMS: | ¹H NMR (500 MHz) |
|---|---|---|---|
| 1 | naphthalen-2-ylsulfonyl | 623.35 (M − 1) | |
| 2 | 4-(trifluoromethoxy)phenylsulfonyl | 657.25 (M − 1) | 7.95 (2H, d, J = 7.5 Hz), 7.37 (2H, d, J = 7.5 Hz), 6.42 (1H, br s), 3.70 (1H, br s), 3.41 (1H, br s), 3.30 (1H, br s), 3.17 (1H, br s), 0.94 (3H, d, J = 7.0 Hz), 0.89 (6H, m), 0.64 (3H, s). |
| 3 | 4-tert-butylphenylsulfonyl | 629.34 (M − 1) | 7.80 (2H, d, J = 7.5 Hz), 7.55 (2H, d, J = 7.5 Hz), 7.40 (1H, br s), 6.55 (1H, br s), 3.71 (1H, br s), 3.41 (1H, br s), 3.30 (1H, br s), 3.18 (1H, m), 1.35 (9H, s), 0.95 (3H, d, J = 6.0 Hz), 0.92 (3H, m), 0.90 (3H, s), 0.66 (3H, s). |
| 4 | phenylsulfonyl | 573.28 (M − 1) | |
| 5 | cyclopropylsulfonyl | 237.28 (M − 1) | |
| 6 | methylsulfonyl | 511.26 (M − 1) | |
| 7 | iPr | 477.40 (M + 1) | 3.85 (1H, br s), 3.70 (1H, br s), 3.41 (1H, br s), 3.23 (1H, m), 3.12 (1H, m), 1.96 (1H, d, J = 12 Hz), 1.22 (6H, d, J = 6.0 Hz), 0.98 (3H, d, J = 5.5 Hz), 0.90 (6H, br s), 0.67 (3H, s). |

Step 8-1:

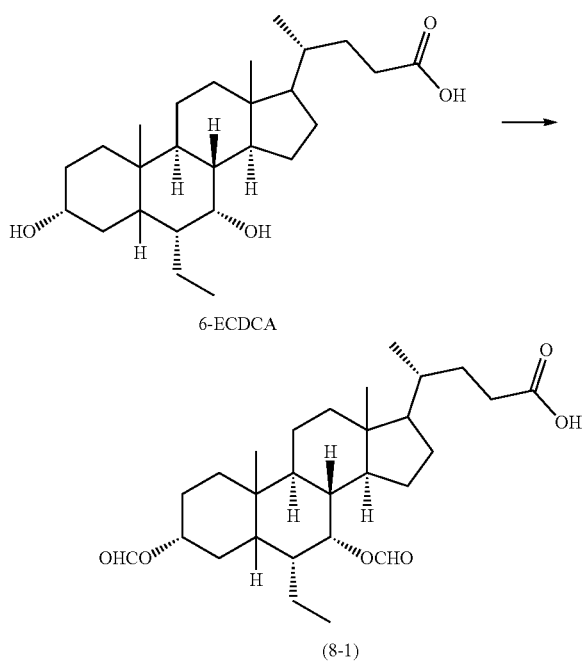

6(α)-ethyl-chenodeoxycholic acid (2.1 g, 2.38 mmol) was dissolved in toluene (11 ml). To the solution was added formic acid (98%, 3.0 mL) and perchloric acid (70%, 20 µL) dropwisely. The mixture was stirred at 105° C. for 3.5 h and cooled to room temperature. The mixture was diluted with EtOAc and washed withbrine. The organic layer was dried over Na$_2$SO$_4$ and concentrated in vacuo. Purification of the residue by SiO$_2$ chromatography with 0-40% acetone/hexane provided compound (8-1) (730 mg).

Step 8-2:

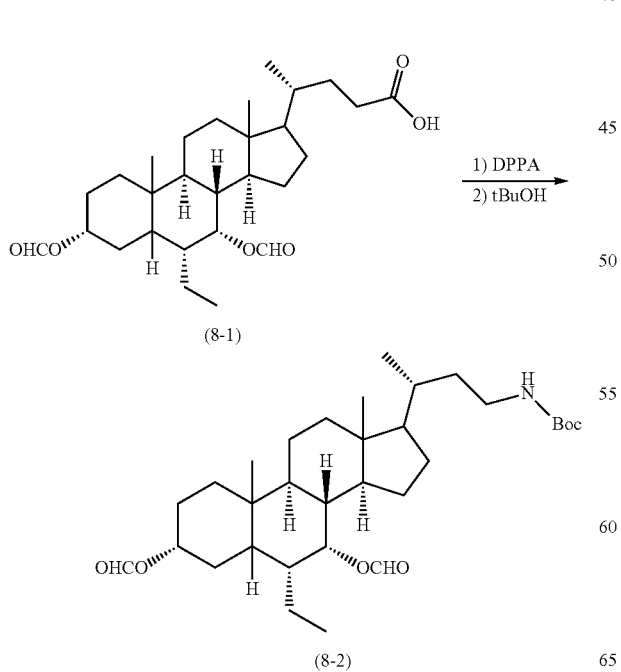

The compound (8-1) (730 mg, 1.53 mmol) was dissolved in THF (8.0 mL) and cooled to 0° C. To the solution was added Et$_3$N (425 µL, 3.06 mmol) and diphenylphosphoryl azide (347 µL, 1.61 mmol). The mixture was stirred at 0° C. for 1.5 h, quenched with water, and extracted with EtOAc (2×). The combined organic layer was dried over Na$_2$SO$_4$, filtered and concentrated in vacuo at 25° C. The crude obtained above was dissolved in toluene (20 mL), stirred at 100° C. for 30 min and t-BuOH (1.5 mL) was added. The mixture was stirred at 100° C. for 18 h, cooled to room temperature, diluted with EtOAc, and washed with water and brine. The organic layer was dried over Na$_2$SO$_4$, filtered and concentrated in vacuo. Purification of the residue by SiO$_2$ chromatography using 0-20% EtOAc/hexane provided compound (8-2) (401 mg). LC/MS Observed [M+NH$_4$]$^+$, 565.42. $^1$HNMR (500 MHz, CDCl$_3$) 8.15 (1H, s), 8.04 (1H, s), 5.19 (1H, s), 4.71 (1H, br s), 4.41 (1H, br s), 3.19 (1H, br s), 3.03 (1H, br s), 1.44 (9H, s), 0.95 (6H, br s), 0.90 (3H, t, J=7.0 Hz), 0.65 (3H, s).

Step 8-3:

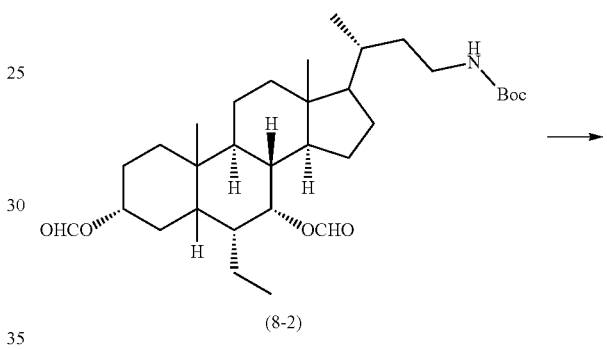

Compound (8-2) (401 mg, 0.73 mmol) was dissolved in DCM (15 mL) and cooled to 0° C. TFA (1.1 mL) was added dropwise and the reaction solution was warmed to room temperature and stirred for 1 h. The solvent was removed in vacuo. The residue was dissolved in DCM and washed with sat. NaHCO$_{03}$. The organic layer was collected, dried over Na$_2$SO$_4$, and concentrated in vacuo. Compound (8-3) (300 mg) was obtained as a white solid. LC/MS observed [M+H]$^+$, 448.

Step 8-4:

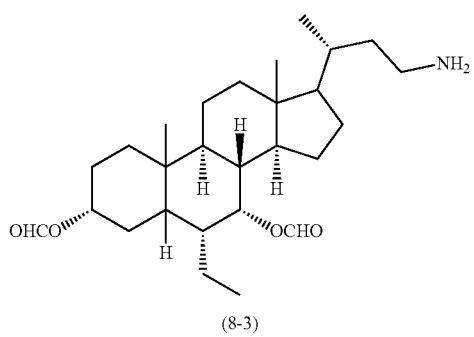

(8-3)

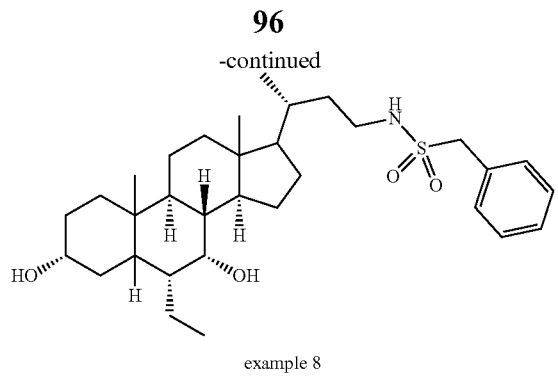

example 8

Compound (8-4) (57 mg, 0.095 mmol) was dissolved in MeOH (0.5 mL). To the solution was added aq. 50% NaOH solution (0.23 mL, 30 eq). The mixture was stirred at 50° C. for 15 h, cooled to room temperature, quenched with 1 M HCl, and extracted with EtOAc (3×). The organic layer was dried over $Na_2SO_4$ and concentrated in vacuo. Purification of the residue provided compound of example 8. LC/MS observed [M+HCOOH−H]⁻, 590.25.

Example 9

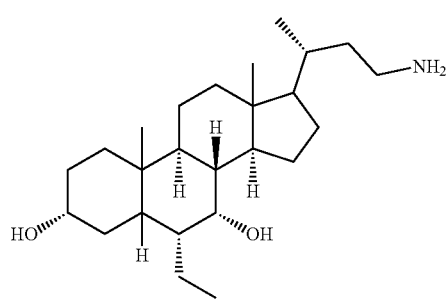

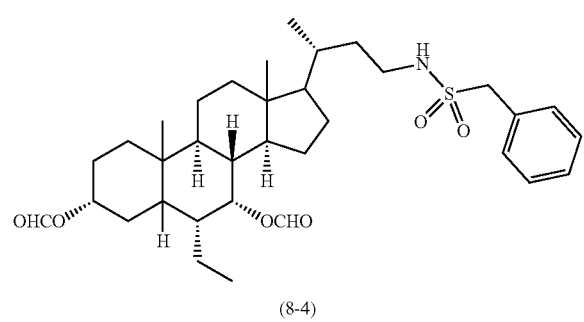

(8-4)

The amine compound (8-3) (100 mg, 0.22 mmol) was dissolved in DCM (1.0 mL), followed by addition of $Et_3N$ (67 µL, 0.48 mmol) and phenylmethanesulfonyl chloride (46 mg, 0.24 mmol). The reaction mixture was stirred at room temperature for 18 hrs, quenched with 5% $NaHCO_3$, and extracted with DCM (3×). The combined organic layers was dried over $Na_2SO_4$ and concentrated in vacuo. Purification of the residue by $SiO_2$ chromatography using 0-30% EtOAc/hexane provided compound (8-4) (57 mg). LC/MS observed [M+NH_4]⁺, 619.38; [M+HCOOH−H]⁻, 646.27. ¹HNMR (500 MHz, $CDCl_3$) 8.15 (1H, s), 8.03 (1H, s), 7.38 (5H, s), 5.18 (1H, s), 4.70 (1H, br s), 4.24 (2H, s), 3.94 (1H, br s), 3.02 (1H, br s), 2.93 (1H, br s), 0.95 (3H, s), 0.89 (6H, m), 0.63 (3H, s).

Step 8-5:

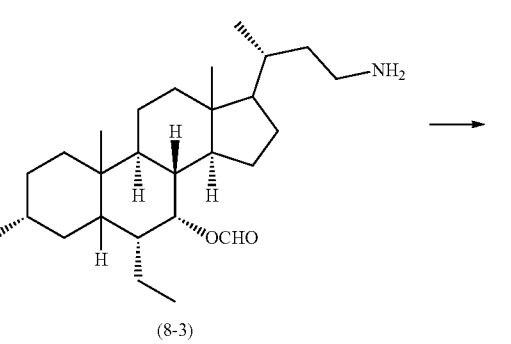

(8-3)

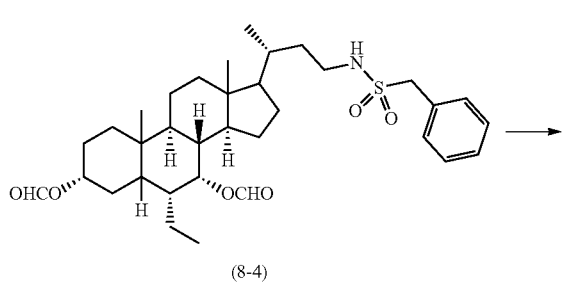

(8-4)

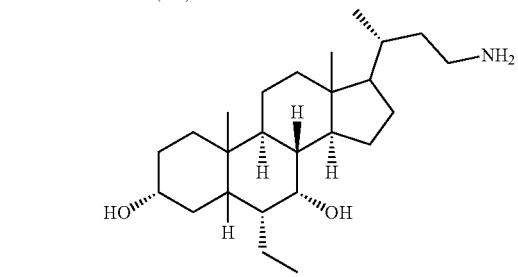

Compound (8-3) (57 mg, 0.095 mmol) was dissolved in MeOH (0.5 mL). To the solution was added aq. 50% NaOH solution (0.23 mL, 30 eq). The mixture was stirred at 50° C. for 15 h, cooled to room temperature, quenched with 1 M HCl, and extracted with EtOAc (3×). The organic layer was dried over Na₂SO₄ and concentrated in vacuo. Purification of the residue provided compound of example 9. LC/MS observed [M+1], 392.25.

Example 10

4.33 (1H, br s), 3.69 (1H, s), 3.41 (1H, br s), 3.92 (2H, br s), 0.90 (3H, t, J=7.5 Hz), 0.89 (3H, s), 0.85 (3H, d, J=5.5 Hz), 0.62 (3H, s).

Example 11

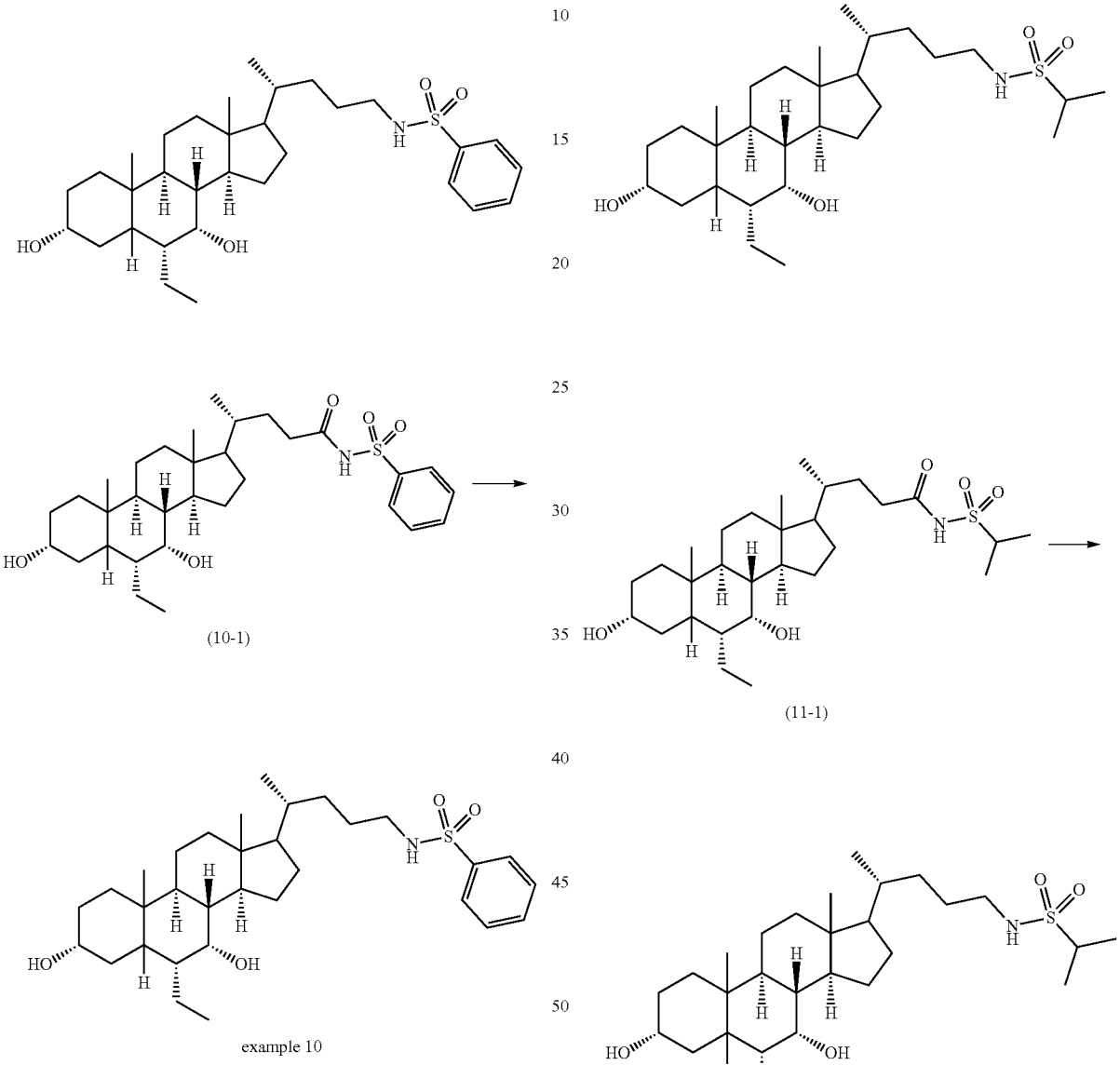

example 10 example 11

The acylsulfonamide (10-1) (100 mg, 0.18 mmol) was dissolved in THF (2 mL). To the solution at −78° C. was added LiAlH₄ solution in THF (1.0 M in THF, 1.44 mL) dropwise. The mixture was warmed to room temperature and stirred for 1 h. The reaction was quenched at 0° C. with saturated potassium sodium tartrate and stirred at room temperature for 14 hrs. The mixture was extracted with EtOAc (2×) and the combined organic layer was dried over Na₂SO₄ and concentrated in vacuo. Purification of the residue by SiO₂ chromatography with 0-50% EtOAc/hexane provided compound of example 10 (42 mg). LC/MS observed [M+HCOOH−H]⁻, 590.29. ¹HNMR (500 MHz, CDCl₃) 7.87 (2H, d, J=7.5 Hz), 7.59 (1H, m), 7.52 (2H, m), The compound of example 11 was prepared using a similar procedure as the compound of example 10. LC/MS observed [M+HCOOH−H]⁻, 556.31. ¹HNMR (500 MHz, CDCl₃) 3.69 (1H, br s), 3.40 (1H, br s), 3.14 (1H, m), 3.09 (2H, m), 1.95 (1H, d, J=12 Hz), 1.37 (6H, d, J=5.5 Hz), 0.93-0.89 (9H, m), 0.65 (3H, s).

The examples from example 129 to example 143 were prepared using similar procedure as above. The MS data are delineated in Table 10.

TABLE 10

| Example # | Structure | MS data |
|---|---|---|
| 129 | 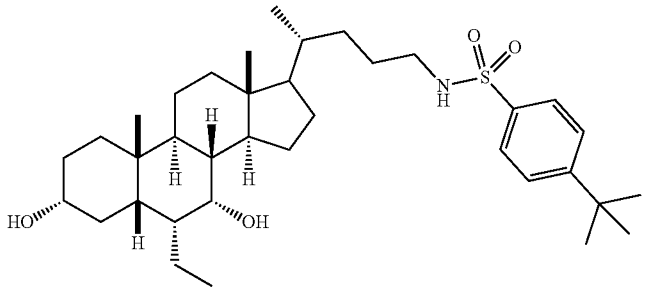 | [M + HCOOH − 1]⁻, 646.42 |
| 130 | 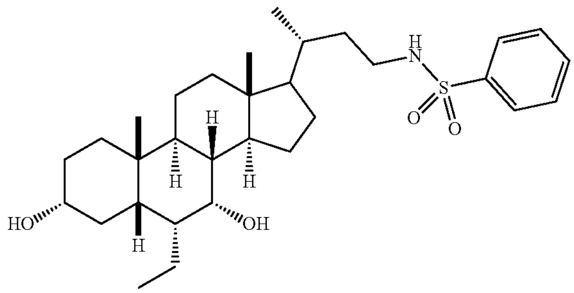 | [M + HCOOH − 1]⁻, 576.26 |
| 131 | 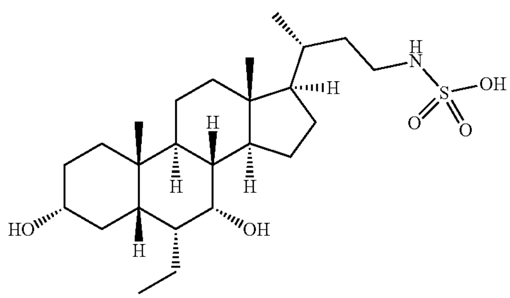 | [M − 1]⁻, 470 |
| 132 | 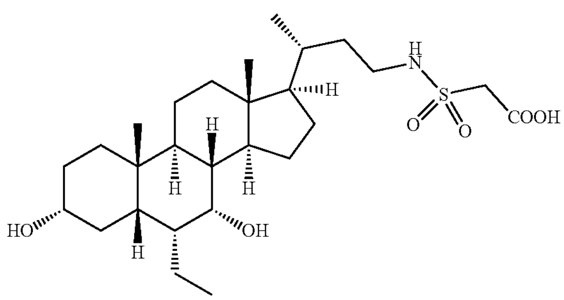 | [M − 2H₂O + 1]⁺, 478.4 |
| 133 | 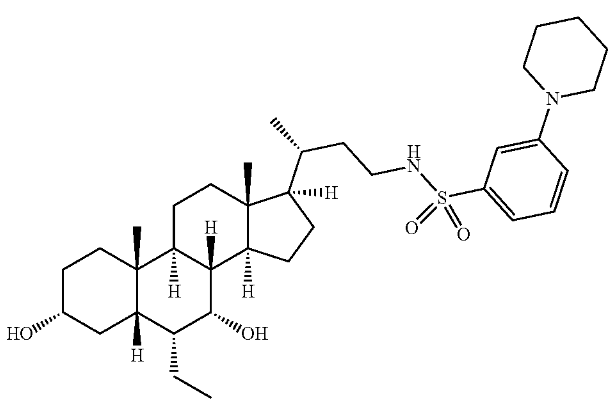 | [M + 1]+, 615.60 |

TABLE 10-continued
| Example # | Structure | MS data |
|---|---|---|
| 134 | 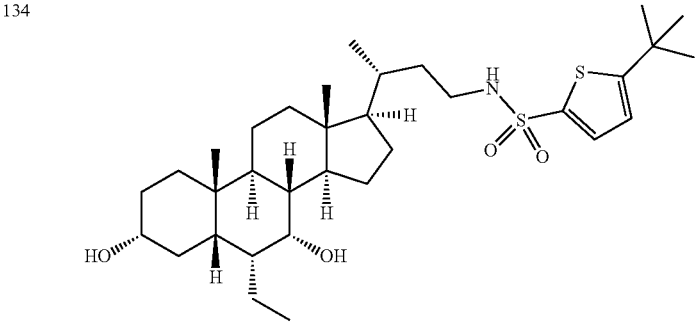 | [M − 2H₂O + 1]⁺, 558.50 |
| 135 | 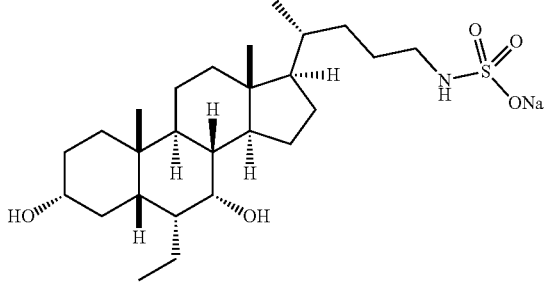 | [M − 1]⁻, 484 |
| 136 | 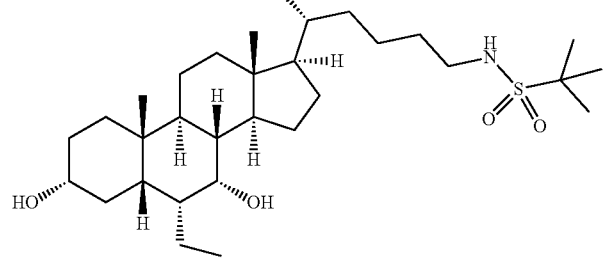 | [M − 1]⁻, 538.40 |
| 137 | 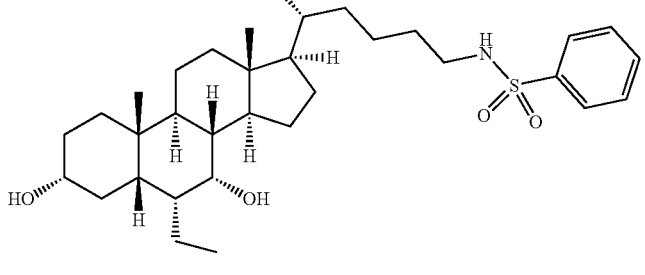 | [M − 1]⁻, 558.35 |
| 138 | 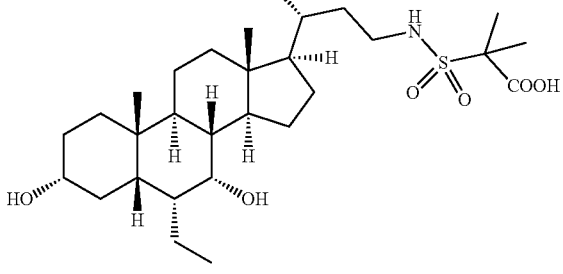 | [M − 2H₂O + 1]⁺, 506.35 |

TABLE 10-continued
| Example # | Structure | MS data |
|---|---|---|
| 139 | 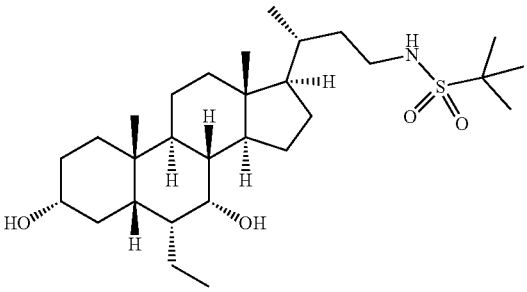 | [M − 1]⁻, 510.45 |
| 140 | 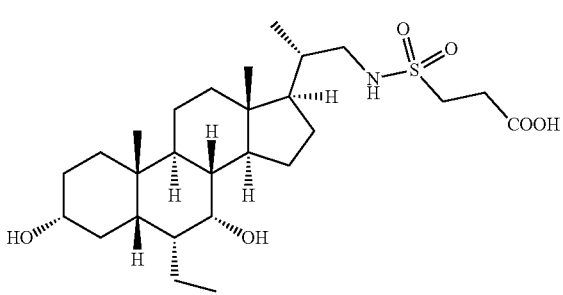 | [M − 1]⁻, 512.30 |
| 141 | 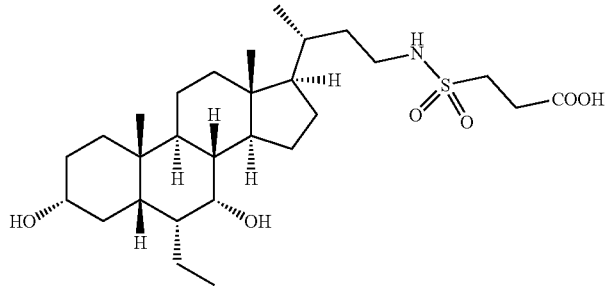 | [M − 2H$_2$O + 1]⁺, 492.50 |
| 142 | 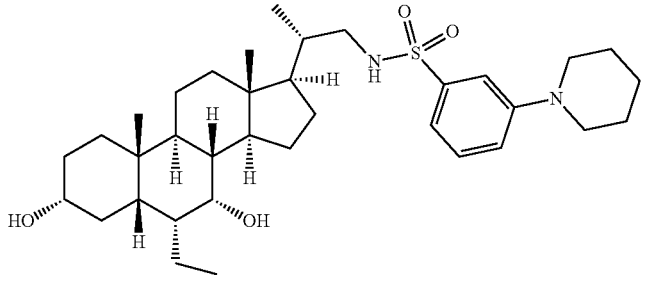 | [M − 1]⁻, 599.20 |
| 143 | 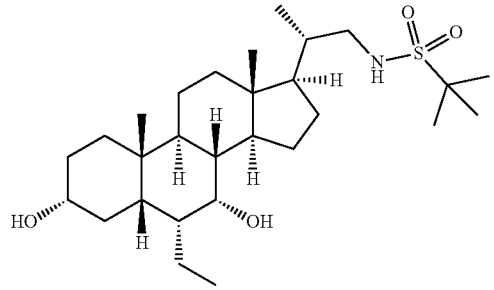 | [M − 1]⁻, 496.2 |

Example 108

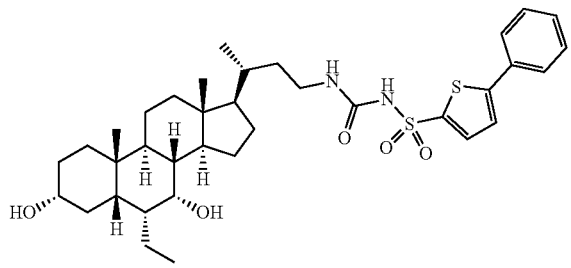

Example 109

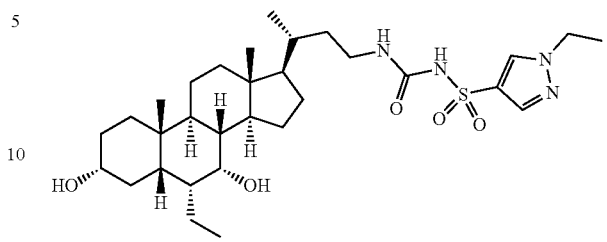

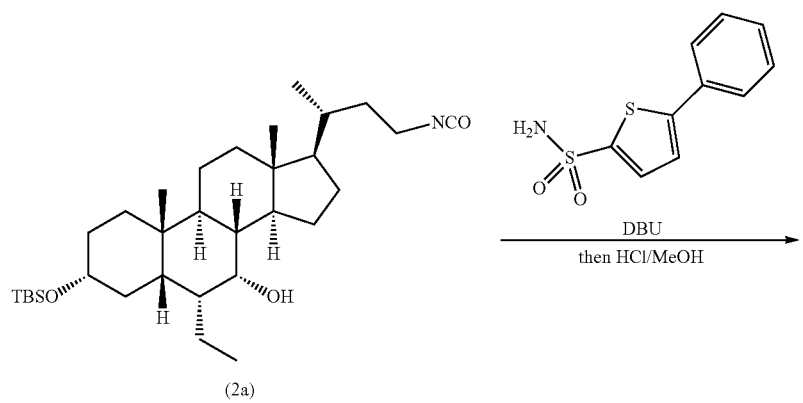

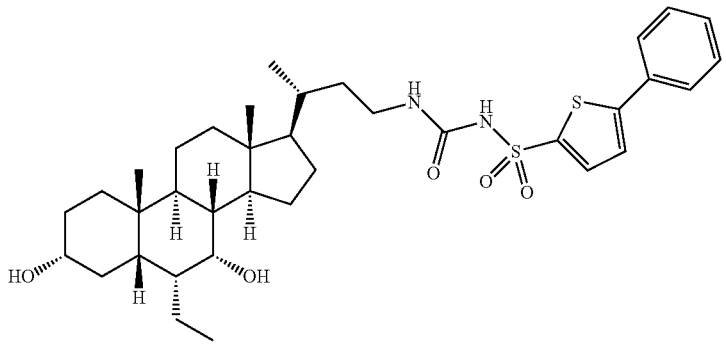

example 108

5-Phenylthiophene-2-sulfonamide (145 mg, 0.6 mmol) and DBU (91 mg, 0.6 mmol) in THF (5 mL) was added into a solution of the compound (2a) (1 mL, 0.2 mmol) in toluene. The mixture was stirred at RT for overnight. The mixture was quenched with water, extracted with ethyl acetate (50 mL), dried, filtered, and concentrated. The residue was dissolved in MeOH (2 mL), then 1 drop of 37% HCl was added. The mixture was stirred at rt for 10 minutes, then was diluted with ethyl acetate (50 mL) and washed sequentially with saturated sodium bicarbonate and brine. The organic layer was dried over $Na_2SO_4$, filtered and concentrated. The residue was purified by Flash-Prep-HPLC ((IntelFlash-1): Column, C18; mobile phase, MeCN/$H_2O$, Detector, UV 254 nm) to give the example 108 (15.5 mg) as a white solid.

1). Synthesis of Compound (109-1)

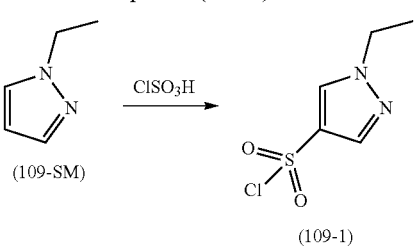

Compound (109-SM) (1 g, 10 mmol) was added to chlorosulfonic acid (10 mL) at room temperature and the mixture was slowly warmed to 100° C., and then heated at 100-110° C. for 2 hours. The reaction mixture was cooled, poured into 150 mL of crushed ice with stirring, and extracted with ethyl acetate (20 mL*3). The organic layer was combined, washed with saturated brine (30 mL), dried over Na$_2$SO$_4$, evaporated to obtain 1.25 g of the title compound (109-1) as a yellow oil which was used in the next step directly.

2). Synthesis of Compound (109-2)

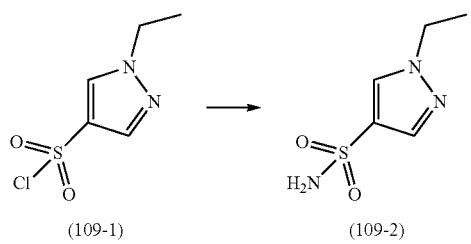

A solution of the compound (109-1) (1.25 g, 6.48 mmol) in THF (40 mL) and ammonia (40 mL) was stirred at rt for 1.5 h. Then the solution was concentrated. The residue was purified by flash silica chromatography, elution gradient 40 to 100% EtOAc in petroleum ether to give the title compound (109-2) (510 mg, 45%) as a yellow solid.

3). Synthesis of Example 109

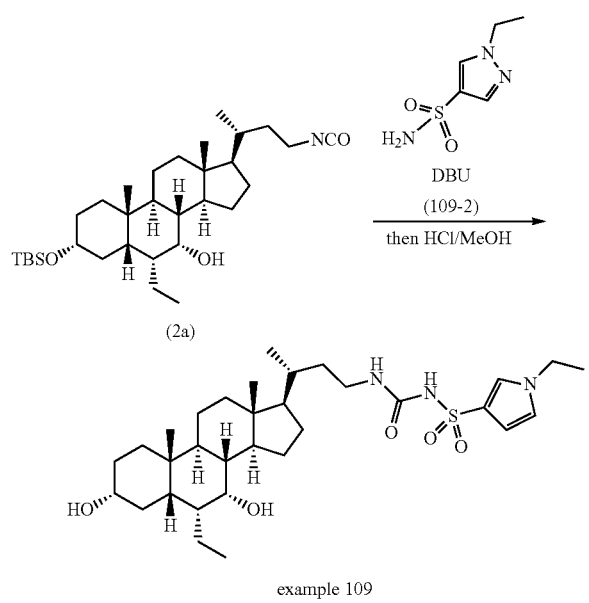

Compound (109-2) (87.5 mg, 0.5 mmol) and DBU (76 mg, 0.5 mmol) in THF (5 mL) was added into a solution of the compound (2a) (1 mL, 0.2 mmol) in toluene. The mixture was stirred at RT for overnight. The mixture was quenched with water, extracted with ethyl acetate (50 mL), dried, filtered, and concentrated. The residue was dissolved in MeOH (2 mL), then 1 drop of 37% HCl was added. The mixture was stirred at rt for 10 minutes, then was diluted with ethyl acetate (50 mL) and washed sequentially with saturated sodium bicarbonate and brine. The organic layer was dried over Na$_2$SO$_4$, filtered and concentrated. The residue was purified by Flash-Prep-HPLC ((IntelFlash-1): Column, C18; mobile phase, MeCN/H$_2$O, Detector, UV 220 nm) to give example 109 (25.1 mg) as a white solid.

Example 111

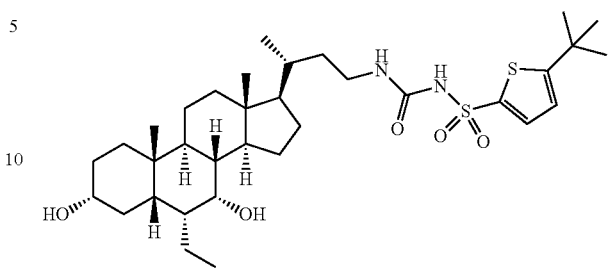

1). Synthesis of Compound (111-1)

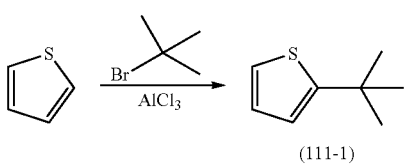

A solution of thiophene (6.0 g, 71.31 mmol) and 2-bromo-2-methylpropane (9.7 g, 70.79 mmol) in DCM (60 mL) was added dropwise to trichloroalumane (9.4 g, 70.50 mmol) in DCM (60 mL) at −78° C. The resulting solution was stirred at −78° C. for 2 h and warmed to rt for overnight. The resulting mixture was diluted with DCM (200 mL), and washed with water (50 mL), 5% sodium hydroxide (50 mL) and saturated brine (50 mL) sequentially. The organic layer was dried over Na$_2$SO$_4$ and concentrated under vacuum to give 6.1 g (crude) of desired compound as a yellow oil.

2). Synthesis of Compound (111-2)

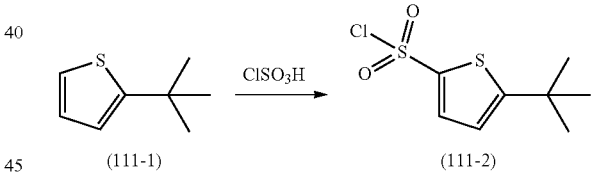

A solution of (111-1) (5 g, 35.7 mmol) in DCM (10 mL) was added dropwise to an ice-cold solution of chlorosulfonic acid (12.4 g, 107 mmol) in DCM (30 mL). The reaction mixture was stirred at 0° C. for 30 min, then poured into ice. The solution was extracted with DCM (20 mL*3). The combined organic layer was washed with H$_2$O (30 mL), and saturated NaCl (30 mL), then dried over Na$_2$SO$_4$, filtered and evaporated to give 4.1 g (crude) of (111-2) as a yellow oil which was used in the next step directly.

3). Synthesis of Compound (111-3)

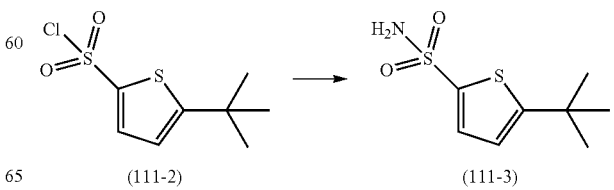

A solution of (111-2) (4.1 g, 17.2 mmol) in THF (40 mL) and ammonia (40 mL) was stirred at rt for 1.5 hours. Then was concentrated. The residue was purified by flash silica chromatography, elution gradient 40 to 100% EtOAc in petroleum ether to give the title compound (2.1 g, 56%) as a yellow solid.

4). Synthesis of Example 111

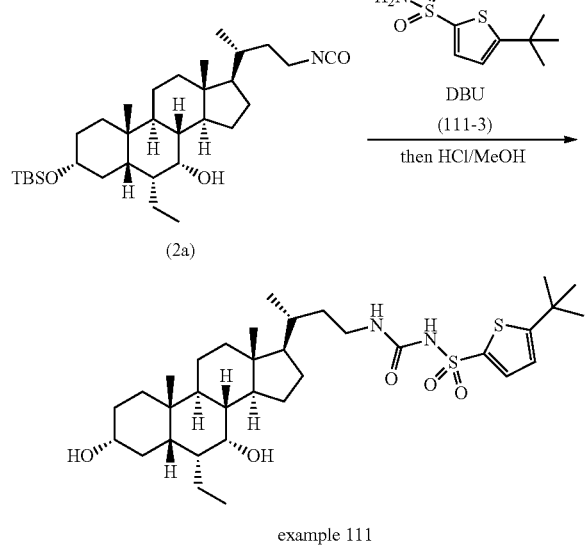

example 111

Compound (113-3) (110 mg, 0.5 mmol) and DBU (76 mg, 0.5 mmol) in THF (5 mL) was added into a solution of the compound (2a) (1 mL, 0.2 mmol) in PhCH₃. The mixture was stirred at RT for overnight. The mixture was quenched with water, extracted with ethyl acetate (50 mL), dried, filtered, and concentrated. The residue was dissolved in MeOH (2 mL), then 1 drop of 37% HCl was added. The mixture was stirred at rt for 10 minutes, then was diluted with ethyl acetate (50 mL) and washed sequentially with saturated sodium bicarbonate and brine. The organic layer was dried over Na₂SO₄, filtered and concentrated. The residue was purified by Flash-Prep-HPLC ((IntelFlash-1): Column, C18; mobile phase, MeCN/H₂O, Detector, UV 254 nm) to give the example 111 (29.4 mg) as a white solid.

Example 112

1). Synthesis of Compound (112-1)

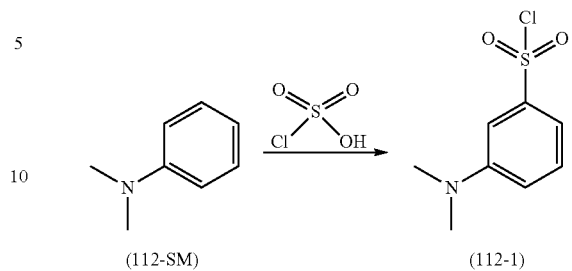

A solution of Compound (112-SM) (4 mL) in DCM (10 mL) was added dropwise to an ice-cold solution of chlorosulfonic acid (10 mL) in DCM (30 mL). The reaction mixture was stirred for 2 h at RT, then poured into ice. The solution was extracted with DCM (20 mL*3). The combined organic layer was washed with saturated brine (30 mL), dried over Na₂SO₄, filtered, and evaporated to give 1.1 g (crude) of (112-1) as a yellow oil, which was used in the next step directly.

2). Synthesis of Compound (112-2)

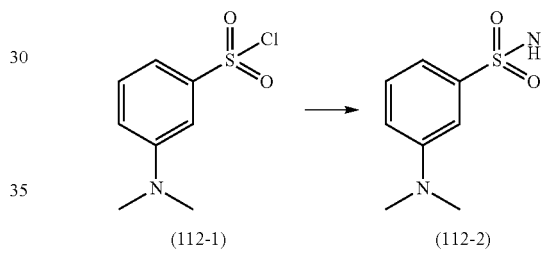

A solution of the compound (112-1) (1.1 g) in THF (40 mL) and ammonia (40 mL) was stirred at rt for 1.5 h. Then the solution was concentrated. The residue was purified by flash silica chromatography, elution gradient 50 to 100% EtOAc in petroleum ether to give 550 mg of title compound (112-2) as a yellow solid.

3). Synthesis of Example 112

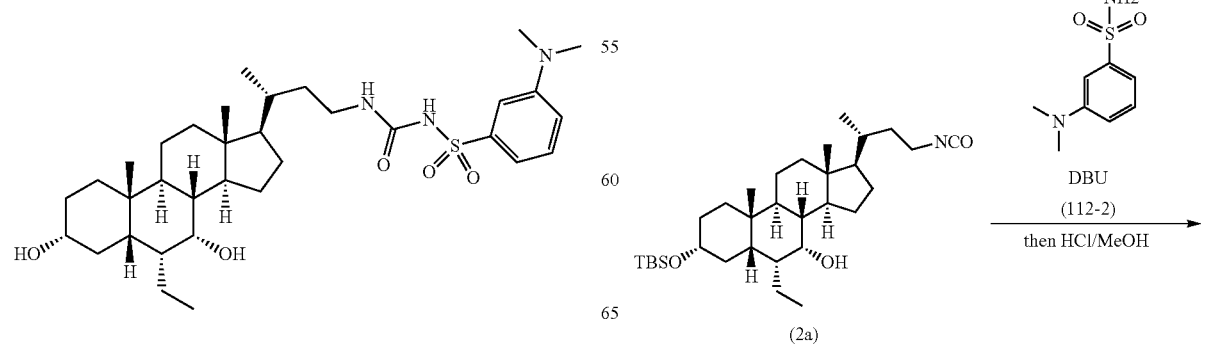

-continued

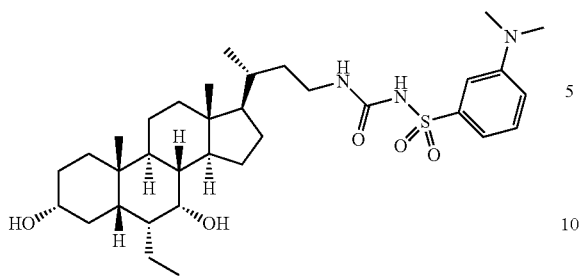

example 112

-continued

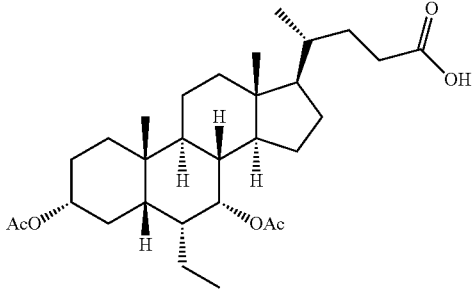

(113-1)

Compound (112-2) (100 mg, 0.5 mmol) and DBU (76 mg, 0.5 mmol) in THF (5 mL) was added into a solution of compound (2a) (1 mL, 0.2 mmol) in toluene. The mixture was stirred at RT for overnight. The mixture was quenched with water, extracted with ethyl acetate (50 mL), dried, filtered, and concentrated. The residue was dissolved in MeOH (2 mL), then 1 drop of 37% HCl was added. The mixture was stirred at rt for 10 minutes, then was diluted with ethyl acetate (50 mL) and washed sequentially with saturated sodium bicarbonate and brine. The organic layer was dried over $Na_2SO_4$, filtered and concentrated. The residue was purified by Flash-Prep-HPLC ((IntelFlash-1): Column, C18; mobile phase, MeCN/$H_2O$, Detector, UV 254 nm) to give example 112 (21.5 mg, 18%) as a white solid.

Into a 1000 mL round-bottom flask purged and maintained with an inert atmosphere of nitrogen, was placed a solution of 6-ECDCA (18.0 g, 0.04 mol, 1.00 eq) in THF (200 mL), TEA (86.5 g, 0.86 mol, 20.0 eq), 4-dimethylaminopyridine (0.63 g, 0.004 mol, 0.1 eq), and acetic anhydride (87.3 g, 0.86 mol, 20.0 eq). The resulting solution was stirred at 90° C. for 15 hours. After being cooled to rt, it was concentrated and the residue was dissolved in ethyl acetate (500 mL), then was washed with water (100 mL*2), saturated NaCl (100 mL*2). The organic layer was dried over $Na_2SO_4$, filtered and concentrated. The residue was purified by flash silica chromatography, elution gradient 0 to 20% EtOAc in petroleum ether to give the desired compound (113-1) as a yellow solid (20.0 g, 92.6%).

2). Synthesis of Compound (113-2)

Example 113

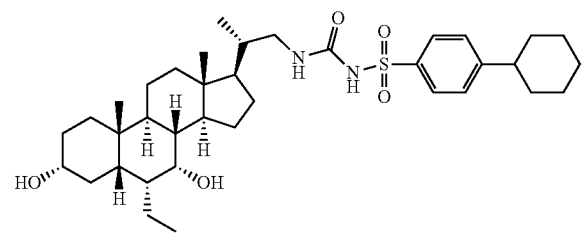

1). Synthesis of Compound (113-1)

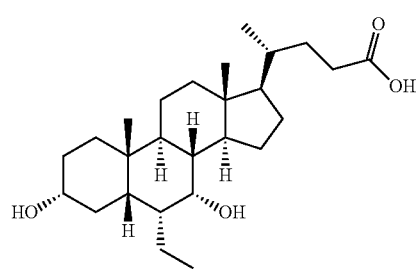

6-ECDCA

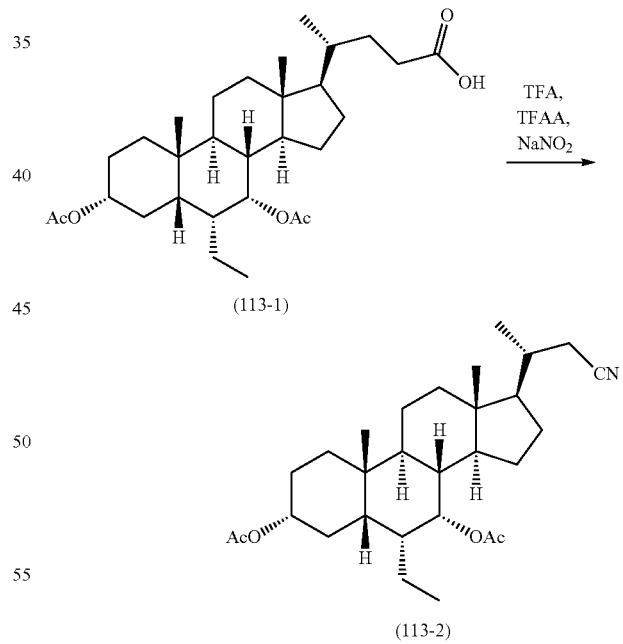

Into a solution of (93-1) (20.0 g, 40 mmol) in TFA (150 mL) was added TFAA (63.0 g, 300 mmol). Then $NaNO_2$ was added in 5 portions over 45 minutes at 0° C. After stirred at 0° C. for 1 hour, the solution was moved to 40° C. for 40 minutes. The solution was quenched with water after being cooled to rt, then extracted with ethyl acetate (200 mL*3). The organic layer was dried over $Na_2SO_4$, filtered and concentrated. The residue was purified by flash silica chromatography, elution gradient 10 to 30% EtOAc in petroleum ether to give the desired compound as a yellow solid (12.2 g, 65.6%).

3). Synthesis of Compound (113-3)

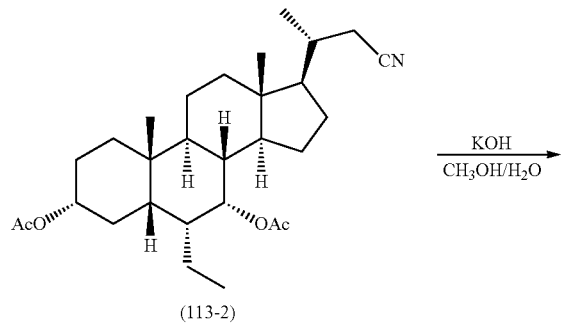

(113-2)

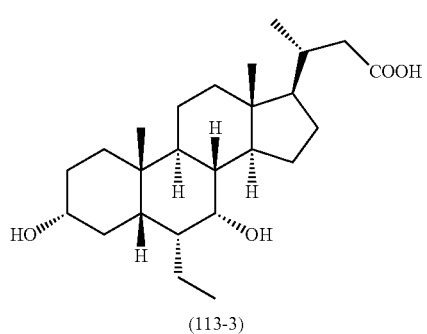

(113-3)

Into a solution of (113-2) (11.7 g, 24.8 mmol) in CH₃OH (100 mL) was added KOH (50.0 g, 892.8 mmol) and H₂O (100 mL). The mixture was stirred at 90° C. for 16 hours. The reaction mixture was quenched with 6 N HCl to adjust pH to 5~6, extracted with ethyl acetate (200 mL*3). The organic layer was dried over Na₂SO₄, filtered and concentrated. The residue was purified by flash silica chromatography, elution gradient 0 to 10% MeOH in DCM to give the desired compound as a yellow solid (9.0 g, 89%).

4). Synthesis of Compound (113-4)

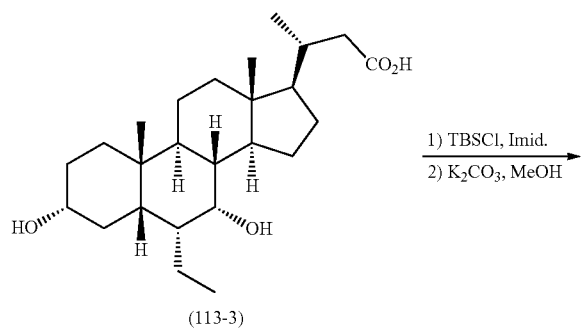

(113-3)

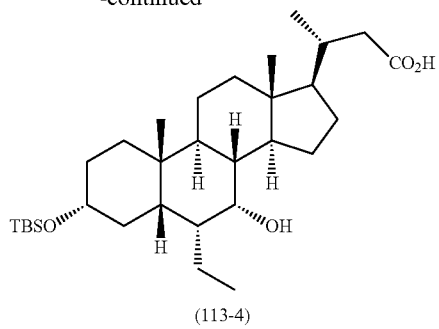

(113-4)

Into a solution of (113-3) (5.0 g, 12.3 mmol) in THF (200 mL) was added Imidazole (5.9 g, 86.1 mmol) and TBSCl (5.6 g, 36.9 mmol). The mixture was stirred at rt for 16 hours. The reaction mixture was quenched with 10% citric acid solution to adjust pH to 5~6, extracted with ethyl acetate (150 mL*3). The organic layer was dried over Na₂SO₄, filtered and concentrated to give crude product (7.2 g, crude) as a yellow solid. To the yellow solid in CH₃OH (250 mL) was added K₂CO₃ (2.3 g, 17.0 mmol). The mixture was stirred at rt for 4 hours. The reaction mixture was quenched with 10% citric acid solution to adjust pH to 5-6, extracted with ethyl acetate (150 mL*3). The organic layer was dried over Na₂SO₄, filtered and concentrated. The residue was purified by flash silica chromatography, elution gradient 10 to 20% EtOAc in petroleum ether to give the desired compound as a yellow solid (3.3 g, 56%).

5). Synthesis of Compound (113-5)

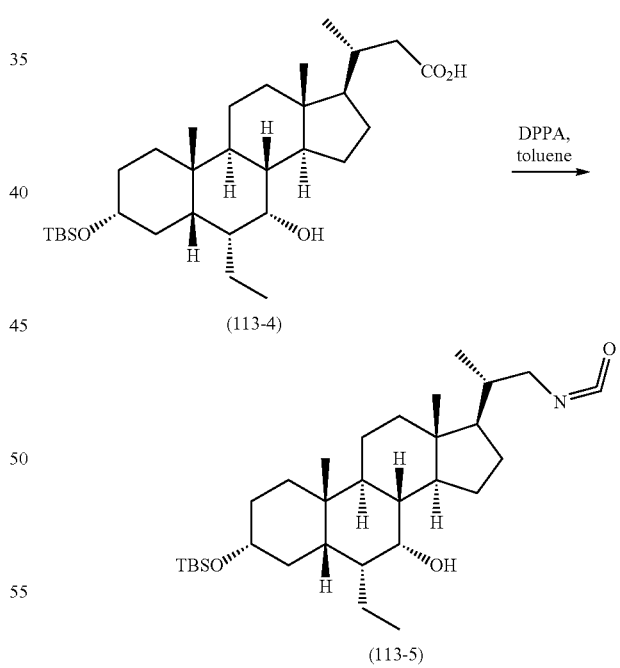

Into a solution of (113-4) (1.0 g, 2.0 mmol) in toluene (10 mL) was added TEA (4.2 mmol, 2.1 eq) and DPPA (2.1 mmol, 1.05 eq) sequentially at 0° C. The resulting mixture was stirred at 0° C. for 1 hour. Then was warmed to 100° C. and stirred for 5 hours. After being cooled to rt, a 0.2 M solution of compound (113-5) in toluene was obtained, which can be divided into several portions for the next step reaction.

6). Synthesis of Example 113

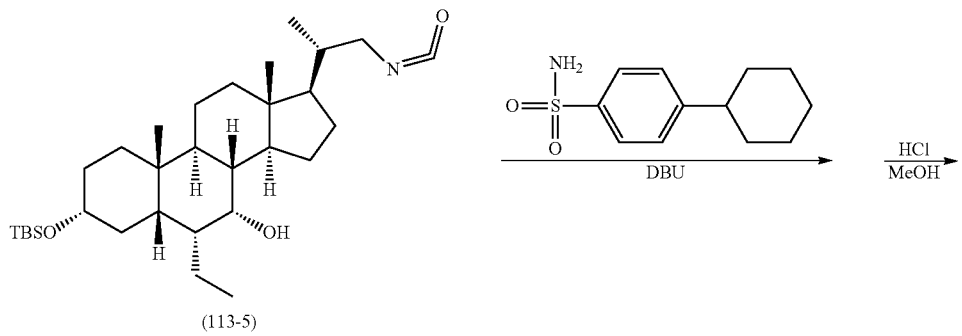

(113-5)

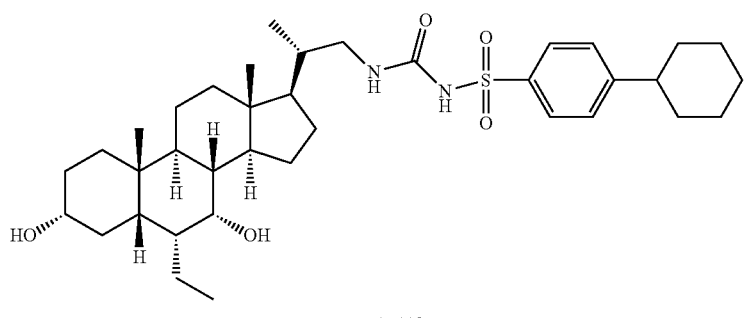

example 113

Cyclohexylbenzenesulfonamide (72 mg, 0.3 mmol) and DBU (0.153 g, 1 mmol) in THF (1 mL) was added into a solution of PH-ETA-C-005-5 (1 mL, 0.2 mmol) in toluene. The mixture was stirred at rt for overnight. The mixture was quenched with water, extracted with ethyl acetate (20 mL*3), dried over $Na_2SO_4$, filtered, and concentrated. The residue was dissolved in MeOH (2 mL), Then 1 drop of 37% HCl was added. The mixture was stirred at rt for 10 minutes. Then the mixture was diluted with ethyl acetate (50 mL) and washed sequentially with saturated sodium bicarbonate and brine. The organic layer was dried over $Na_2SO_4$, filtered and concentrated. The residue was purified by Flash-Prep-HPLC ((IntelFlash-1): Column, C18; mobile layer, $MeCN/H_2O$, Detector, UV 254 nm) to give the example 113 as a white solid (44.7 mg).

Example 114

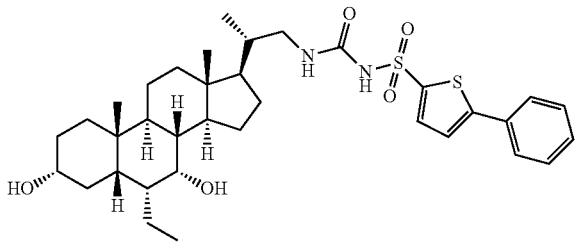

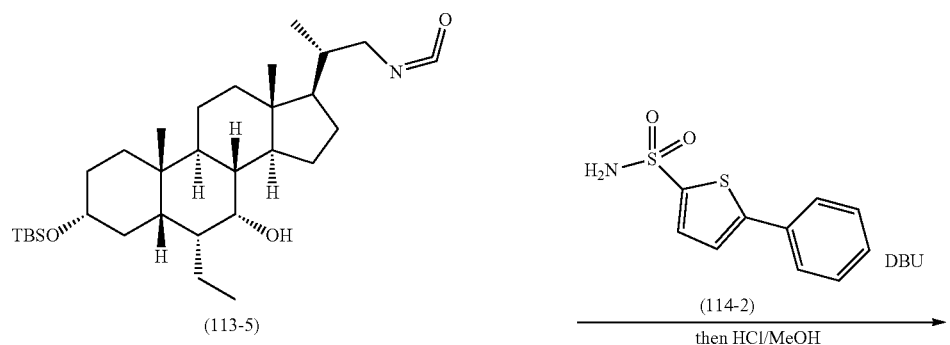

(113-5)             (114-2)

117 118

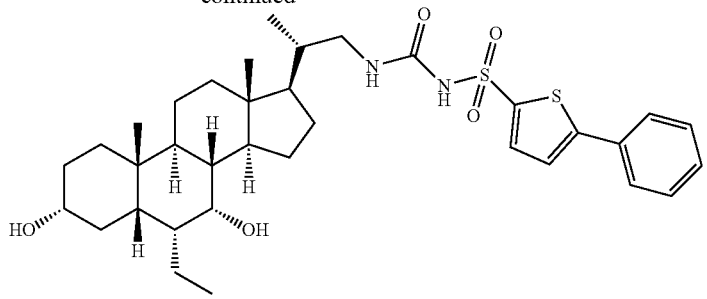

example 114

Compound (114-2) (71.7 mg, 0.3 mmol) and DBU (0.153 g, 1 mmol) in THF (1 mL) was added into a solution of (113-5) (1 mL, 0.2 mmol) in toluene. The mixture was stirred at rt overnight. The mixture was quenched with water, extracted with ethyl acetate (50 mL), dried over $Na_2SO_4$, filtered, and concentrated. The residue was dissolved in MeOH (2 mL), Then 1 drop of 37% HCl was added. The mixture was stirred at rt for 10 minutes. then was diluted with ethyl acetate (50 mL) and washed sequentially with saturated sodium bicarbonate and brine. The organic layer was dried over $Na_2SO_4$, filtered and concentrated. The residue was purified by Flash-Prep-HPLC ((IntelFlash-1): Column, C18; mobile phase, MeCN/$H_2O$, Detector, UV 254 nm) to give example 114 as a white solid (12.7 mg).

Example 115

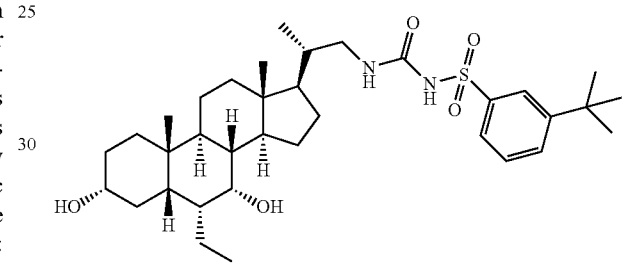

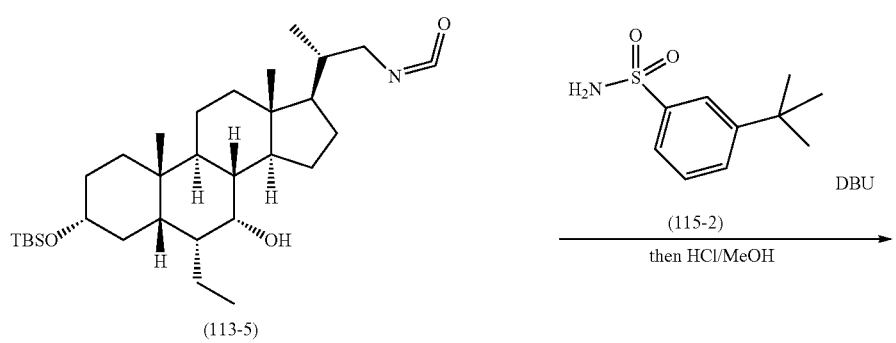

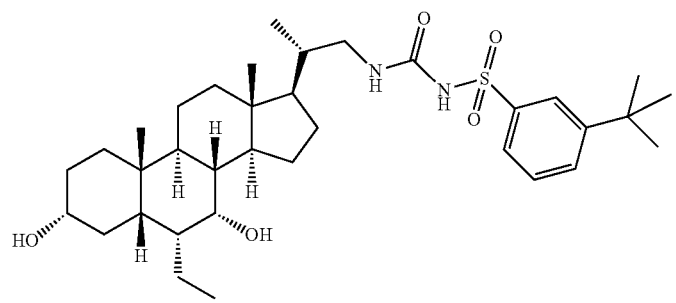

example 115

Compound (115-2) (63.9 mg, 0.3 mmol) and DBU (0.153 g, 1 mmol) in THF (1 mL) was added into a solution of (113-5) (1 mL, 0.2 mmol) in toluene. The mixture was stirred at rt overnight. The mixture was quenched with water, extracted with ethyl acetate (50 mL), dried over $Na_2SO_4$, filtered, and concentrated. The residue was dissolved in MeOH (2 mL), then 1 drop of 37% HCl was added. The mixture was stirred at rt for 10 minutes. Then was diluted with ethyl acetate (50 mL) and washed sequentially with saturated sodium bicarbonate and brine. The organic layer was dried over $Na_2SO_4$, filtered and concentrated. The residue was purified by Flash-Prep-HPLC ((IntelFlash-1): Column, C18; mobile phase, $MeCN/H_2O$, Detector, UV 254 nm) to give example 115 as a white solid (25.9 mg).

Example 116

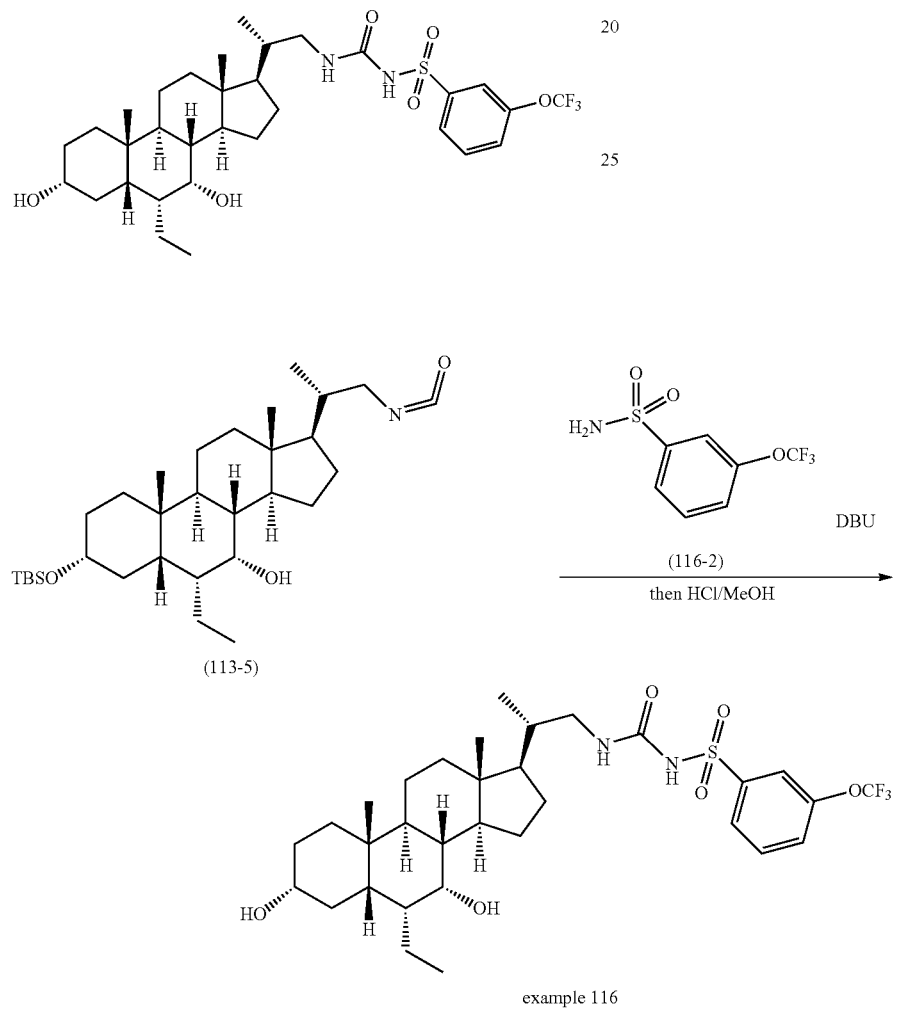

Compound (116-2) (72.3 mg, 0.3 mmol) and DBU (0.153 g, 1 mmol) in THF (1 mL) was added into a solution of (113-5) (1 mL, 0.2 mmol) in toluene. The mixture was stirred at rt overnight. The mixture was quenched with water, extracted with ethyl acetate (50 mL), dried over $Na_2SO_4$, filtered, and concentrated. The residue was dissolved in MeOH (2 mL), then 1 drop of 37% HCl was added. The mixture was stirred at rt for 10 minutes. Then was diluted with ethyl acetate (50 mL) and washed sequentially with saturated sodium bicarbonate and brine. The organic layer was dried over $Na_2SO_4$, filtered and concentrated. The residue was purified by Flash-Prep-HPLC ((IntelFlash-1): Column, C18; mobile phase, $MeCN/H_2O$, Detector, UV 254 nm) to give example 116 as a white solid (24.2 mg).

Example 117

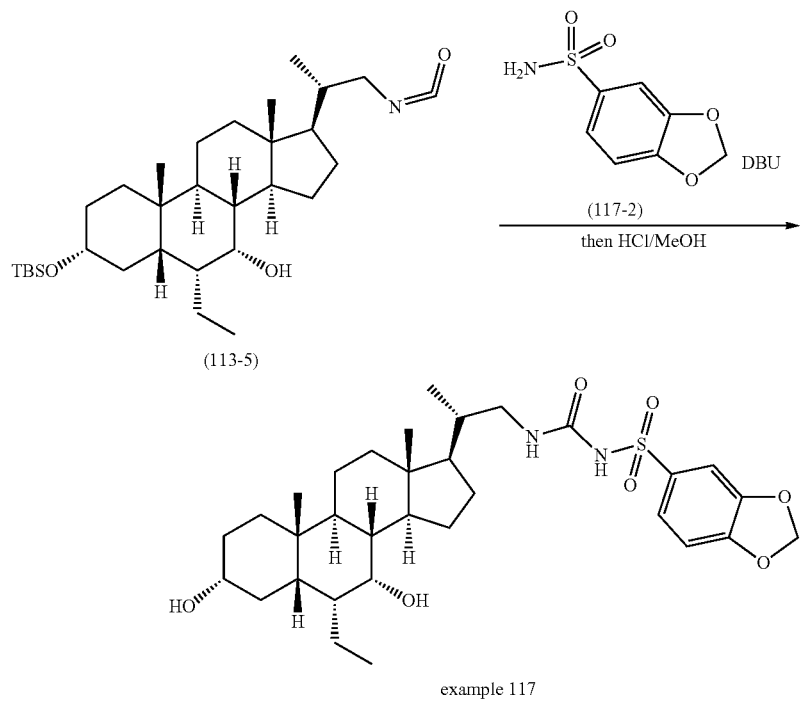

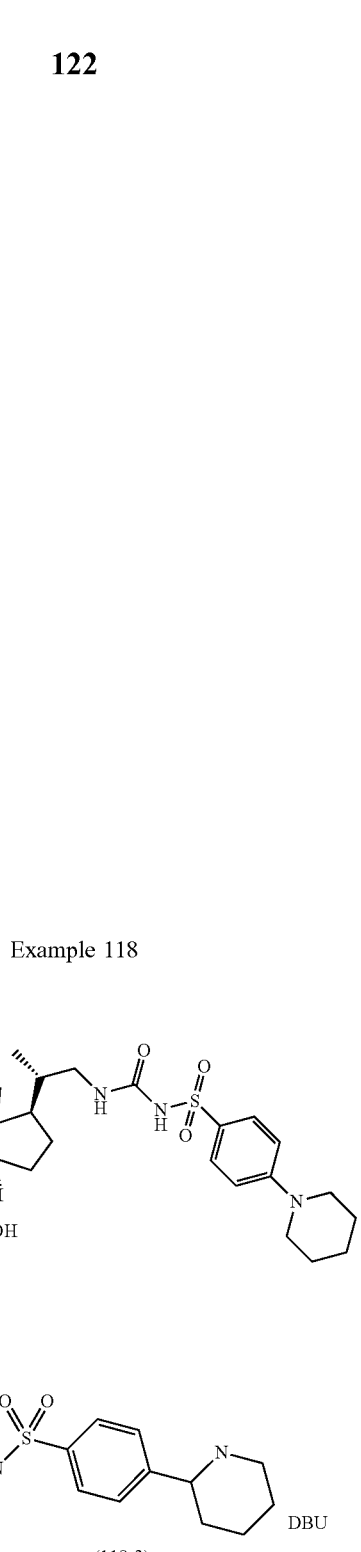

Compound (117-2) (60.3 mg, 0.3 mmol) and DBU (0.153 g, 1 mmol) in THF (1 mL) was added into a solution of (113-5) (1 mL, 0.2 mmol) in toluene. The mixture was stirred at rt overnight. The mixture was quenched with water, extracted with ethyl acetate (50 mL), dried over $Na_2SO_4$, filtered, and concentrated. The residue was dissolved in MeOH (2 mL), Then 1 drop of 37% HCl was added. The mixture was stirred at rt for 10 minutes. Then was diluted with ethyl acetate (50 mL) and washed sequentially with saturated sodium bicarbonate and brine. The organic layer was dried over $Na_2SO_4$, filtered and concentrated. The residue was purified by Flash-Prep-HPLC ((IntelFlash-1): Column, C18; mobile phase, $MeCN/H_2O$, Detector, UV 254 nm) to give example 117 as a white solid (32.8 mg).

Example 118

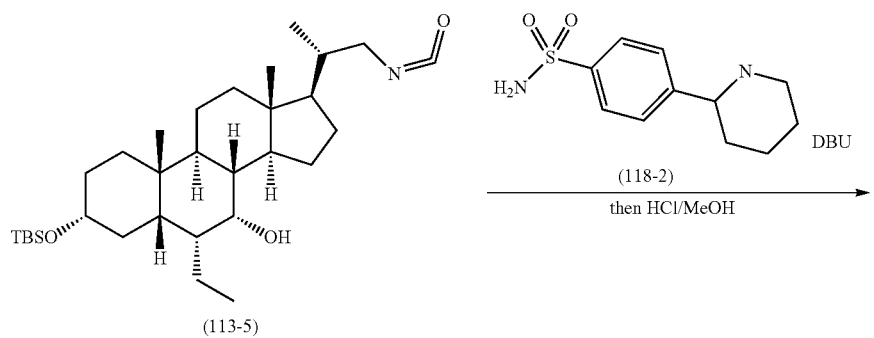

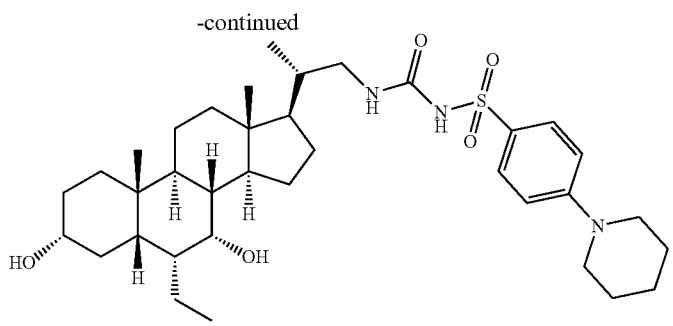

example 118

Compound (118-2) (72 mg, 0.3 mmol) and DBU (0.153 g, 1 mmol) in THF (5 mL) was added into a solution of (113-5) (1 mL, 0.2 mmol) in toluene. The mixture was stirred at rt overnight. The mixture was quenched with water, extracted with ethyl acetate (20 mL*3), dried over $Na_2SO_4$, filtered, and concentrated. The residue was dissolved in MeOH (2 mL), then 1 drop of 37% HCl was added. The mixture was stirred at rt for 10 minutes, then was diluted with ethyl acetate (50 mL) and washed sequentially with saturated sodium bicarbonate and brine. The organic layer was dried over $Na_2SO_4$, filtered and concentrated. The residue was purified by Flash-Prep-HPLC ((IntelFlash-1): Column, C18; mobile phase, MeCN/$H_2O$, Detector, UV 254 nm) to give the example 118 as a white solid (40 mg).

Example 119

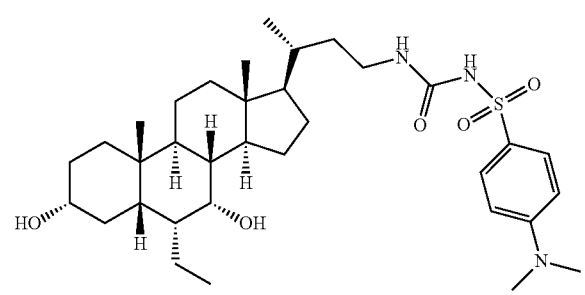

1. Synthesis of Compound (119-1)

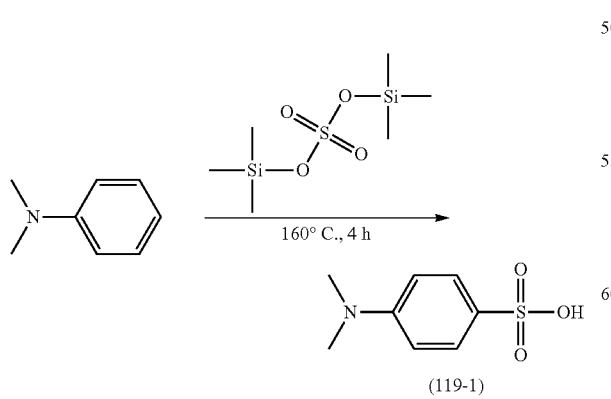

A mixture of N,N-dimethylaniline (0.5 g, 4.13 mmol) and bistrimethylsilyl sulfate (0.5 g, 4.13 mmol) was heated at 160° C. for 5 hours. The mixture was allowed to cool to rt and the resulting solid was isolated by filtration and washed with $Et_2O$. The solid was then dissolved in $H_2O$, and the solution was concentrated in vacuo to give the title compound 600 mg (crude) as a white solid.

2). Synthesis of Compound (119-2)

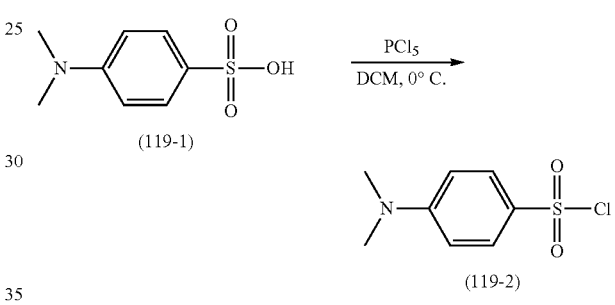

Compound (119-1) (600 mg) was added portionwise to a suspension of $PCl_5$ (931 mg, 4.5 mmol) in DCM (20 mL) at 0° C. The mixture was then allowed to warm to rt and was then stirred at rt for 3 h. The mixture was concentrated in vacuo and the residue was dissolved in $Et_2O$ and $H_2O$. The layers were separated and the organic layer was dried over $Na_2SO_4$, filtered and concentrated in vacuo to give the title compound 320 mg as a yellow solid, which was used directly without further purification.

3). Synthesis of Compound (119-3)

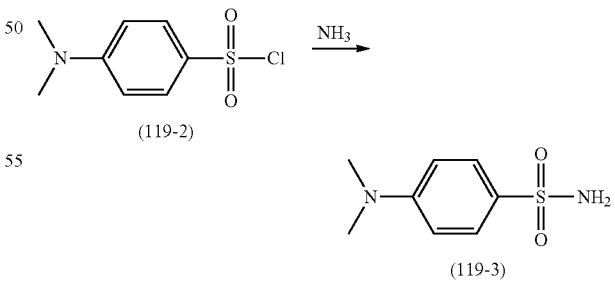

Ammonia (10 mL) was added to a solution of (119-2) (320 mg) in THF (10 mL) and was stirred at rt for 1.5 h, then concentrated. The residue was purified by flash silica chromatography, elution gradient 40 to 100% EtOAc in petroleum ether to give the title compound (160 mg, 54.7%) as a yellow solid.

4). Synthesis of Example 119

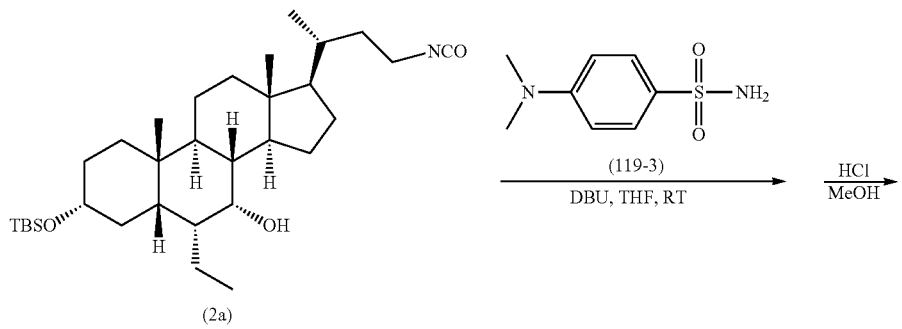

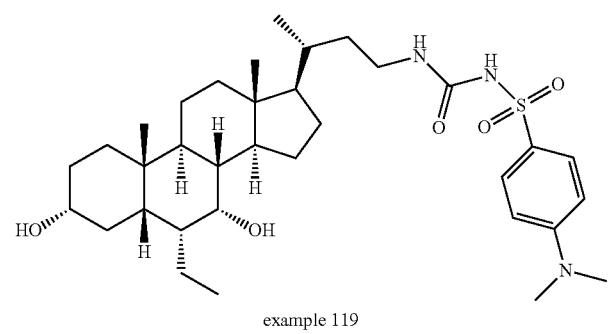

example 119

Compound (119-3) (100 mg, 0.5 mmol) and DBU (76 mg, 0.5 mmol) in THF (5 mL) was added into a solution of the compound (2a) (1 mL, 0.2 mmol) in toluene. The mixture was stirred at RT for overnight. The mixture was quenched with water, extracted with ethyl acetate (50 mL), dried, filtered, and concentrated. The residue was dissolved in MeOH (2 mL), then 1 drop of 37% HCl was added. The mixture was stirred at rt for 10 minutes, then was diluted with ethyl acetate (50 mL) and washed sequentially with saturated sodium bicarbonate and brine. The organic layer was dried over $Na_2SO_4$, filtered and concentrated. The residue was purified by Flash-Prep-HPLC ((IntelFlash-1): Column, C18; mobile phase, MeCN/$H_2O$, Detector, UV 220 nm) to give the example 119 (24.3 mg) as a white solid.

Example 121

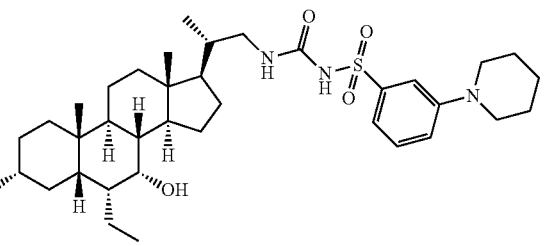

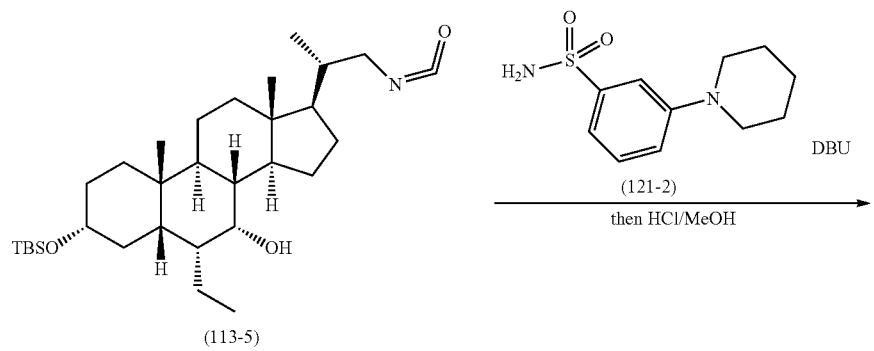

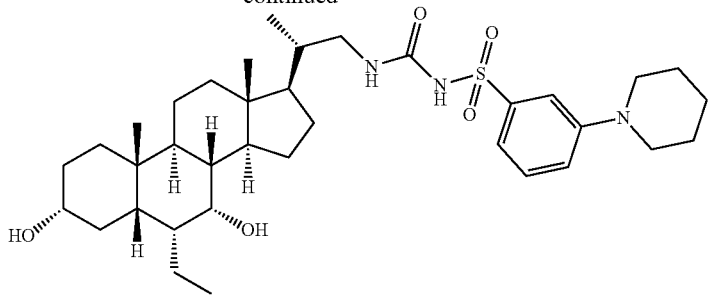

example 121

Compound (121-2) (72 mg, 0.3 mmol) and DBU (0.153 g, 1 mmol) in THF (1 mL) was added into a solution of (93-5) (1 mL, 0.2 mmol) in toluene. The mixture was stirred at rt overnight. The mixture was quenched with water, extracted with ethyl acetate (50 mL), dried over Na$_2$SO$_4$, filtered, and concentrated. The residue was dissolved in MeOH (2 mL). Then 1 drop of 37% HCl was added. The mixture was stirred at rt for 10 minutes. Then was diluted with ethyl acetate (50 mL) and washed sequentially with saturated sodium bicarbonate and brine. The organic layer was dried over Na$_2$SO$_4$, filtered and concentrated. The residue was purified by Flash-Prep-HPLC ((IntelFlash-1): Column, C18; mobile phase, MeCN/H$_2$O, Detector, UV 254 nm) to give example 121 as a white solid (29.7 mg). The following desired examples were prepared using procedures similar to that described above. The MS data and 1H NMR data are delineated in Table 11.

TABLE 11

| Example # | Structure | MS data (M − 1)$^-$ | $^1$H NMR (500 MHz) |
|---|---|---|---|
| 12 | 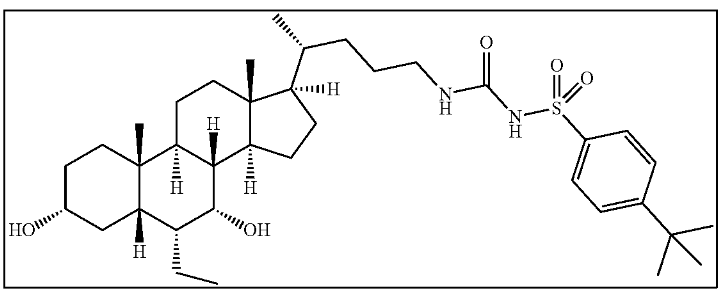 | 643.31 | |
| 13 | 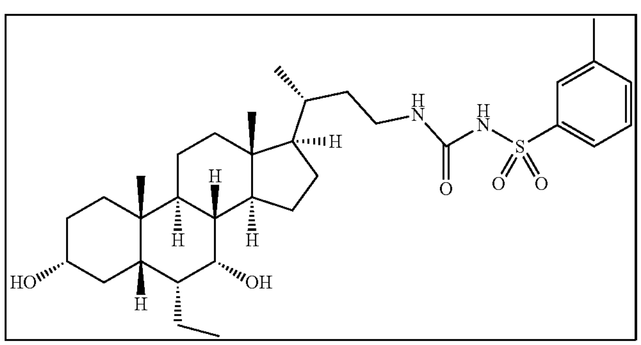 | 587.29 | (CDCl$_3$) 7.69 (2H, br s), 7.45 (2H, m), 7.10 (1H, br s), 6.52 (1H, s), 3.71 (1H, s), 3.41 (1H, br s), 3.30 (1H, br s), 3.17 (1H, br s), 2.45 (3H, s), 0.95 (3H, d, J = 5.5 Hz), 0.90 (3H, s), 0.65 (3H, s). |

TABLE 11-continued

| Example # | Structure | MS data (M − 1)⁻ | ¹H NMR (500 MHz) |
|---|---|---|---|
| 14 | 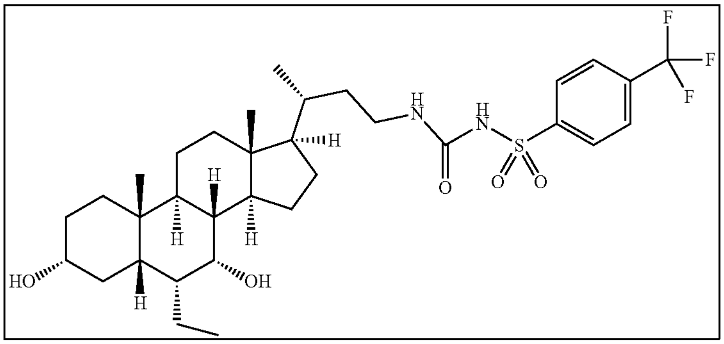 | 641.24 | (CDCl₃) 8.15 (1H, br s), 8.04 (2H, d, J = 8.0 Hz), 7.82 (2H, d, J = 8.0 Hz), 6.43 (1H, s), 3.71 (1H, s), 3.42 (1H, br s), 3.30 (1H, br s), 3.18 (1H, br s), 0.95 (3H, d, J = 5.5 Hz), 0.90 (3H, s), 0.64 (3H, s). |
| 15 | 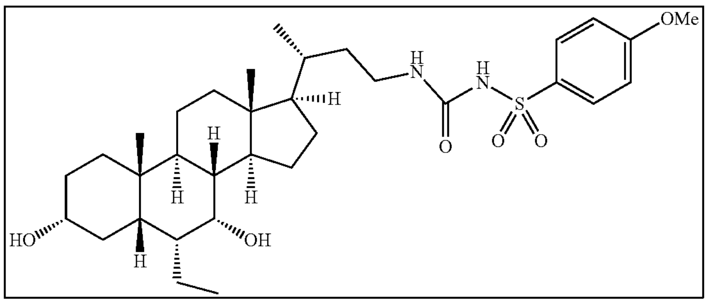 | 603.25 | (CDCl₃) 7.82 (2H, d, J = 9.0 Hz), 7.41 (1H, br s), 6.99 (2H, d, J = 9.0 Hz), 6.48 (1H, s), 3.89 (3H, s), 3.71 (1H, s), 3.41 (1H, br s), 3.29 (1H, br s), 3.17 (1H, br s), 0.95 (3H, d, J = 5.5 Hz), 0.90 (3H, s), 0.65 (3H, s). |
| 16 | 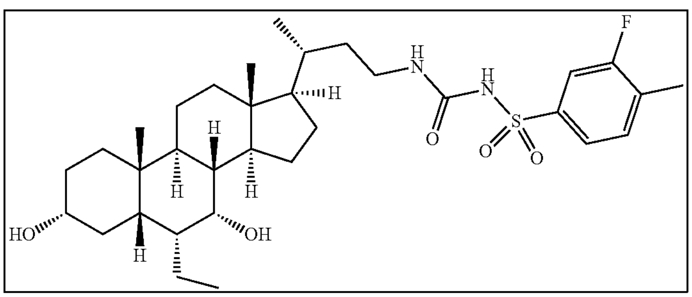 | 605.26 | (CDCl₃) 7.76 (1H, br s), 7.58 (1H, d, J = 9.5 Hz), 7.53 (1H, d, J = 9.5 Hz), 7.37 (1H, t, J = 7.5 Hz), 6.47 (1H, s), 3.71 (1H, s), 3.41 (1H, br s), 3.30 (1H, br s), 3.18 (1H, br s), 2.37 (3H, s), 0.95 (3H, d, J = 5.5 Hz), 0.90 (3H, s), 0.65 (3H, s). |
| 17 | 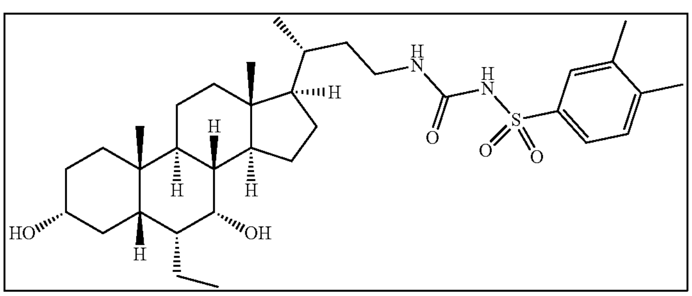 | 601.29 | (CDCl₃) 7.63 (1H, s), 7.60 (1H, d, J = 7.0 Hz), 7.29 (1H, d, J = 7.0 Hz), 7.18 (1H, br s), 6.51 (1H, s), 3.71 (1H, s), 3.41 (1H, br s), 3.29 (1H, br s), 3.17 (1H, br s), 2.35 (3H, s), 2.33 (3H, s), 0.95 (3H, d, J = 5.5 Hz), 0.90 (3H, s), 0.65 (3H, s). |
| 18 | 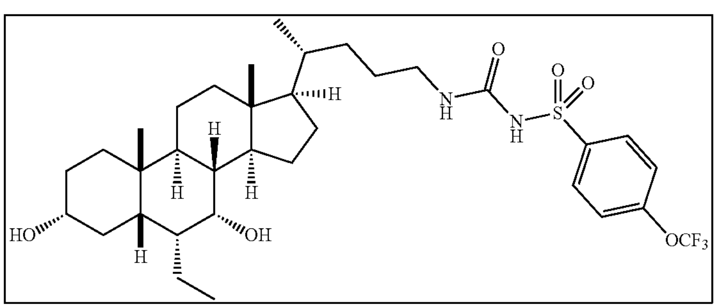 | 671.44 | |

TABLE 11-continued
| Example # | Structure | MS data (M − 1)⁻ | ¹H NMR (500 MHz) |
|---|---|---|---|
| 19 | 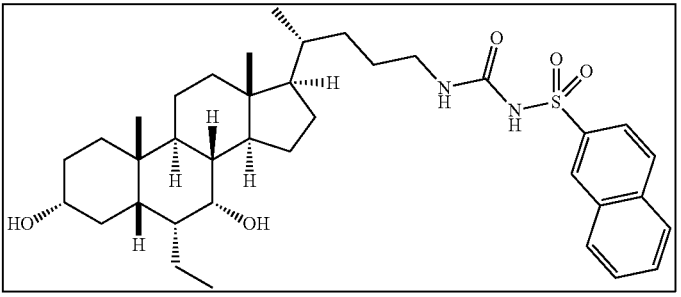 | 637.41 | |
| 20 | 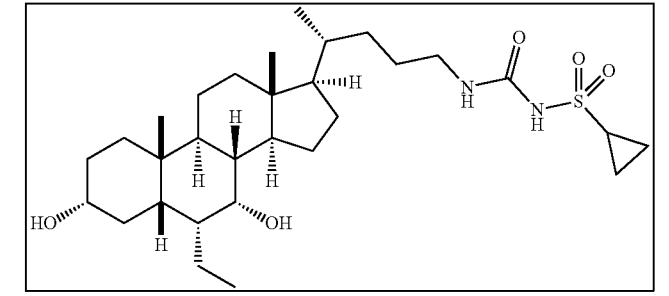 | 551.45 | |
| 21 | 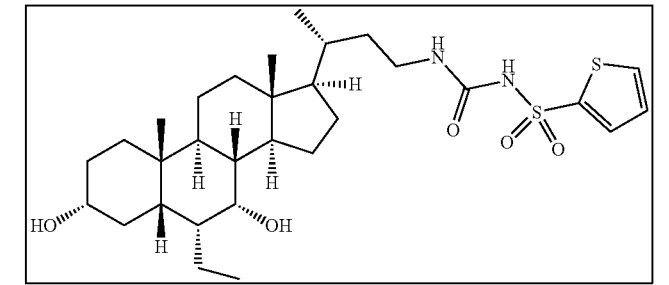 | 57.21 | (CDCl₃) 7.66 (2H, m), 7.41(1H, br s), 7.11 (1H, m), 6.48 (1H, s), 3.68 (1H, s), 3.39 (1H, br s), 3.31 (1H, br s), 3.19 (1H, br s), 2.37 (3H, s), 0.94 (3H, d, J = 5.5 Hz), 0.90 (3H, s), 0.64 (3H, s). |
| 22 | 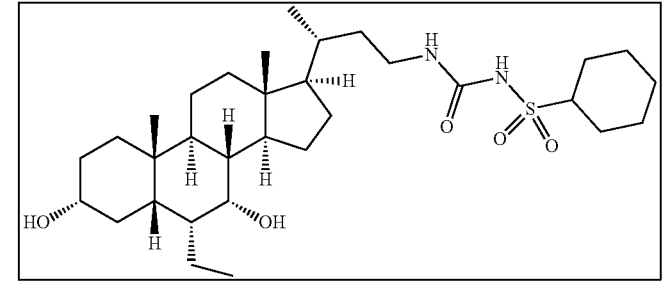 | 579.30 | (CDCl₃) 7.05 (1H, br s), 6.49 (1H, s), 3.68 (1H, s), 3.38 (1H, br s),3.30 (1H, br s), 3.19 (1H, br s), 3.05 (1H, m), 2.18 (2H, m), 0.95 (3H, d, J = 5.5 Hz), 0.90 (3H, s), 0.64 (3H, s). |
| 23 | 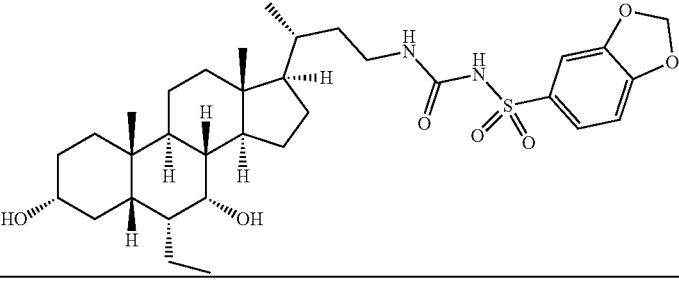 | 617.25 | (CDCl₃) 7.43 (1H, d, J = 9.5 Hz), 7.35 (1H, br s), 7.24 (1H, s), 6.87 (1H, d, J = 9.0 Hz), 6.44 (1H, s), 6.09 (2H, s), 3.68 (1H, s), 3.38 (1H, br s), 3.29 (1H, br s), 3.16 (1H, br s), 0.93 (3H, d, J = 5.5 Hz), 0.88 (3H, s), 0.64 (3H, s). |

TABLE 11-continued

| Example # | Structure | MS data (M − 1)⁻ | ¹H NMR (500 MHz) |
|---|---|---|---|
| 24 | 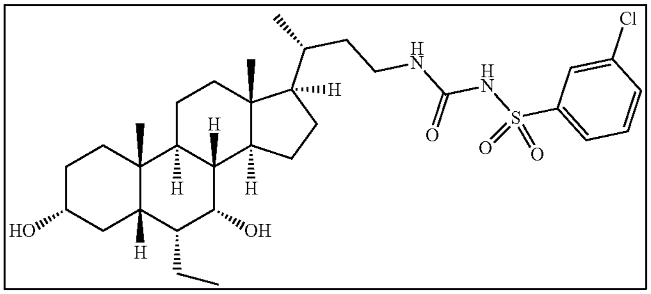 | 607.23 | (CDCl₃) 8.00 (1H, br s), 7.86 (1H, s), 7.76 (1H, d, J = 7.5 Hz), 7.60 (1H, d, J = 8.0 Hz), 7.47 (1H, t, J = 8.0 Hz), 6.45 (1H, s), 3.69 (1H, s), 3.39 (1H, br s), 3.29 (1H, br s), 3.17 (1H, br s), 0.93 (3H, d, J = 5.5 Hz), 0.88 (3H, s), 0.63 (3H, s). |
| 25 | 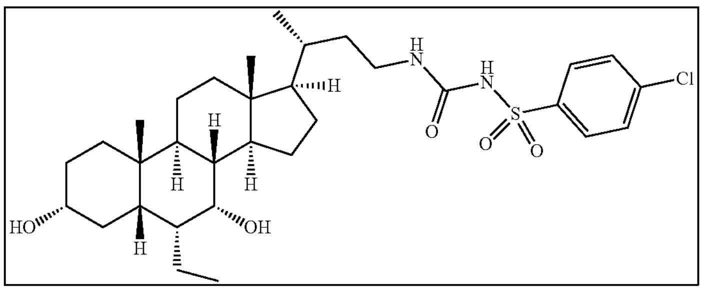 | 607.22 | (CDCl₃) 7.82 (1H, br s), 7.82 (2H, d, J = 7.5 Hz), 7.50 (2H, d, J = 7.5 Hz), 6.41 (1H, s), 3.69 (1H, s), 3.40 (1H, br s), 3.28 (1H, br s), 3.16 (1H, br s), 0.93 (3H, d, J = 6.0 Hz), 0.88 (3H, s), 0.63 (3H, s). |
| 26 | 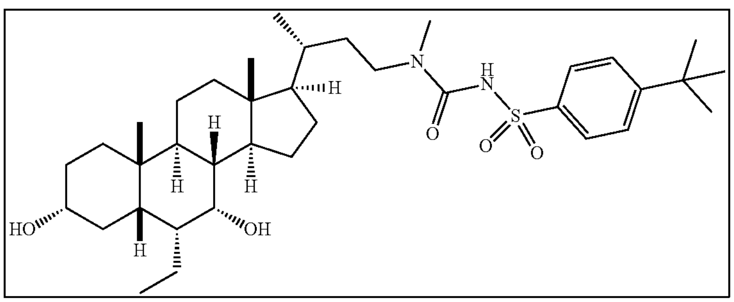 | 643.34 | |
| 27 | 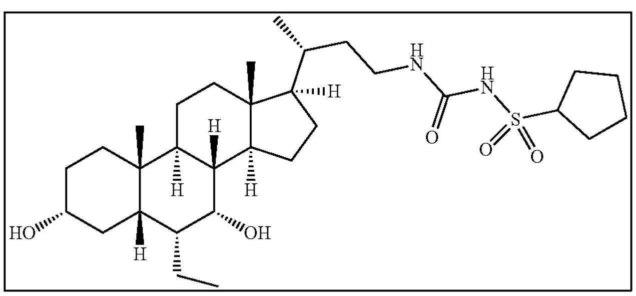 | 565.30 | (CDCl₃) 7.11 (1H, br s), 6.52 (1H, s), 3.71 (1H, s), 3.66 (1H, m), 3.41 (1H, br s), 3.34 (1H, br s), 3.22 (1H, br s), 2.07 (4H, m), 0.98 (3H, d, J = 5.5 Hz), 0.90 (3H, s), 0.66 (3H, s). |
| 28 | 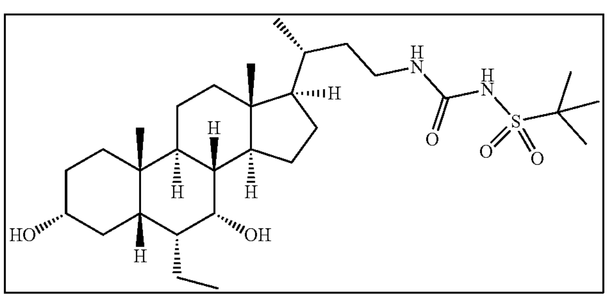 | 553.30 | (CDCl₃) 7.06 (1H, br s), 6.69 (1H, s), 3.71 (1H, s), 3.41 (1H, br s), 3.33 (1H, br s), 3.21 (1H, br s), 1.47 (9H, s), 0.97 (3H, d, J = 6.5 Hz), 0.90 (3H, s), 0.66 (3H, s). |

TABLE 11-continued

| Example # | Structure | MS data (M − 1)⁻ | ¹H NMR (500 MHz) |
|---|---|---|---|
| 29 | 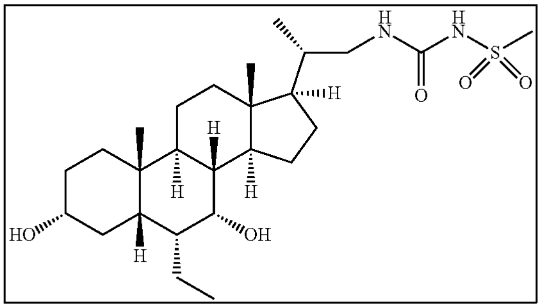 | 543.25 (M − 1 + HCO₂H) | |
| 30 | 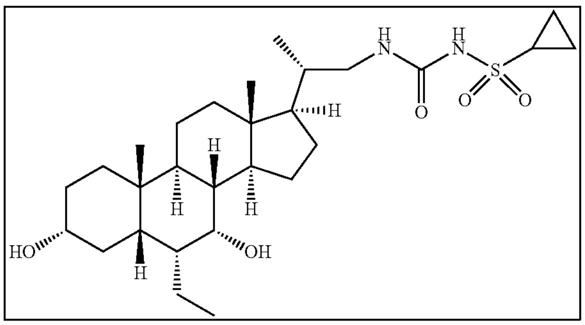 | 569.26 (M − 1 + HCO₂H) | |
| 31 | 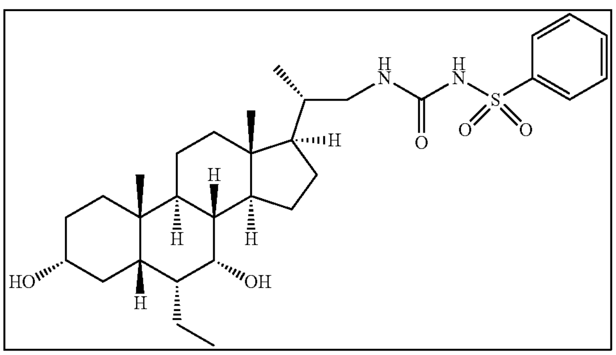 | 559.26 | |
| 32 | 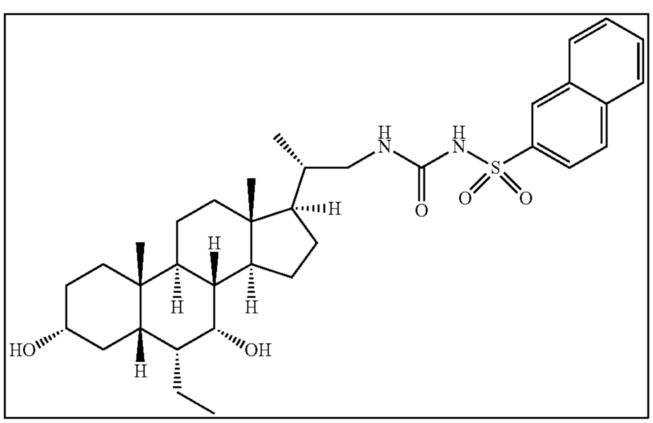 | 609.27 | |

TABLE 11-continued

| Example # | Structure | MS data (M − 1)⁻ | ¹H NMR (500 MHz) |
|---|---|---|---|
| 33 | 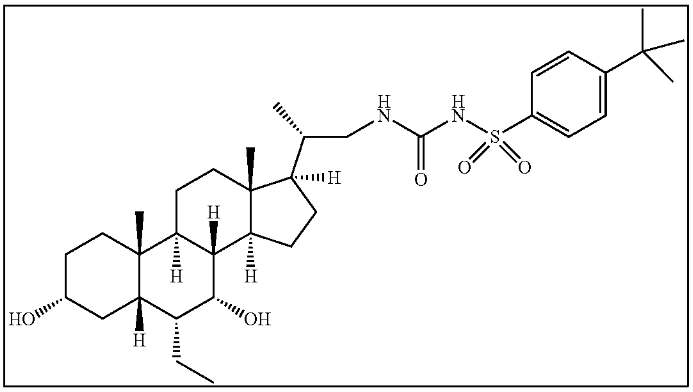 | 661.32 (M − 1 + HCO₂H) | |
| 34 | 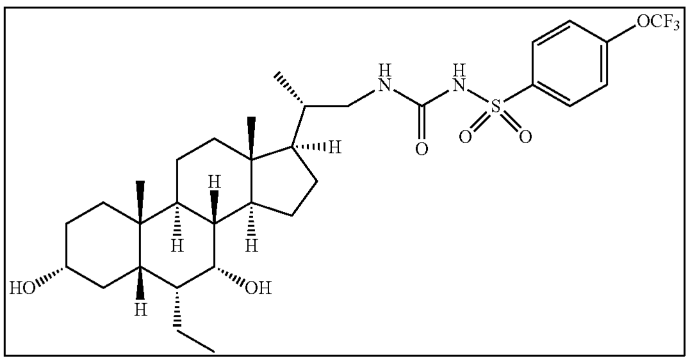 | 643.23 | |
| 35 | 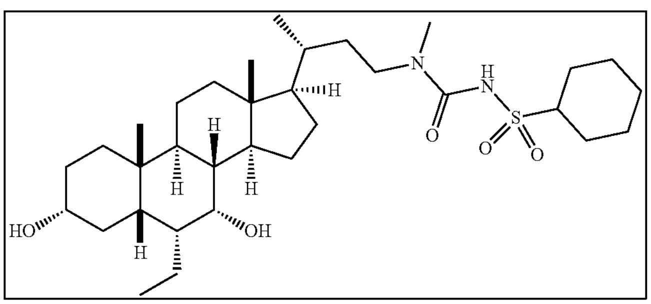 | 593.33 | |
| 36 | 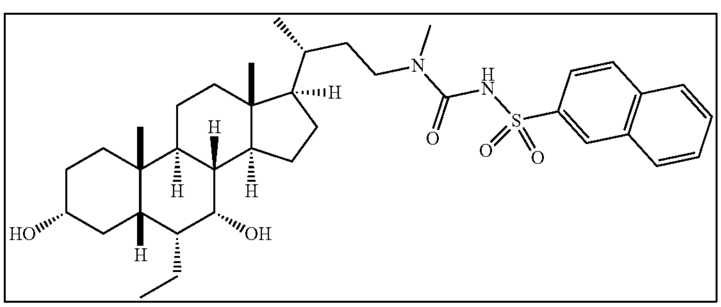 | 637.30 | |

TABLE 11-continued

| Example # | Structure | MS data (M − 1)⁻ | ¹H NMR (500 MHz) |
|---|---|---|---|
| 37 | 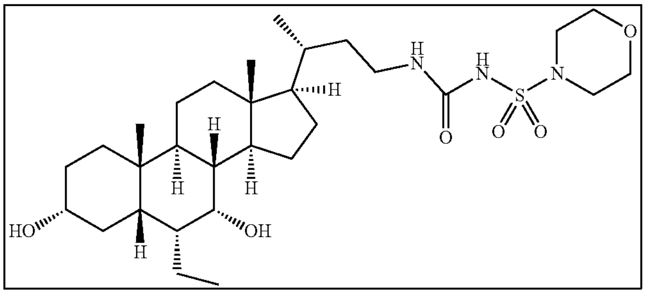 | 582.29 | (CDCl₃) 7.31 (1H, br s), 6.33 (1H, s), 3.78 (4H, s), 3.71 (1H, s), 3.41 (1H, br s), 3.34 (1H, br s), 3.26 (4H, s), 3.21 (1H, br s), 0.98 (3H, d, J = 6.5 Hz), 0.90 (3H, s), 0.66 (3H, s). |
| 38 | 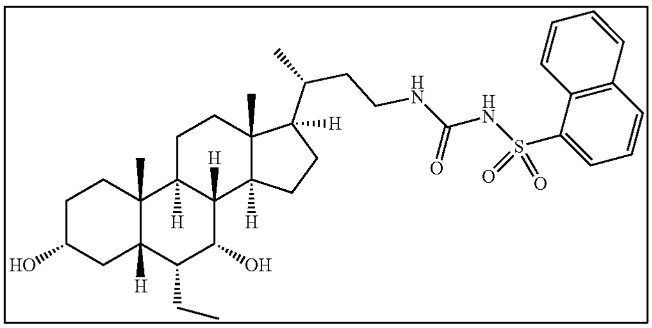 | 623.28 | (CDCl₃) 8.54 (1H, d, J = 9.0 Hz), 8.22 (1H, d, J = 7.5 Hz), 8.14 (1H, d, J = 8.0 Hz), 7.98 (1H, d, J = 7.0 Hz), 7.71 (1H, br s), 7.69 (1H, t, J = 7.0Hz), 7.64 (1H, t, J = 9.0Hz), 7.55 (1H, t, J = 7.5 Hz), 6.52 (1H, s), 3.71 (1H, s), 3.41 (1H, br s), 3.26 (1H, br s), 3.14 (1H, br s), 0.91 (3H, d, J = 6.0 Hz), 0.90 (3H, s), 0.62 (3H, s). |
| 39 | 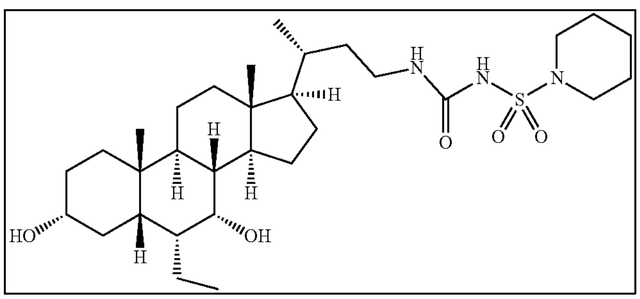 | 580.32 | (CDCl₃) 7.30 (1H, br s), 6.40 (1H, s), 3.71 (1H, s), 3.41 (1H, br s), 3.34 (1H, br s), 3.26 (4H, s), 3.23 (5H, m), 1.68 (4H, br s), 0.98 (3H, d, J = 6.5 Hz), 0.90 (3H, s), 0.66 (3H, s). |
| 40 | 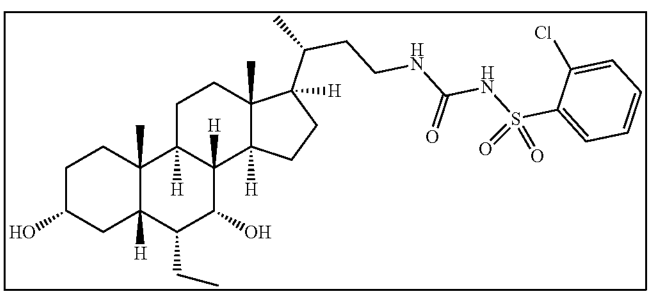 | 607.23 | |
| 41 | 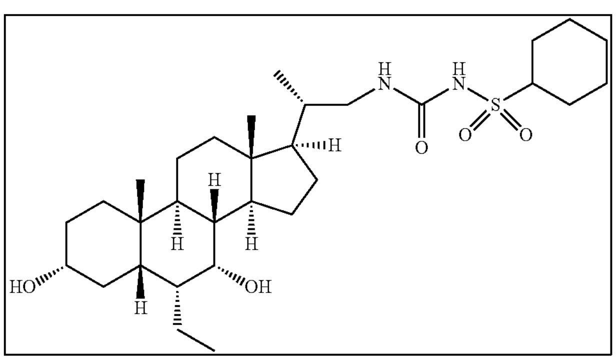 | 611.31 (M − 1 + HCO₂H) | |

TABLE 11-continued

| Example # | Structure | MS data (M − 1)⁻ | ¹H NMR (500 MHz) |
|---|---|---|---|
| 42 | 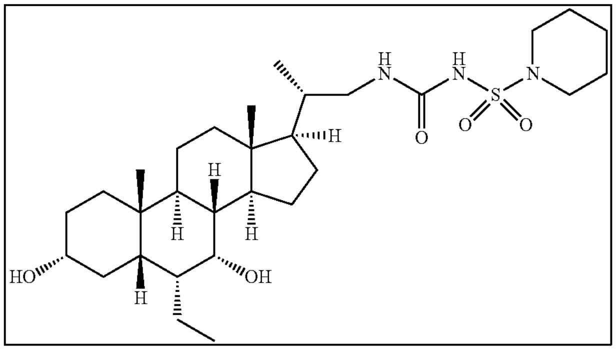 | 612.30 (M − 1 + HCO₂H) | |
| 43 | 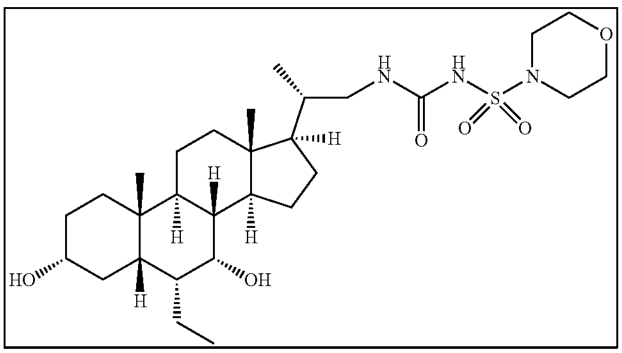 | 614.30 (M − 1 + HCO₂H) | |
| 44 | 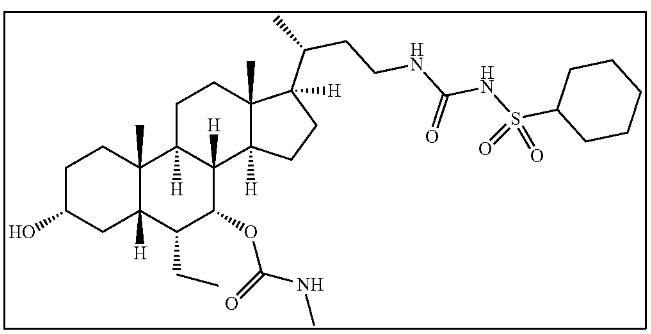 | 636.44 | |
| 45 | 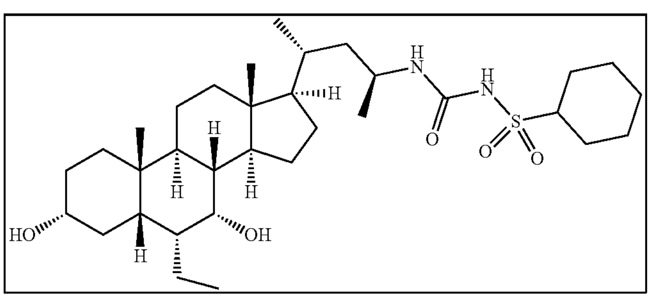 | 593.33 | |

US 10,696,713 B2
143                                                                                     144
TABLE 11-continued
| Example # | Structure | MS data (M − 1)⁻ | ¹H NMR (500 MHz) |
|---|---|---|---|
| 46 | 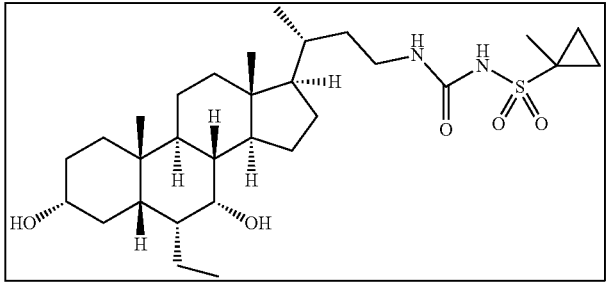 | 551.29 | |
| 47 | 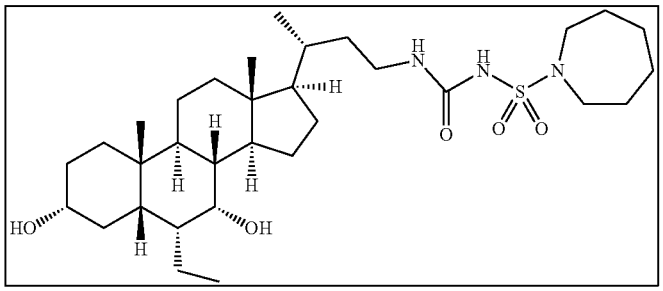 | 594.31 | |
| 48 | 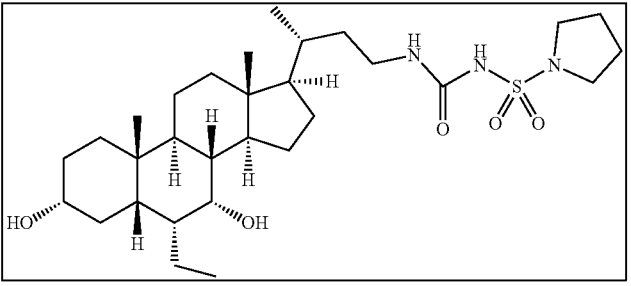 | 566.29 | |
| 49 | 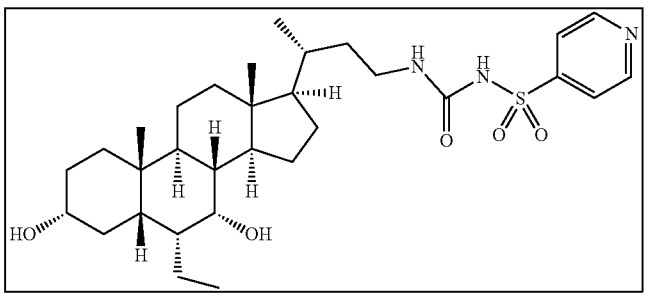 | 574.36 | |
| 50 | 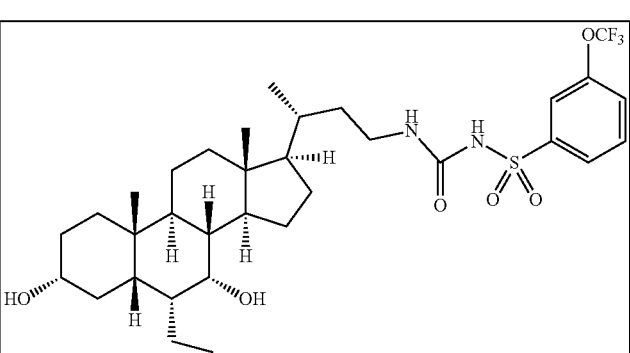 | 657.35 | |

TABLE 11-continued

| Example # | Structure | MS data (M − 1)⁻ | ¹H NMR (500 MHz) |
|---|---|---|---|
| 51 | 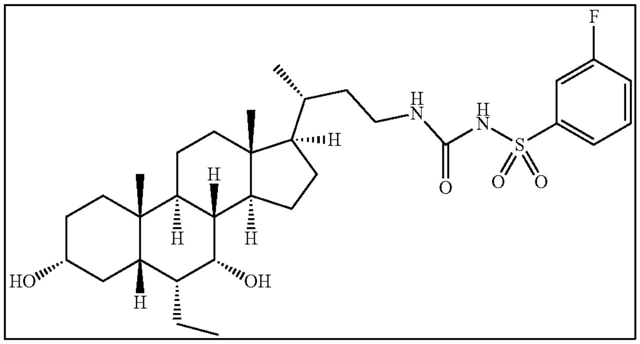 | 591.26 | |
| 52 | 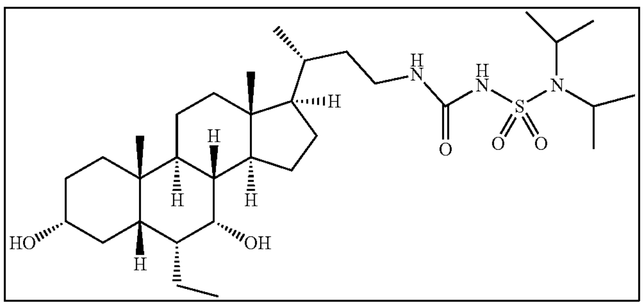 | 596.44 | |
| 53 | 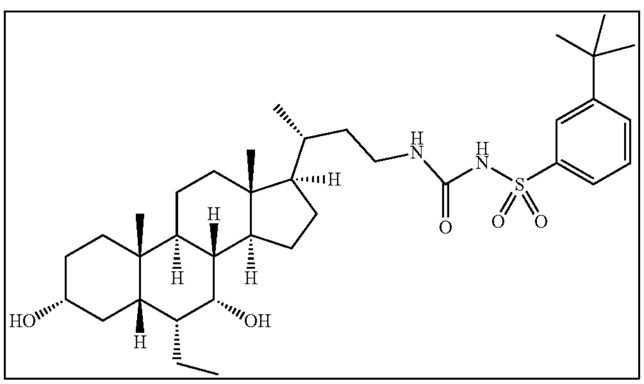 | 629.43 | |
| 54 | 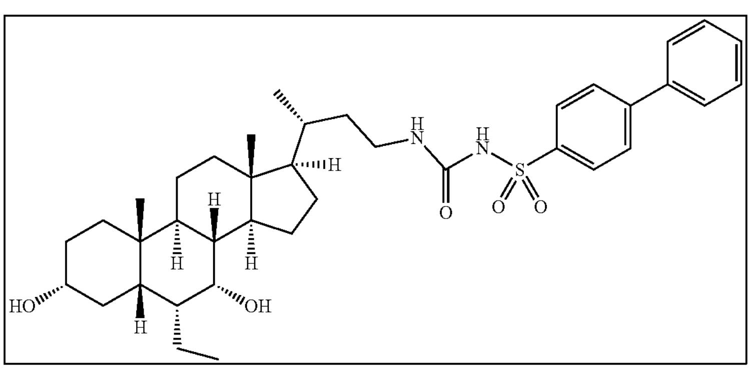 | 649.37 | |

TABLE 11-continued

| Example # | Structure | MS data (M − 1)⁻ | ¹H NMR (500 MHz) |
|---|---|---|---|
| 55 | 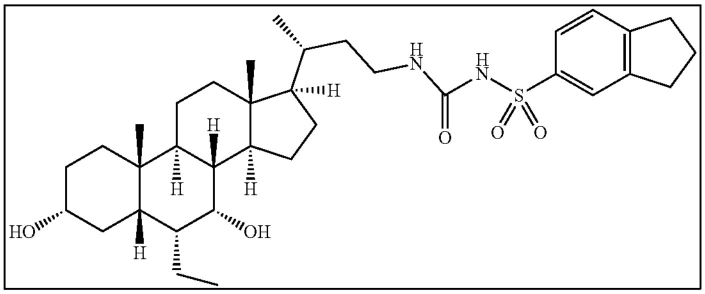 | 613.40 | |
| 56 | 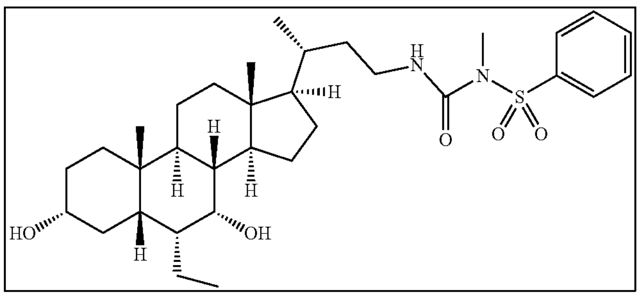 | 633.29 (M − 1 + HCO$_2$H) | |
| 57 | 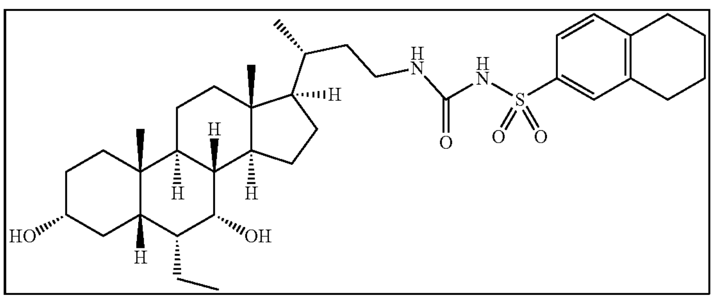 | 627.38 | |
| 58 | 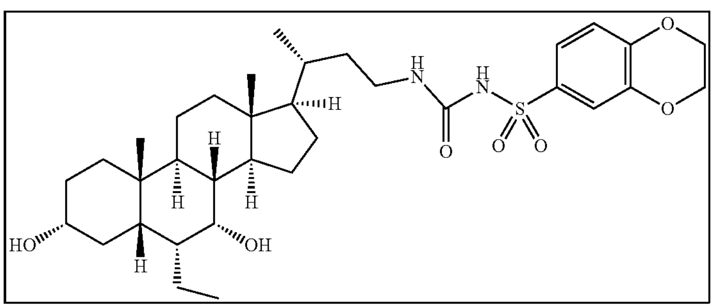 | 631.37 | |
| 59 | 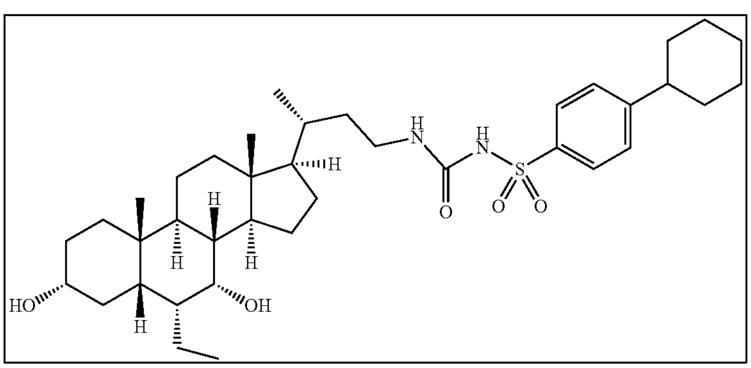 | 655.45 | |

TABLE 11-continued

| Example # | Structure | MS data (M − 1)⁻ | ¹H NMR (500 MHz) |
|---|---|---|---|
| 60 | 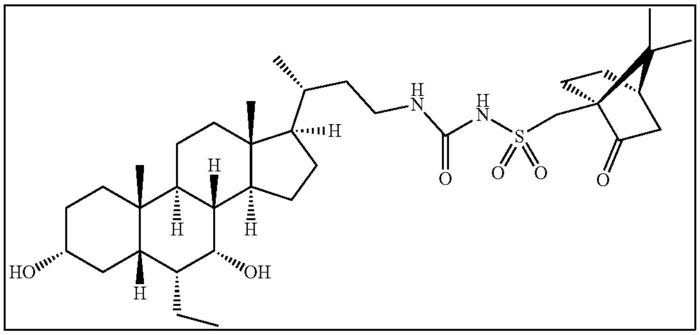 | 647.41 | |
| 61 | 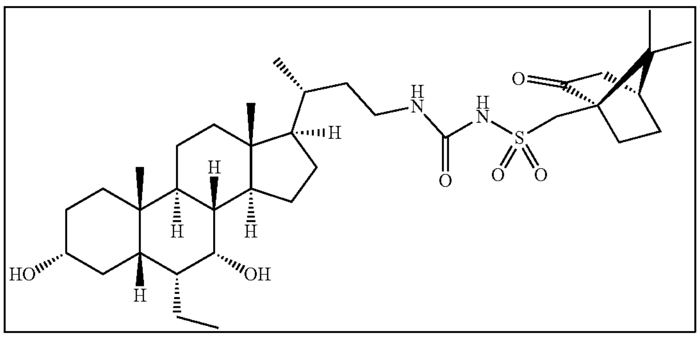 | 647.41 | |
| 62 | 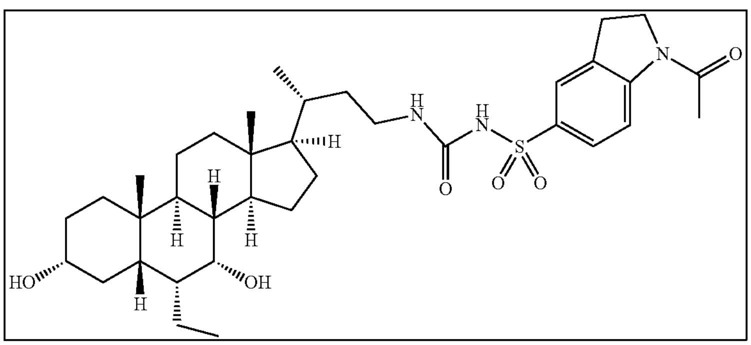 | 656.31 | |
| 63 | 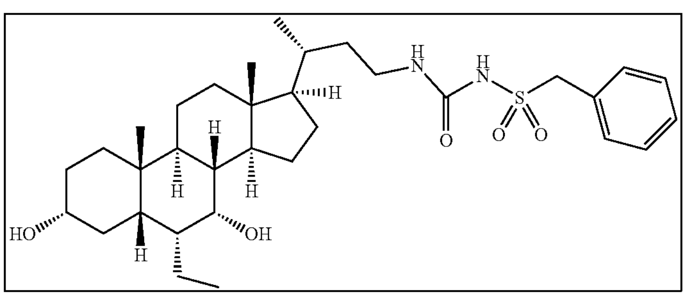 | 587.28 | |

TABLE 11-continued

| Example # | Structure | MS data (M − 1)⁻ | ¹H NMR (500 MHz) |
|---|---|---|---|
| 64 | 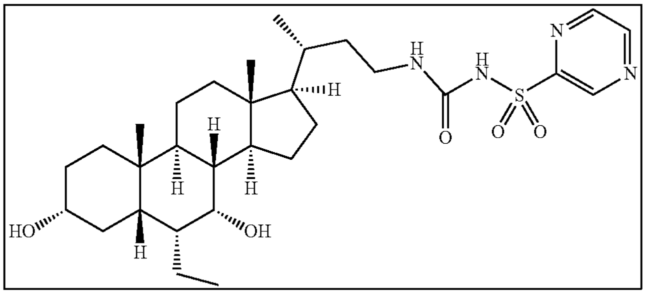 | 575.26 | |
| 65 | 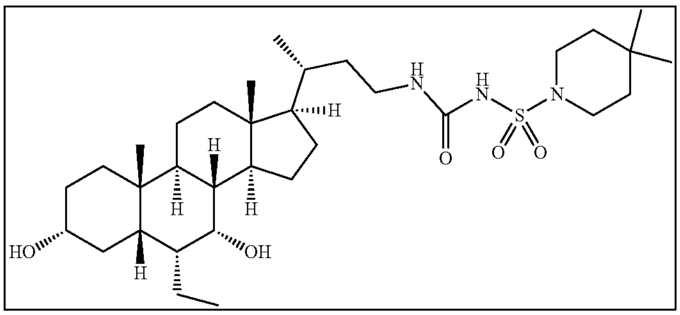 | 608.35 | |
| 66 | 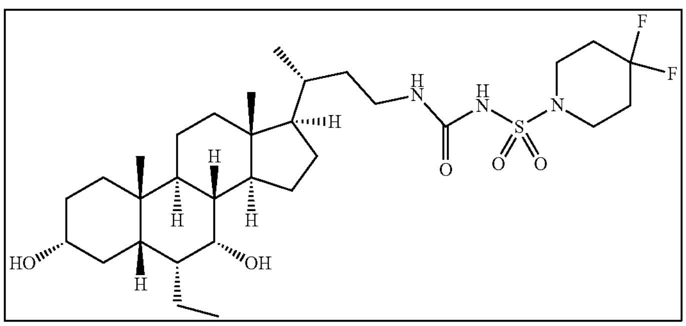 | 616.36 | |
| 67 | 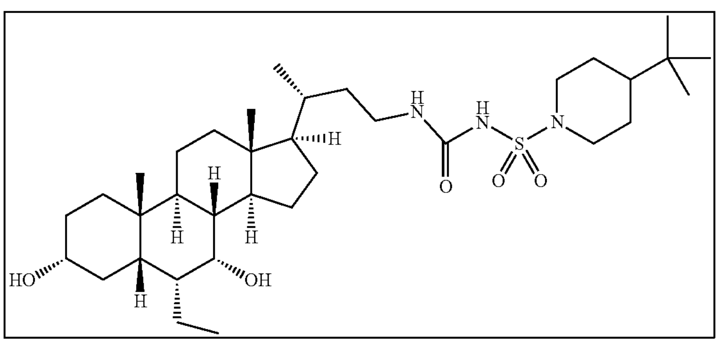 | 636.47 | |
| 68 | 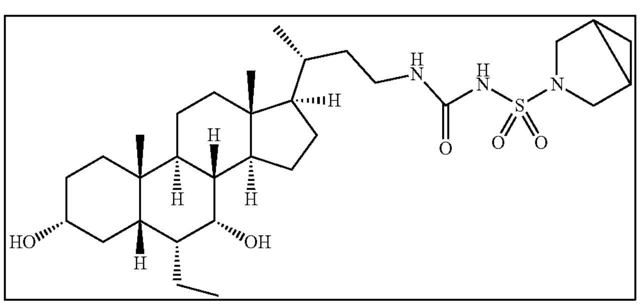 | 578.39 | |

TABLE 11-continued

| Example # | Structure | MS data (M − 1)⁻ | ¹H NMR (500 MHz) |
|---|---|---|---|
| 69 | 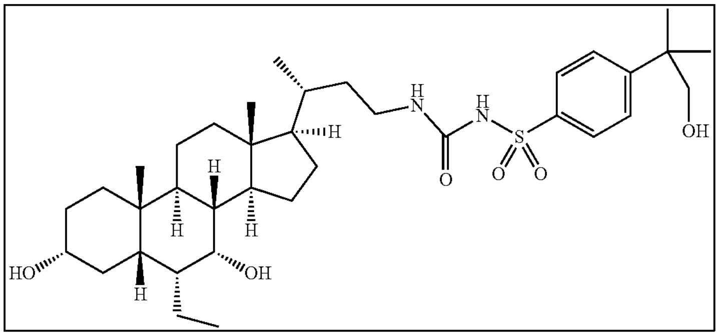 | 645.33 | |
| 70 | 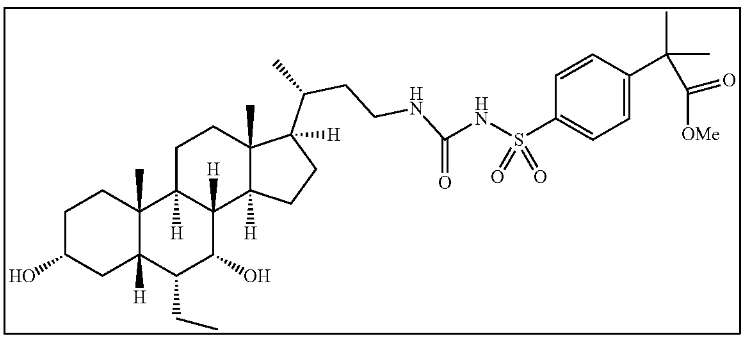 | 673.42 | |
| 71 | 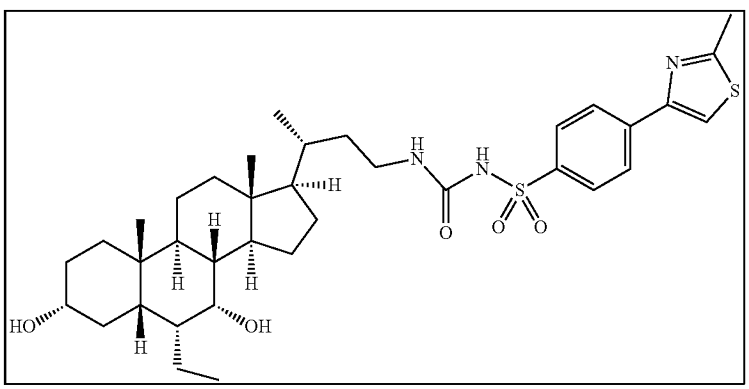 | 670.37 | |
| 72 | 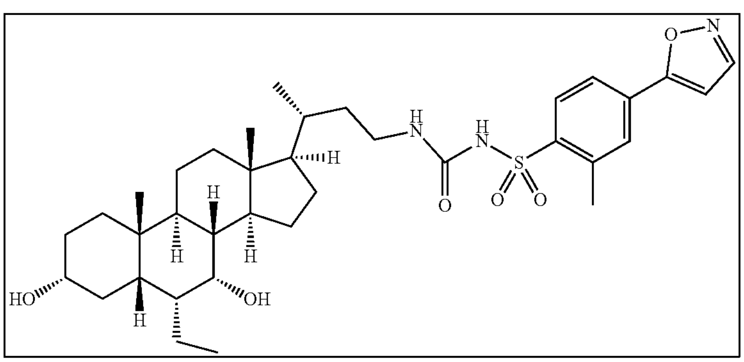 | 654.39 | |

TABLE 11-continued

| Example # | Structure | MS data (M − 1)⁻ | ¹H NMR (500 MHz) |
|---|---|---|---|
| 73 | 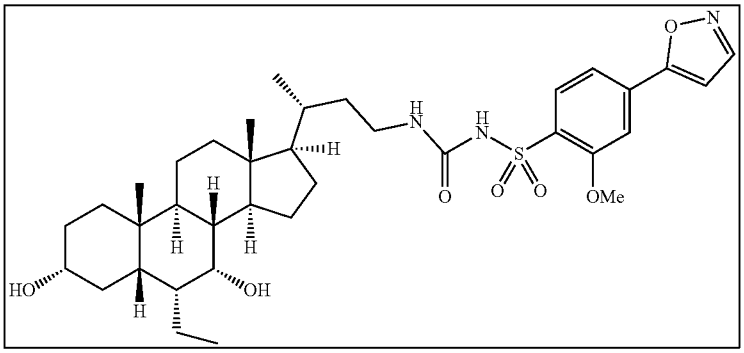 | 670.29 | |
| 74 | 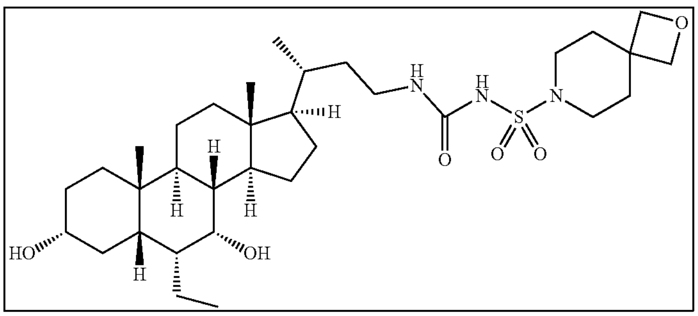 | 622.32 | |
| 75 | 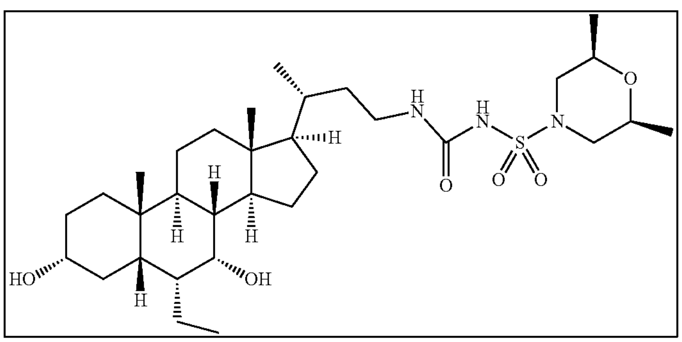 | 610.33 | |
| 76 | 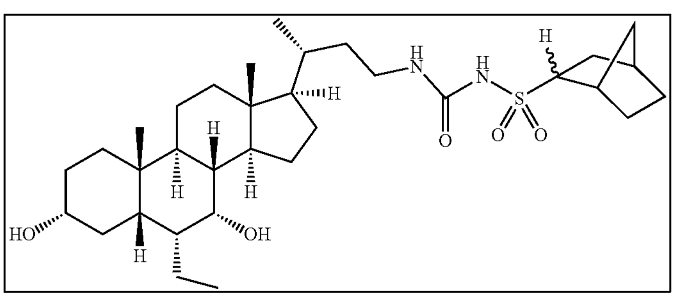 | 591.41 | |

TABLE 11-continued
| Example # | Structure | MS data (M − 1)⁻ | ¹H NMR (500 MHz) |
|---|---|---|---|
| 77 | 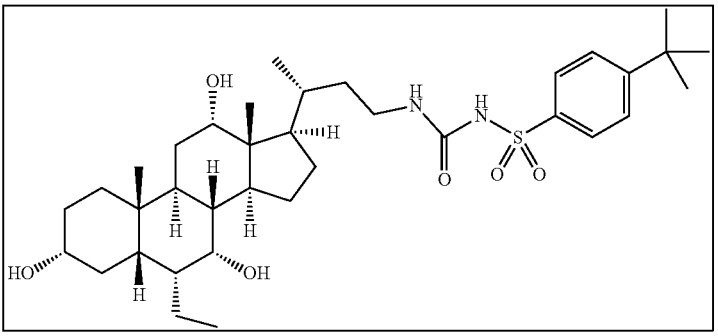 | 645.34 | |
| 78 | 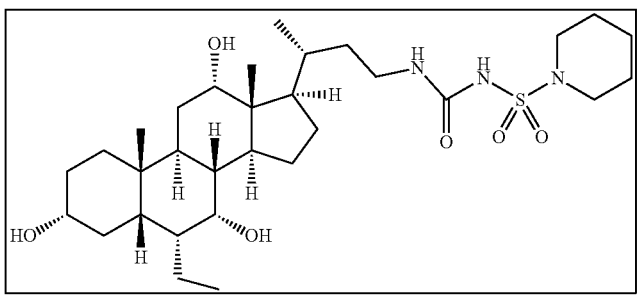 | 596.40 | |
| 79 | 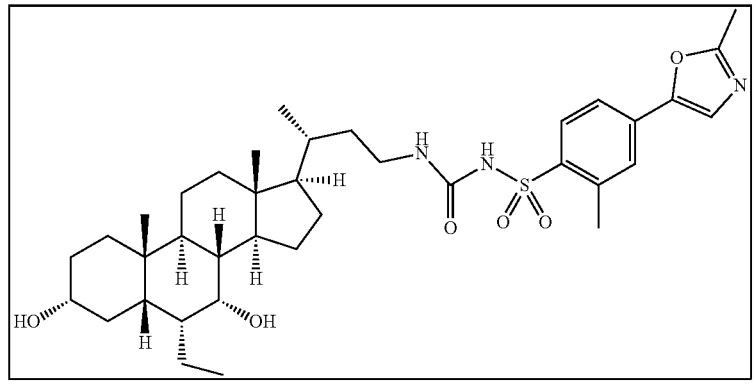 | 668.30 | |
| 80 | 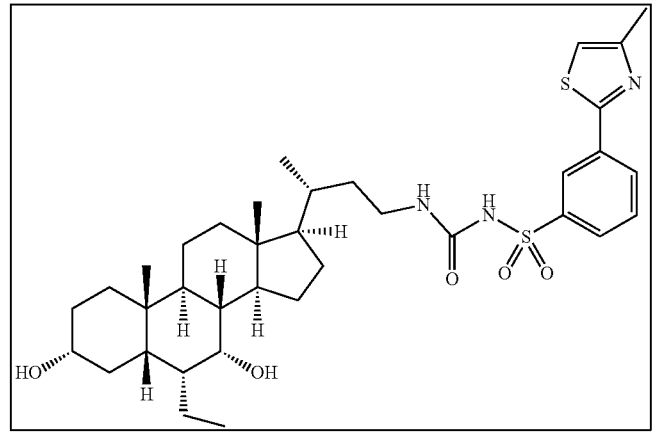 | 670.28 | |

TABLE 11-continued

| Example # | Structure | MS data (M − 1)⁻ | ¹H NMR (500 MHz) |
|---|---|---|---|
| 81 | 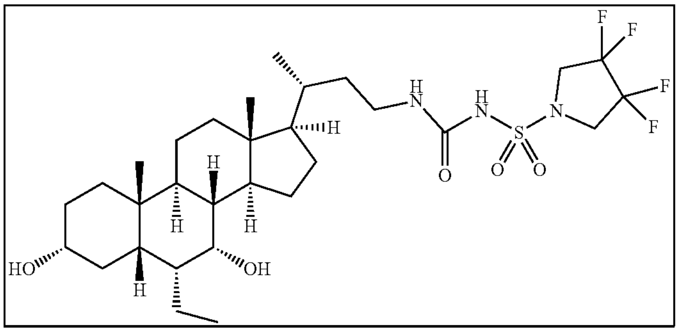 | 638.36 | |
| 82 | 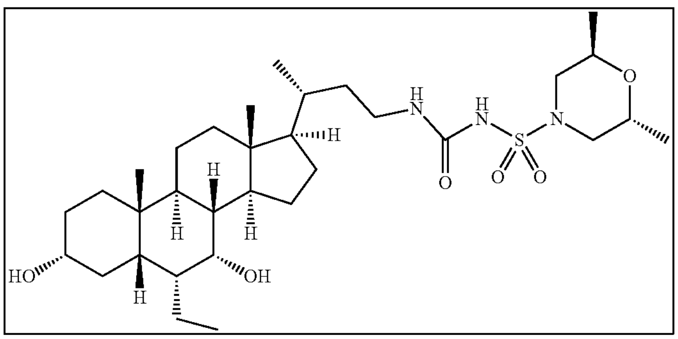 | 610.39 | |
| 83 | 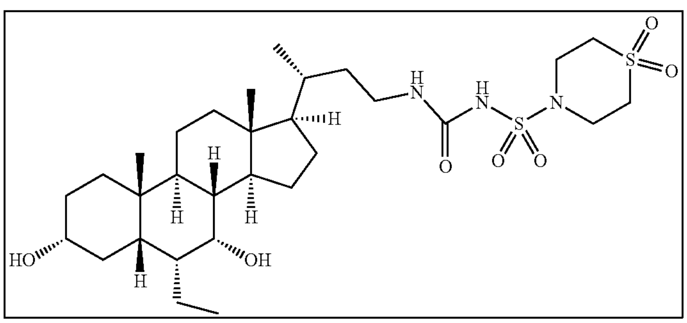 | 630.36 | |
| 84 | 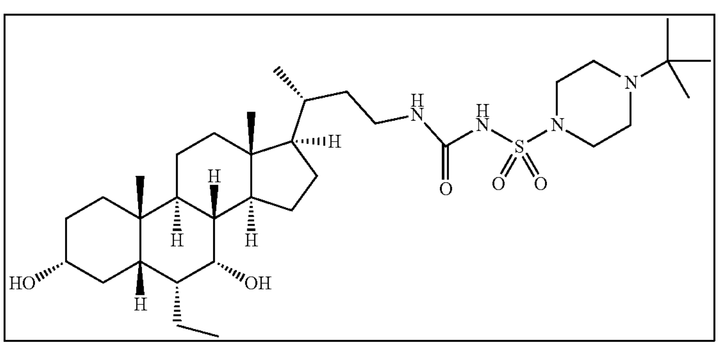 | 639.45 | |

TABLE 11-continued

| Example # | Structure | MS data (M − 1)⁻ | ¹H NMR (500 MHz) |
|---|---|---|---|
| 85 | 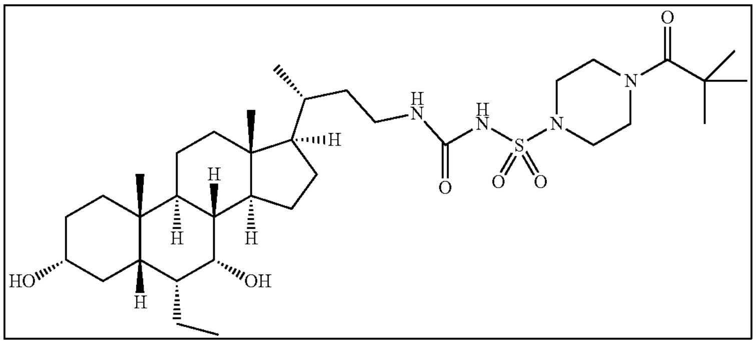 | 665.43 | |
| 86 | 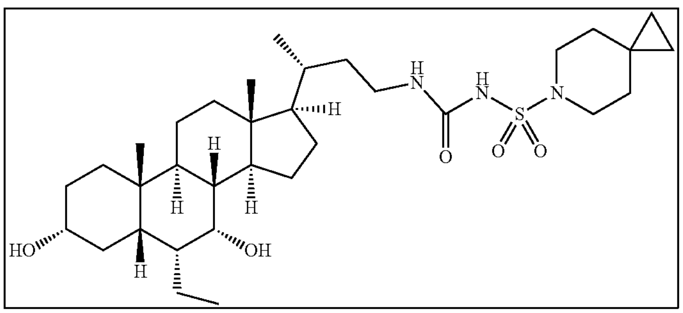 | 606.42 | |
| 87 | 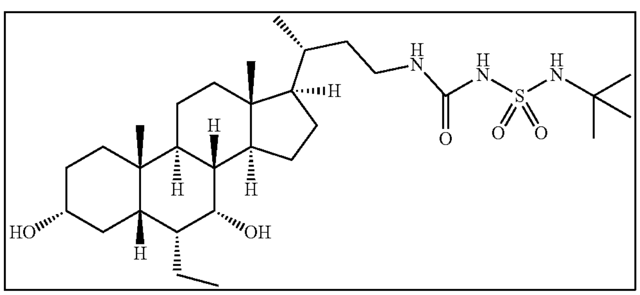 | 568.40 | |
| 88 | 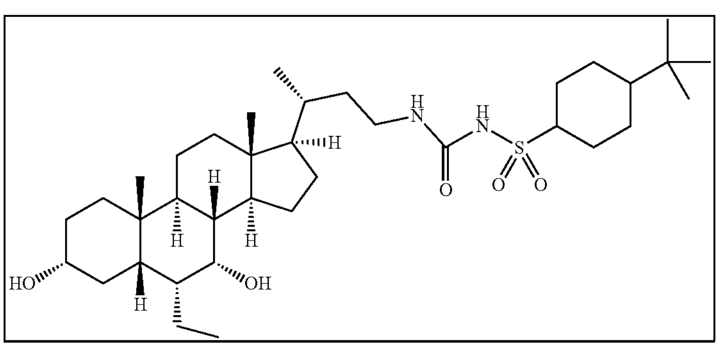 | 635.48 | |

TABLE 11-continued

| Example # | Structure | MS data (M − 1)⁻ | ¹H NMR (500 MHz) |
|---|---|---|---|
| 89 | 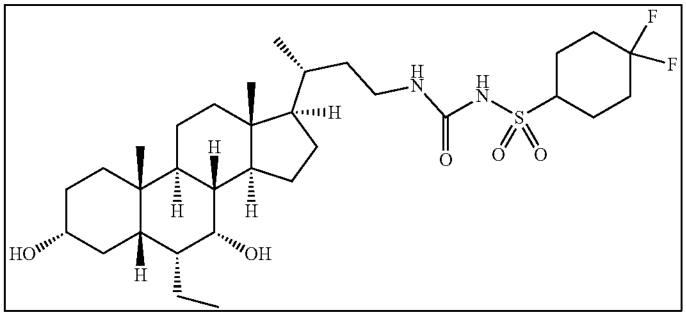 | 615.39 | |
| 90 | 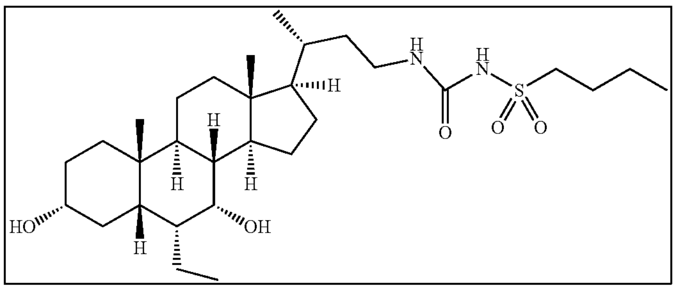 | 553.37 | |
| 91 | 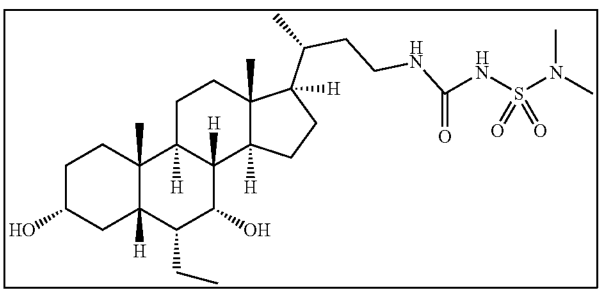 | 540.37 | |
| 92 | 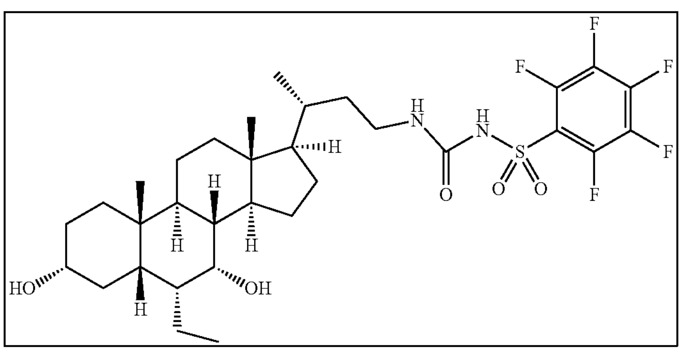 | 663.29 | |
| 93 | 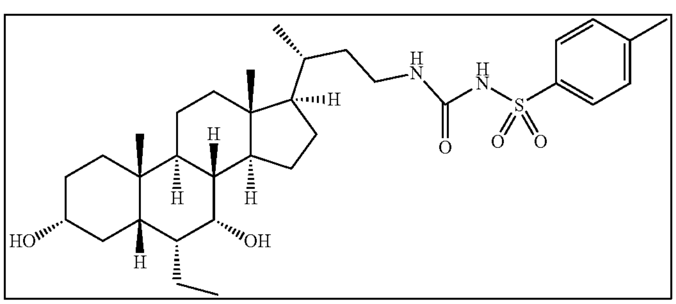 | 587.38 | |

TABLE 11-continued

| Example # | Structure | MS data (M − 1)⁻ | ¹H NMR (500 MHz) |
|---|---|---|---|
| 94 | 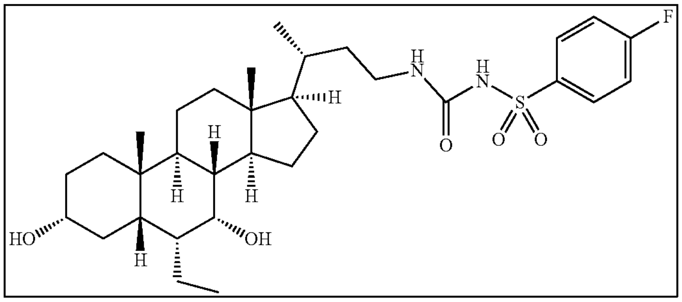 | 591.35 | |
| 95 | 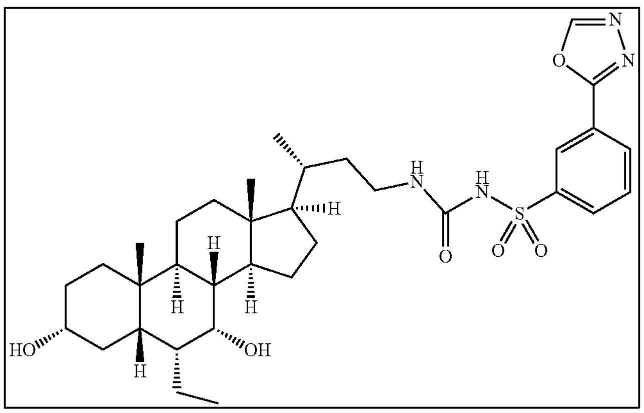 | 541.37 | |
| 96 | 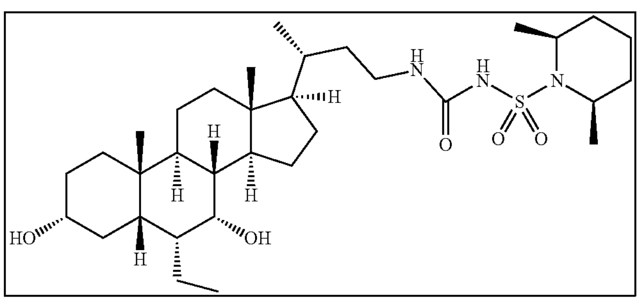 | 608.44 | |
| 97 | 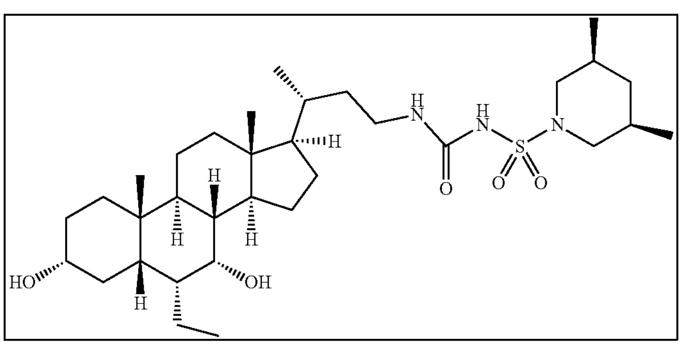 | 608.41 | |

TABLE 11-continued

| Example # | Structure | MS data (M − 1)⁻ | ¹H NMR (500 MHz) |
|---|---|---|---|
| 98 | 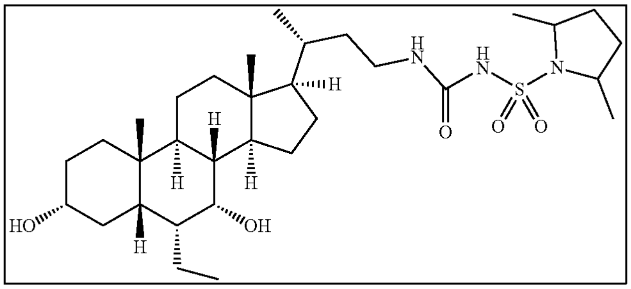 | 594.34 | |
| 99 | 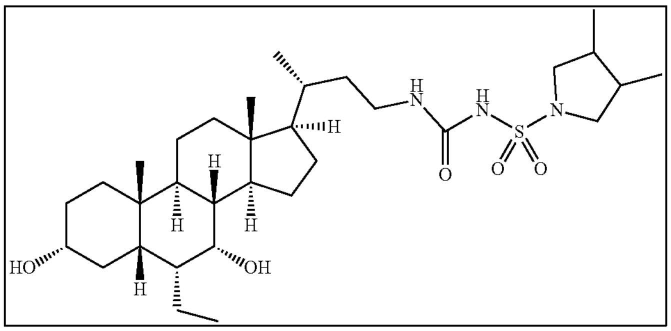 | 594.34 | |
| 100 | 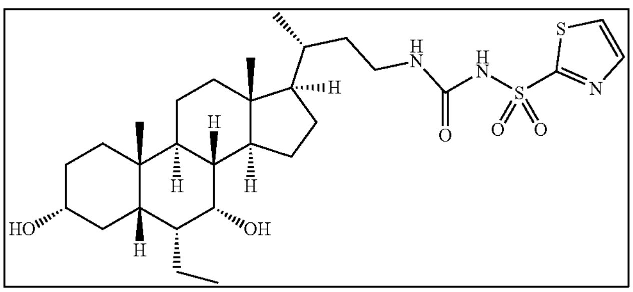 | 580.23 | |
| 101 | 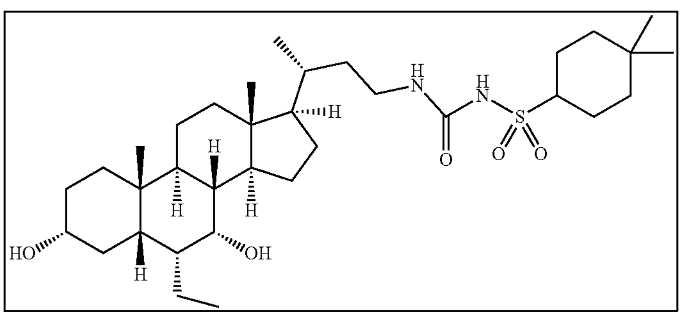 | 607.44 | |
| 102 | 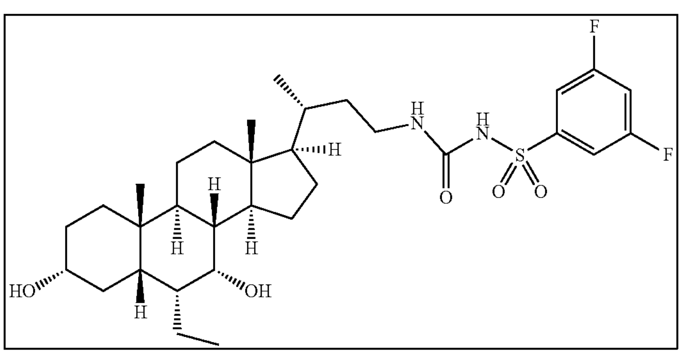 | 609.26 | |

TABLE 11-continued

| Example # | Structure | MS data (M − 1)⁻ | ¹H NMR (500 MHz) |
|---|---|---|---|
| 103 | 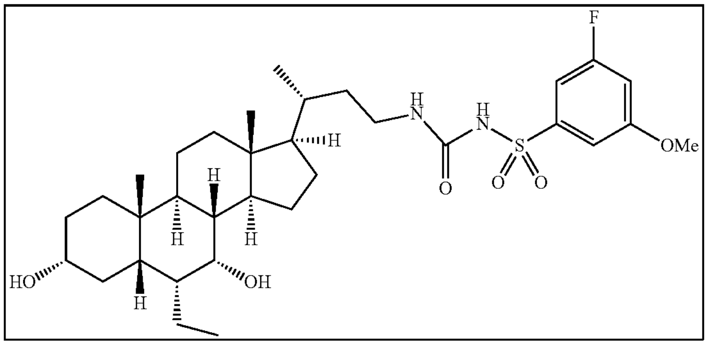 | 621.28 | |
| 104 | 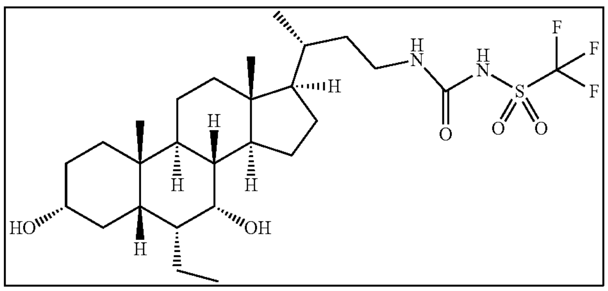 | 565.24 | |
| 105 | 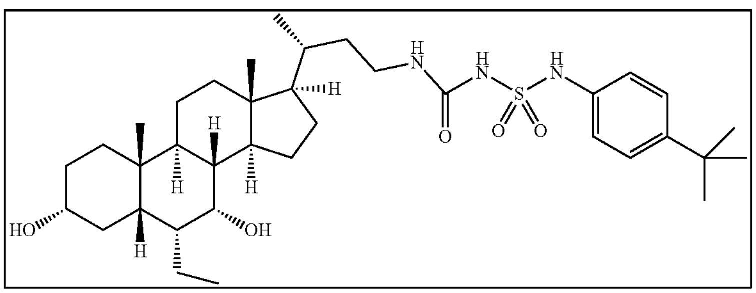 | 644.35 | |
| 106 | 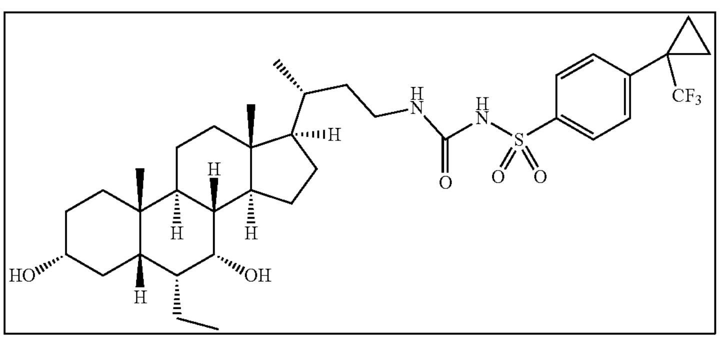 | 681.29 | |
| 107 | 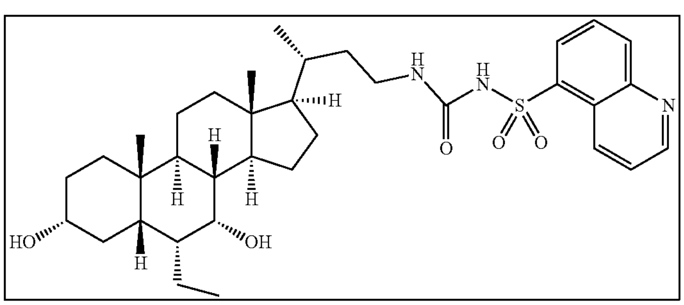 | 624.35 | |

TABLE 11-continued

| Example # | Structure | MS data (M − 1)⁻ | ¹H NMR (500 MHz) |
|---|---|---|---|
| 108 | 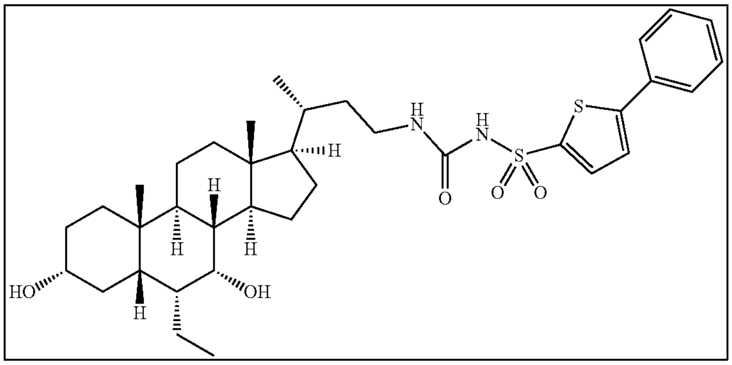 | 655.32 | |
| 109 | 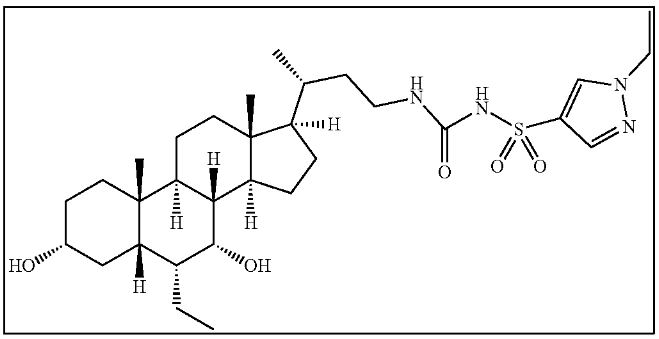 | 591.36 | |
| 110 | 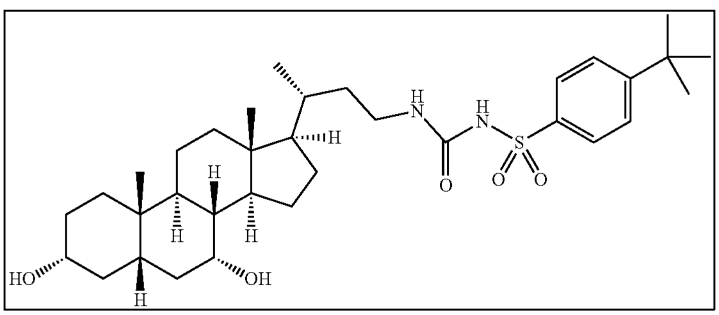 | 601.37 | |
| 111 | 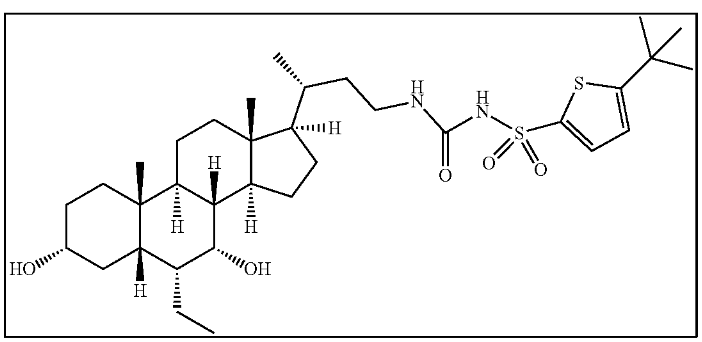 | 635.45 | |

TABLE 11-continued

| Example # | Structure | MS data (M − 1)⁻ | ¹H NMR (500 MHz) |
|---|---|---|---|
| 112 | 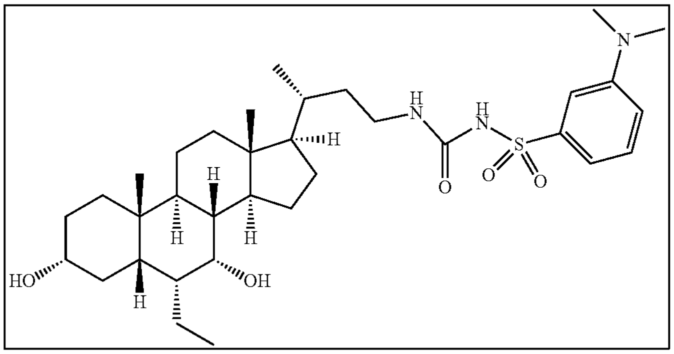 | M + 1, 618.50 | |
| 113 | 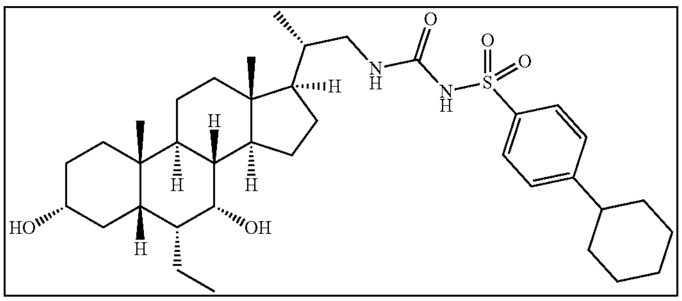 | 641.50 | |
| 114 | 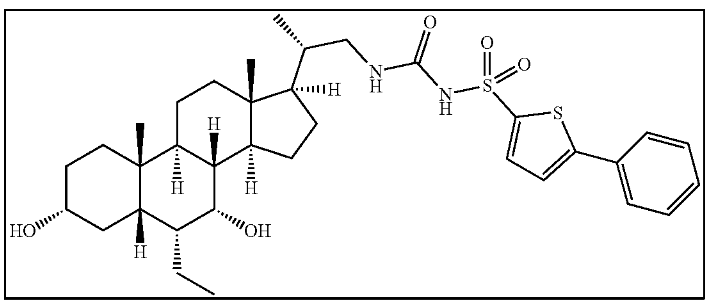 | 641.00 | |
| 115 | 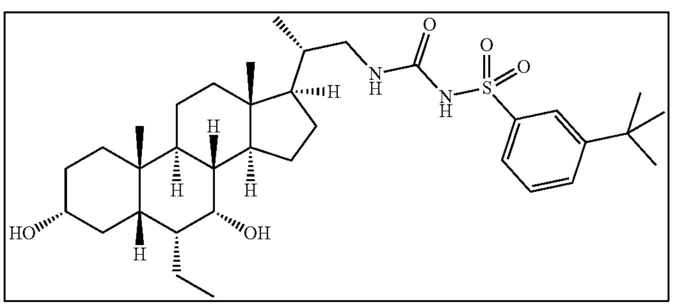 | 615.55 | |
| 116 | 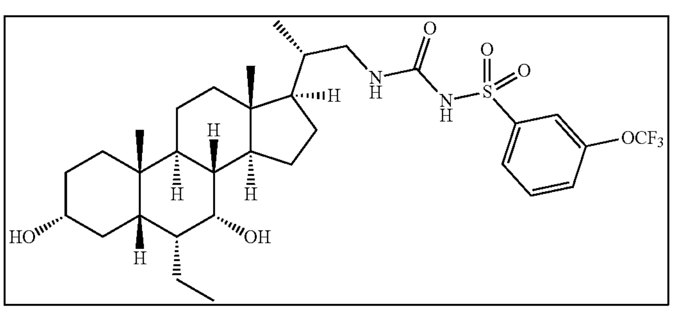 | 643.45 | |

TABLE 11-continued

| Example # | Structure | MS data (M − 1)⁻ | ¹H NMR (500 MHz) |
|---|---|---|---|
| 117 | 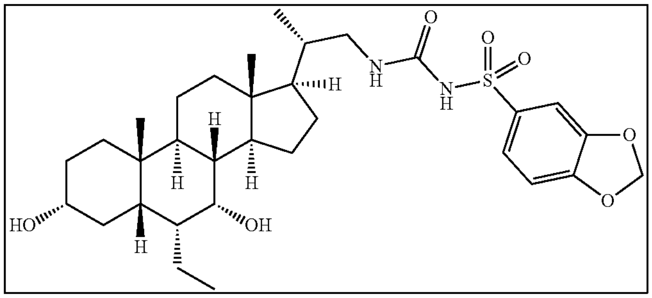 | 603.35 | |
| 118 | 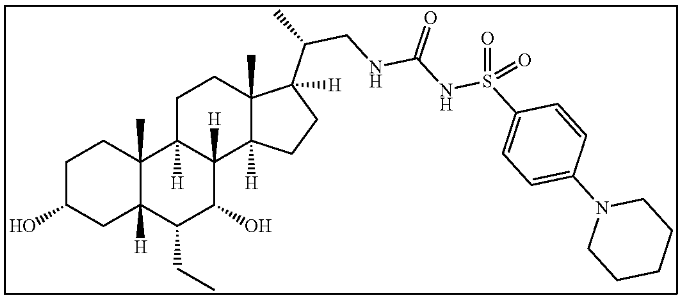 | M + 1, 644.40 | |
| 119 | 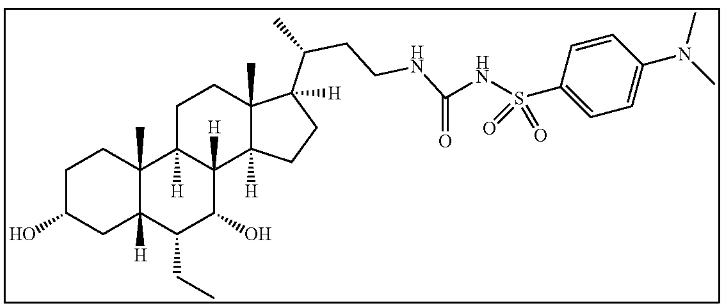 | 616.55 | |
| 120 | 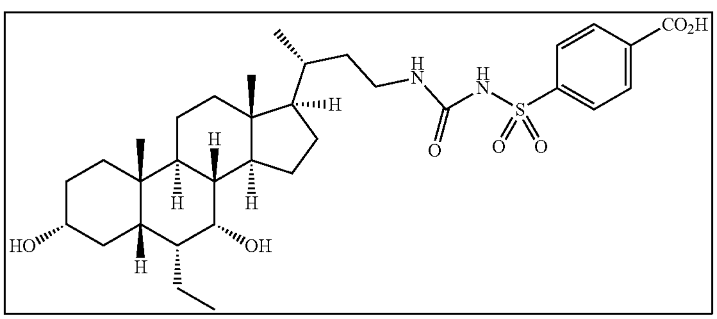 | 617.33 | |
| 121 | 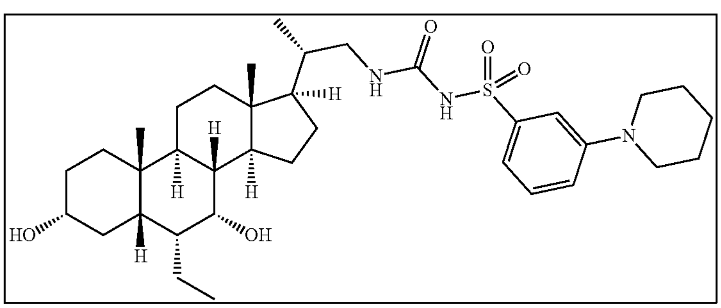 | M + 1, 644.60 | |

TABLE 11-continued
| Example # | Structure | MS data (M − 1)⁻ | ¹H NMR (500 MHz) |
|---|---|---|---|
| 122 | 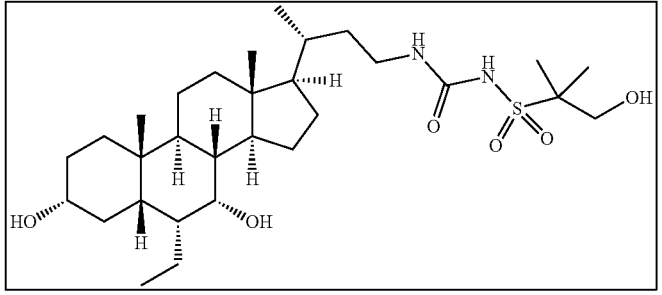 | M + 1, 571.45 | |
| 123 | 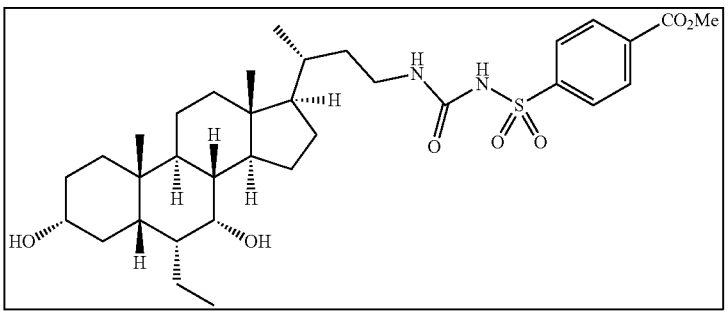 | 631.34 | |
| 124 | 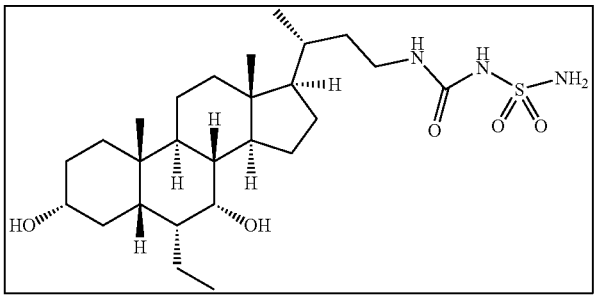 | 512.31 | |
| 125 | 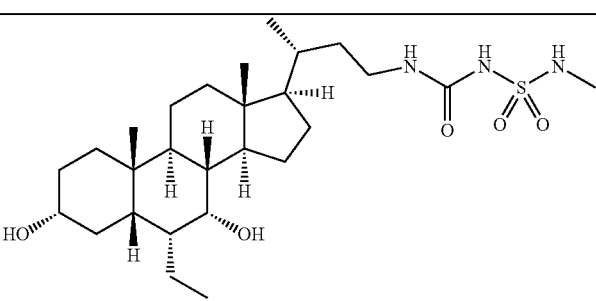 | 526.33 | |
| 126 | 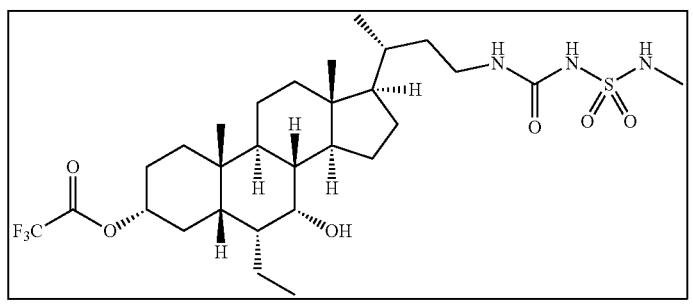 | 622.31 | |

TABLE 11-continued

| Example # | Structure | MS data (M − 1)⁻ | $^1$H NMR (500 MHz) |
|---|---|---|---|
| 127 | 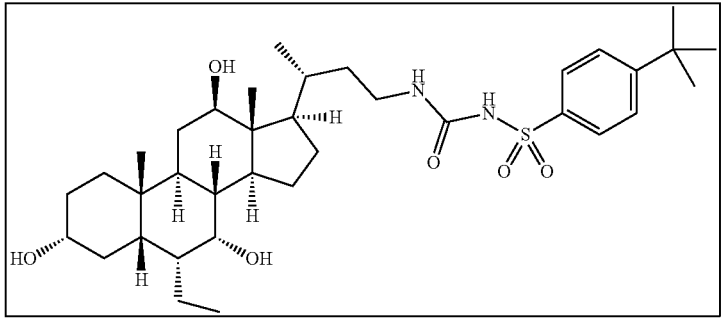 | 645.46 | |
| 128 | 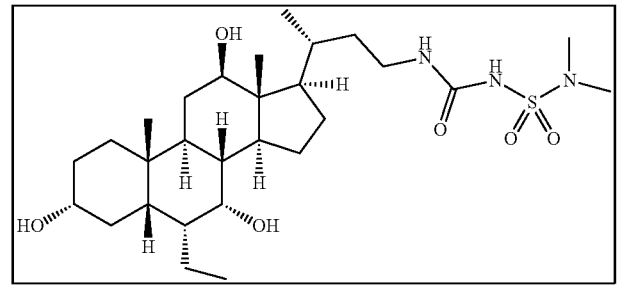 | 556.34 | |

Assays

Human FXR (NR1H4) Assay

Determination of a ligand mediated Gal4 promoter driven transactivation to quantify ligand binding mediated activation of FXR, FXR Reporter Assay kit purchased from Indigo Bioscience (Catalogue number: IB00601) to determine the potency and efficacy of compound developed by Enanta that can induce FXR activation. The principle application of this reporter assay system is to quantify functional activity of human FXR. The assay utilizes non-human mammalian cells, CHO (Chinese hamster ovary) cells engineered to express human NR1H4 protein (referred to as FXR). Reporter cells also incorporate the cDNA encoding beetle luciferase which catalyzes the substrates and yields photon emission. Luminescence intensity of the reaction is quantified using a plate-reading luminometer, Envision. Reporter Cells include the luciferase reporter gene functionally linked to an FXR responsive promoter. Thus, quantifying changes in luciferase expression in the treated reporter cells provides a sensitive surrogate measure of the changes in FXR activity. $EC_{50}$ and efficacy (normalize to CDCA set as 100%) is determined by XLFit. The assay is according to the manufacturer's instructions. In brief, the assay was performed in white, 96 well plates using final volume of 100 ul containing cells with different doses of compounds. Retrieve Reporter Cells from −80° C. storage. Perform a rapid thaw of the frozen cells by transferring a 10 ml volume of 37° C. cell recovery medium into the tube of frozen cells. Recap the tube of Reporter Cells and immediately place it in a 37° C. water bath for 5-10 minutes. Retrieve the tube of Reporter Cell Suspension from the water bath. Sanitize the outside surface of the tube with a 70% alcohol swab, and then transfer it into the cell culture hood. Dispense 90 µl of cell suspension into each well of the 96-well Assay Plate. Transfer the plate into 37° C. incubator, allowing the cells adherent to the bottom of the well. Dilute compounds in Dilution Plate (DP), and administrate to cells at Assay Plate (AP). DMSO content of the samples was kept at 0.2%. Cells were incubated for additional 22 hours before luciferase activities were measured. Thirty minutes before intending to quantify FXR activity, remove Detection Substrate and Detection Buffer from the refrigerator and place them in a low-light area so that they may equilibrate to room temperature. Remove the plate's lid and discard all media contents by ejecting it into an appropriate waste container. Gently tap the inverted plate onto a clean absorbent paper towel to remove residual droplets. Cells will remain tightly adhered to well bottoms. Add 100 µl of luciferase detection reagent to each well of the assay plate. Allow the assay plate to rest at room temperature for at least 5 minutes following the addition of LDR. Set the instrument (Envision) to perform a single 5 second "plate shake" prior to reading the first assay well. Read time may be 0.5 second (500 mSec) per well. $EC_{50}$ and Efficacy (normalize to CDCA set as 100%) is determined by XLFit.

In Vitro Human TGR5 (GPBAR1) Activity Assay

The potency and efficacy of the compounds of the invention on TGR5 receptor was evaluated using in vitro assays which carried out using the express kit from DiscoverX (cAMP HUNTER™ eXpress GPBAR1 CHO-K1 GPCR Assay; Cataloguer number: 95-0049E2CP2S)GPBAR1 (G protein-coupled bile acid receptor 1) encodes a member of the G protein-coupled receptor (GPCR) superfamily. GPBAR1 activation following ligand binding initiates a series of second messenger cascades that result in a cellular response. Treatment of CHO cells expressing GPBAR1 with bile acids induces the production of intracellular cAMP and internalization of the receptor. The potency and efficacy of compound for GPBAR1 activation by measuring cyclic adenosine monophosphate (cyclic AMP or cAMP) levels in live cells using a competitive immunoassay based on Enzyme Fragment Complementation (EFC).

In briefly, following seeding the cells into the white, 96 well microplate, place it in a 37° C., 5% CO2 in a humidified incubator for 18-24 hours prior to testing. On second day, proceed to the appropriate cAMP HUNTER™ eXpress Protocol according to the manufacturer's instructions. Dissolve agonist compound in DMSO at the desired stock concentration, and prepare 3-fold serial dilutions of agonist compound in Cell Assay Buffer. The concentration of each dilution should be prepared at 4× of the final screening concentration (i.e. 15 µL compound+45 µL Cell Assay Buffer/cAMP Antibody Reagent). For each dilution, the final concentration of solvent should remain constant. Transfer 15 µL diluted compound the assay plate and incubate the plate for 30 minutes at 37° C. Following agonist incubation, add 60 µL of working cAMP detection reagents/cAMP Solution mixture (cAMP Lysis Buffer, Substrate Reagent 1, cAMP Solution D) to the appropriate wells. Incubate for 1 hour at room temperature (23° C.), protected from light. Add 60 µl of cAMP Solution A to the appropriate wells. Incubate for 3 hours at room temperature (23° C.), protected from light. Read samples on Envision standard luminescence plate reader. Calculate of average $EC_{50}$ after logarithm transformation.

To assess the FXR agonistic potency of the example compounds as well as for reference compound, potency ranges were determined in the Human FXR (NR1H4) Assay as listed below in Table 12. The efficacy was normalized to CDCA set as 100%. (A=EC50<0.1 µM; B=0.1 µM<EC50<1.0 µM; C=1.0 µM<EC50<10 µM; D=EC50>10 µM)

TABLE 12

| Example | EC50 (uM) | Efficacy (%) |
|---|---|---|
| CDCA | D | 100 |
| 6-ECDCA | B | 223 |
| 1 | A | 337 |
| 2 | A | 300 |
| 3 | A | 396 |
| 4 | A | 342 |
| 5 | B | 369 |
| 6 | B | 269 |
| 7 | C | 259 |
| 8 | n/a | n/a |
| 10 | B | 168 |
| 11 | C | 267 |
| 12 | A | 327 |
| 13 | A | 245 |
| 14 | B | 295 |
| 15 | A | 337 |
| 16 | A | 265 |
| 17 | A | 357 |
| 18 | A | 319 |
| 19 | B | 323 |
| 20 | B | 334 |
| 21 | B | 402 |
| 22 | A | 477 |
| 23 | A | 488 |
| 24 | A | 421 |
| 25 | A | 357 |
| 26 | B | 378 |
| 27 | A | 275 |
| 28 | A | 323 |
| 29 | C | 299 |
| 30 | C | 194 |
| 31 | B | 305 |
| 32 | A | 309 |
| 33 | A | 270 |
| 34 | A | 219 |
| 35 | B | 217 |
| 36 | B | 228 |
| 37 | A | 254 |
| 38 | A | 231 |
| 39 | A | 379 |
| 40 | B | 244 |
| 41 | B | 350 |
| 42 | B | 343 |
| 43 | C | 264 |
| 44 | na | 1 |
| 45 | C | 178 |
| 46 | A | 315 |
| 47 | A | 361 |
| 48 | A | 420 |
| 49 | C | 236 |
| 50 | A | 309 |
| 51 | A | 319 |
| 52 | B | 281 |
| 53 | A | 263 |
| 54 | A | 273 |
| 55 | A | 271 |
| 56 | B | 295 |
| 57 | A | 297 |
| 58 | A | 307 |
| 59 | B | 344 |
| 60 | A | 346 |
| 61 | A | 403 |
| 62 | C | 476 |
| 63 | B | 452 |
| 64 | C | 334 |
| 65 | A | 498 |
| 66 | A | 375 |
| 67 | A | 351 |
| 68 | A | 458 |
| 69 | A | 490 |
| 70 | A | 434 |
| 71 | B | 419 |
| 72 | B | 384 |
| 73 | B | 444 |
| 74 | B | 242 |
| 75 | A | 323 |
| 76 | A | 290 |
| 77 | C | 89 |
| 78 | C | 210 |
| 79 | B | 249 |
| 80 | B | 295 |
| 81 | A | 315 |
| 82 | A | 321 |
| 83 | C | 348 |
| 84 | B | 351 |
| 85 | B | 324 |
| 86 | A | 390 |
| 87 | B | 343 |
| 88 | A | 378 |
| 89 | A | 351 |
| 90 | A | 407 |
| 91 | A | 399 |
| 92 | C | 325 |
| 93 | A | 443 |
| 94 | A | 361 |
| 95 | C | 245 |
| 96 | A | 387 |
| 97 | A | 308 |
| 98 | A | 344 |
| 99 | A | 266 |
| 100 | C | 364 |
| 101 | A | 244 |
| 102 | A | 210 |
| 103 | A | 328 |
| 104 | C | 298 |
| 105 | B | 322 |
| 106 | A | 281 |
| 107 | B | 311 |
| 108 | B | 203 |
| 109 | B | 219 |
| 110 | C | 320 |
| 111 | A | 314 |
| 112 | A | 287 |
| 113 | A | 366 |
| 114 | A | 322 |
| 115 | B | 291 |
| 116 | A | 322 |

TABLE 12-continued

| Example | EC50 (uM) | Efficacy (%) |
|---|---|---|
| 117 | A | 305 |
| 118 | A | 267 |
| 119 | A | 363 |
| 120 | C | 198 |
| 121 | B | 199 |
| 122 | C | 121 |
| 123 | B | 271 |
| 124 | C | 195 |
| 125 | C | 256 |
| 126 | C | 238 |
| 127 | C | 210 |
| 128 | C | 405 |
| 129 | n/a | n/a |
| 130 | C | 146 |
| 131 | C | 8 |
| 132 | C | 7 |
| 133 | D | 80 |
| 134 | n/a | 19 |
| 135 | C | 4 |
| 136 | C | 159 |
| 137 | C | 105 |
| 138 | C | 2 |
| 139 | C | 138 |
| 140 | n/a | 1 |
| 141 | C | 16 |
| 142 | n/a | 7 |
| 143 | n/a | 6 |

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by Formula IV-A or a pharmaceutically acceptable salt thereof:

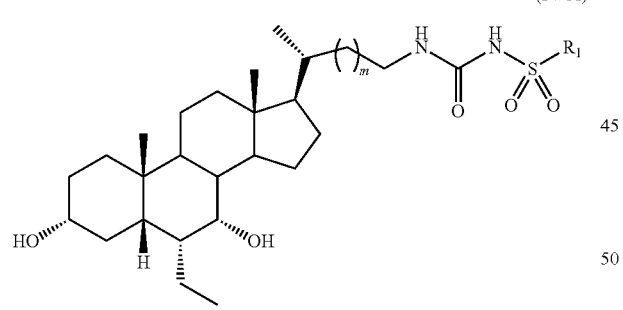

(IV-A)

wherein:

$R_1$ is selected from the group consisting of:
1) Halogen;
2) Hydroxyl;
3) Substituted or unsubstituted —$C_1$-$C_8$ alkyl;
4) Substituted or unsubstituted —$C_2$-$C_8$ alkenyl;
5) Substituted or unsubstituted —$C_2$-$C_8$ alkynyl;
6) Substituted or unsubstituted —$C_3$-$C_8$ cycloalkyl;
7) Substituted or unsubstituted aryl;
8) Substituted or unsubstituted arylalkyl;
9) Substituted or unsubstituted heterocycloalkyl;
10) Substituted or unsubstituted heteroaryl;
11) Substituted or unsubstituted heteroarylalkyl; and
12) —$NR_{10}R_{11}$;

$R_{10}$ and $R_{11}$ are each independently selected from hydrogen, substituted or unsubstituted —$C_1$-$C_8$ alkyl, substituted or unsubstituted —$C_2$-$C_8$ alkenyl, substituted or unsubstituted —$C_2$-$C_8$ alkynyl, substituted or unsubstituted —$C_3$-$C_8$ cycloalkyl, substituted or unsubstituted heterocycloalkyl, or $R_{10}$ and $R_{11}$ are taken together with the nitrogen atom they attached to form a heterocyclic ring; and m is selected from 0, 1, 2 and 3.

2. The compound of claim 1, wherein $R_1$ is $C_1$-$C_4$-alkyl, halogenated $C_1$-$C_4$-alkyl, $C_1$-$C_4$-alkenyl, phenyl-$C_1$-$C_4$-alkyl, substituted or unsubstituted $C_3$-$C_6$-cycloalkyl, $C_1$-$C_6$-cycloalkyl-$C_1$-$C_4$-alkyl, 5- or 6-membered heterocycloalkyl, amino, substituted or unsubstituted phenyl or halogen.

3. The compound of claim 1, wherein $R_1$ is selected from the groups set forth in the table below:

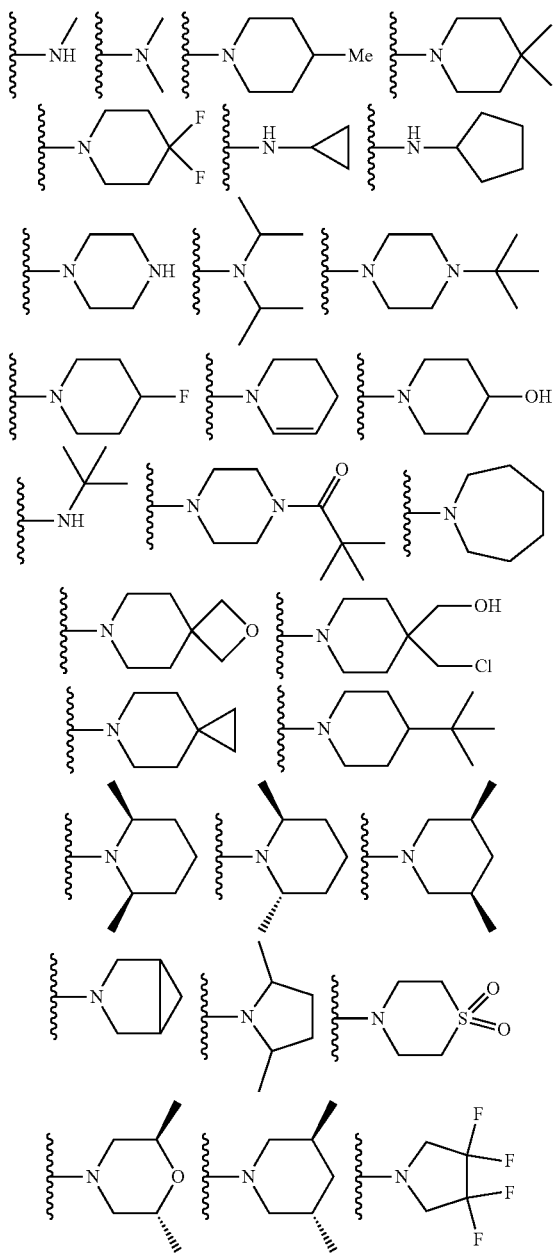

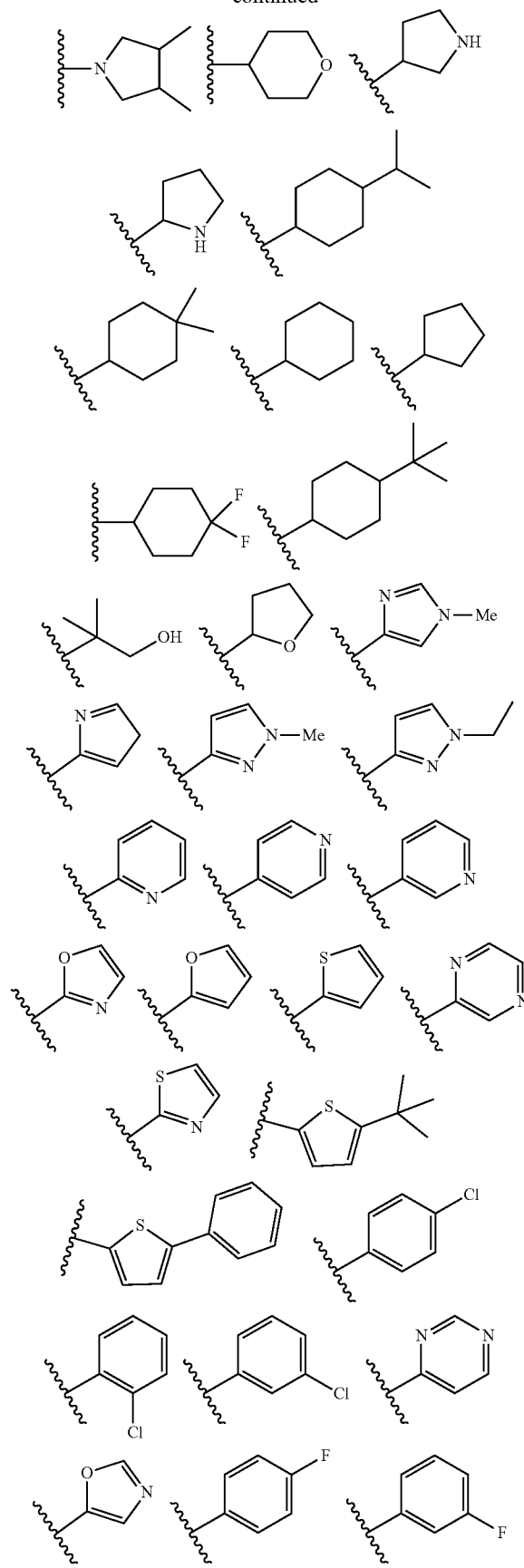
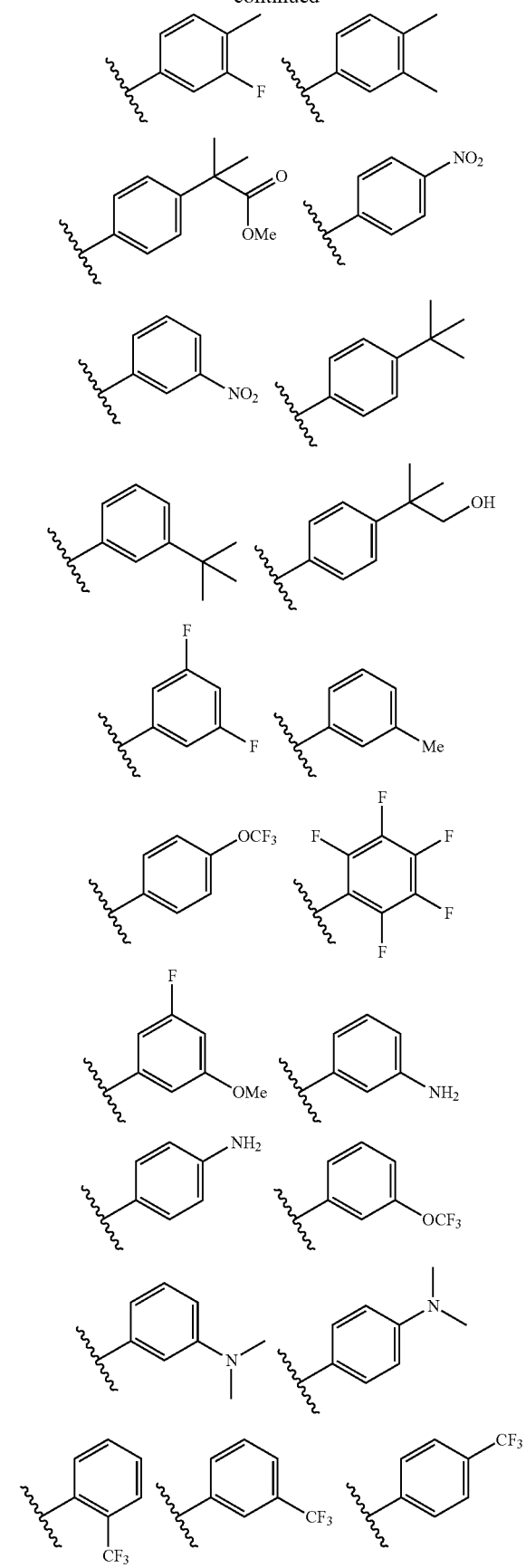

187
-continued
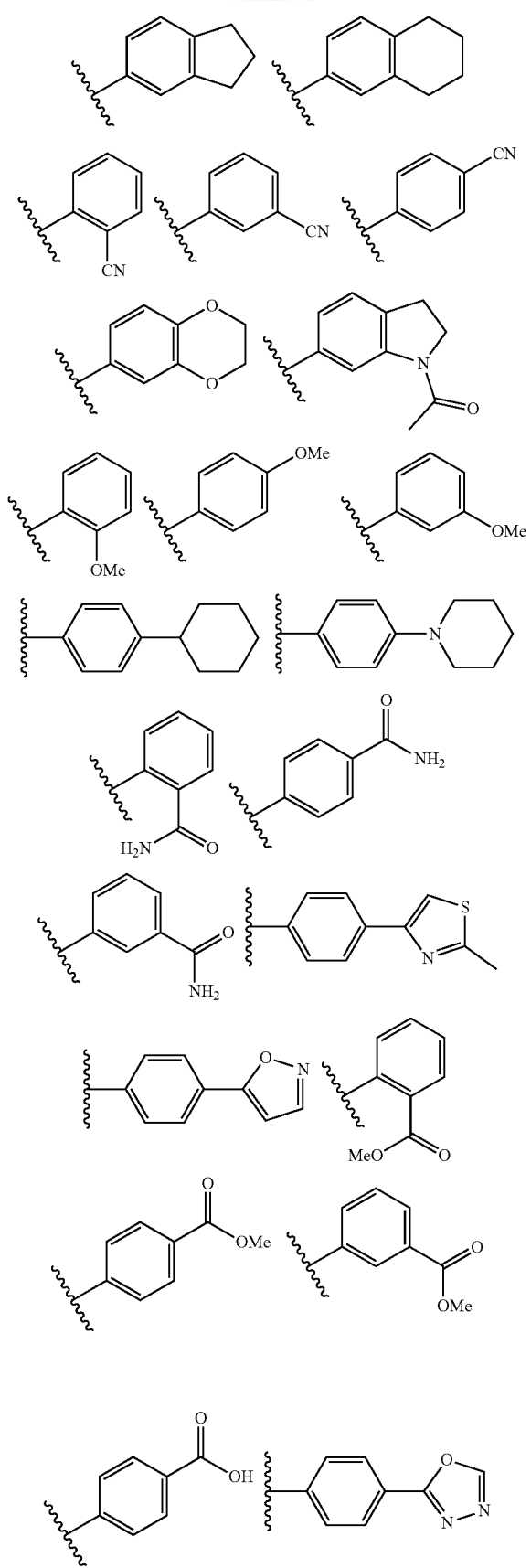
188
-continued
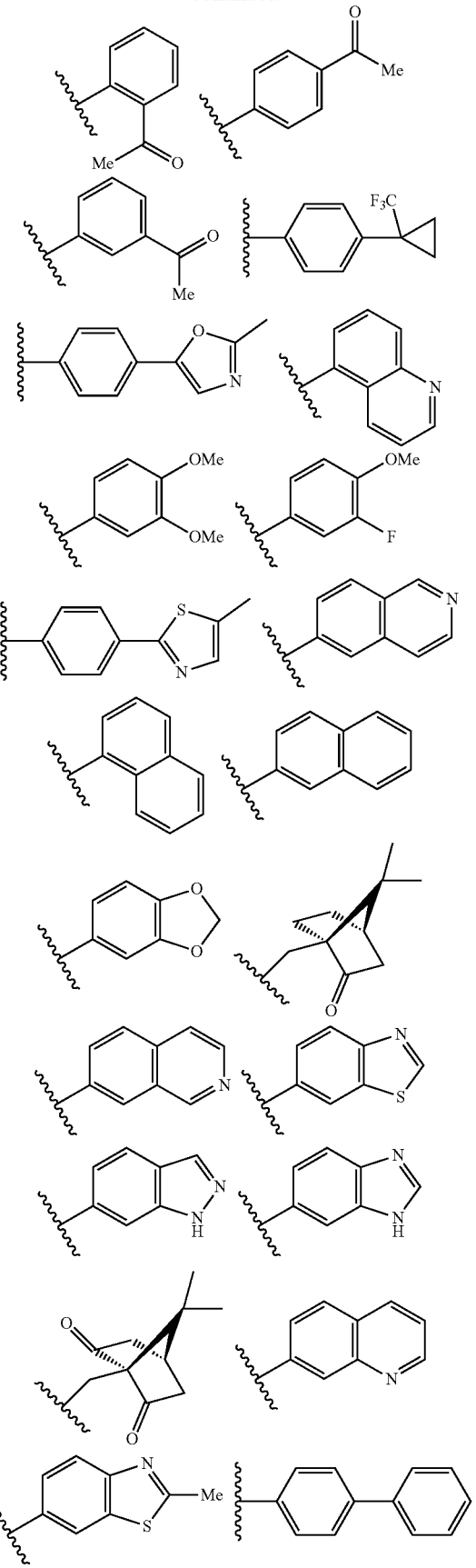

-continued

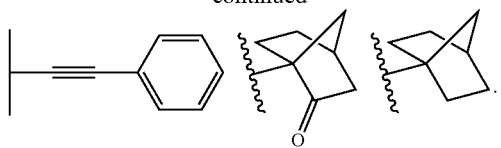

4. The compound of claim 1, wherein $R_1$ is ethyl, butyl, t-butyl, propyl, benzyl, vinyl, allyl, $CF_3$,

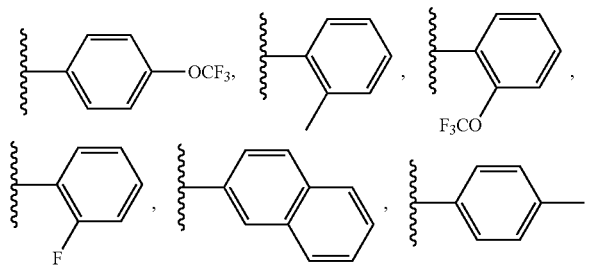

$NH_2$,

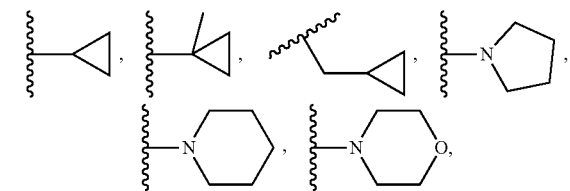

or fluoro.

5. The compound of claim 1, wherein $R_1$ is dimethylamino or p-tert-butylphenyl.

6. The compound of claim 1, wherein m is 1.

7. A pharmaceutical composition comprising a compound according to claim 1 and a pharmaceutically acceptable carrier.

8. A method for ameliorating a disease or condition selected from the group consisting of primary biliary cirrhosis, cerebrotendinous xanthomatosis, primary sclerosing cholangitis, alcoholic liver disease, nonalcoholic fatty liver disease, nonalcoholic steatohepatitis, atherosclerosis, hypercholesterolemia, hypertriglyceridemia, Type II diabetes, and hepatocellular carcinoma in a subject in need thereof, comprising administering to the subject a therapeutically effective amount of a compound according to claim 1.

9. The method according to claim 8, wherein the disease or condition is primary biliary cirrhosis, nonalcoholic fatty liver disease, or nonalcoholic steatohepatitis.

10. A method for ameliorating nonalcoholic steatohepatitis in a subject in need thereof, comprising administering to the subject a therapeutically effective amount of a compound of claim 1.

11. A method for ameliorating nonalcoholic fatty liver disease in a subject in need thereof, comprising administering to the subject a therapeutically effective amount of a compound of claim 1.

12. A method for ameliorating primary biliary cirrhosis in a subject in need thereof, comprising administering to the subject a therapeutically effective amount of a compound of claim 1.

13. A method for ameliorating nonalcoholic steatohepatitis in a subject in need thereof, comprising administering to the subject a therapeutically effective amount of a compound of claim 3.

14. A method for ameliorating nonalcoholic fatty liver disease in a subject in need thereof, comprising administering to the subject a therapeutically effective amount of a compound of claim 3.

15. A method for ameliorating primary biliary cirrhosis in a subject in need thereof, comprising administering to the subject a therapeutically effective amount of a compound of claim 3.

* * * * *

UNITED STATES PATENT AND TRADEMARK OFFICE
CERTIFICATE OF CORRECTION

PATENT NO. : 10,696,713 B2
APPLICATION NO. : 16/222380
DATED : June 30, 2020
INVENTOR(S) : Guoqiang Wang et al.

It is certified that error appears in the above-identified patent and that said Letters Patent is hereby corrected as shown below:

In the Claims

At Column 188

In Claim 3, at Line 55, delete " 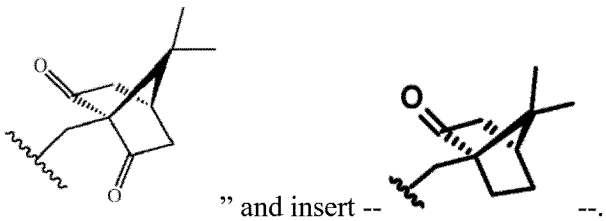 " and insert -- --.

At Column 189

In Claim 3, at Line 5, delete " 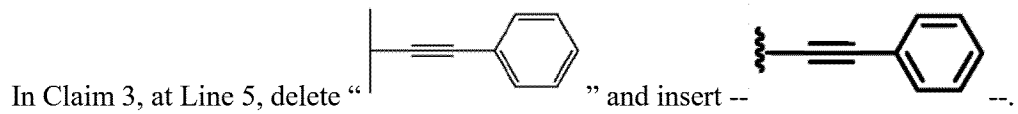 " and insert --  --.

Signed and Sealed this
Twenty-second Day of September, 2020

Andrei Iancu
*Director of the United States Patent and Trademark Office*